US008188121B2

(12) United States Patent
Tidwell et al.

(10) Patent No.: US 8,188,121 B2
(45) Date of Patent: May 29, 2012

(54) SUBSTITUTED PYRIDINES AS ANTIPARASITIC AZA TERARYL COMPOUNDS

(75) Inventors: Richard R. Tidwell, Pittsboro, NC (US); David W. Boykin, Atlanta, GA (US); W. David Wilson, Atlanta, GA (US); Reto Brun, Therwil (CH); Karl Werbovetz, Worthington, OH (US); Mohamed A. Ismail, Atlanta, GA (US); Reem K. Arafa, Cairo (EG); Laixing Hu, Decatur, GA (US)

(73) Assignees: The University of North Carolina at Chapel Hill, Chapel Hill, NC (US); Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 13/162,907

(22) Filed: Jun. 17, 2011

(65) Prior Publication Data
US 2011/0257199 A1 Oct. 20, 2011

Related U.S. Application Data

(60) Division of application No. 11/698,257, filed on Jan. 25, 2007, now Pat. No. 7,964,619, which is a continuation-in-part of application No. 11/436,045, filed on May 17, 2006, now Pat. No. 8,101,636.

(60) Provisional application No. 60/687,092, filed on Jun. 3, 2005.

(51) Int. Cl.
*A61K 31/44* (2006.01)
(52) U.S. Cl. .......... 514/340; 544/405; 546/257
(58) Field of Classification Search .......... 514/340; 544/405; 546/257
See application file for complete search history.

(56) References Cited

U.S. PATENT DOCUMENTS

| | | | |
|---|---|---|---|
| 5,521,189 A | 5/1996 | Boykin et al. | |
| 5,550,295 A | 8/1996 | Hillhouse | |
| 5,628,984 A | 5/1997 | Boucher, Jr. | |
| 7,964,619 B2 | 6/2011 | Tidwell et al. | |
| 8,101,636 B2 | 1/2012 | Tidwell et al. | |
| 2002/0082267 A1 | 6/2002 | Gerusz et al. | |
| 2003/0119803 A1 | 6/2003 | Stranix et al. | |
| 2005/0119481 A1 | 6/2005 | Rehwinkel et al. | |
| 2005/0148646 A1 | 7/2005 | Boykin et al. | |
| 2006/0293328 A1 | 12/2006 | Tidwell et al. | |
| 2007/0037813 A1 | 2/2007 | Aliagas-Martin et al. | |
| 2007/0037814 A1 | 2/2007 | Rawson et al. | |
| 2007/0105858 A1 | 5/2007 | Mabire et al. | |
| 2007/0197549 A1 | 8/2007 | Johansson et al. | |
| 2007/0232586 A1 | 10/2007 | Ohmoto et al. | |
| 2007/0232621 A1 | 10/2007 | Tidwell et al. | |

FOREIGN PATENT DOCUMENTS

| | | |
|---|---|---|
| EP | 1 736 466 | 12/2006 |
| WO | WO96/40138 | 12/1996 |
| WO | WO2004/050018 | 6/2004 |
| WO | WO2005/025565 | 3/2005 |
| WO | WO2005/033065 | 4/2005 |
| WO | WO2005/040132 | 5/2005 |

OTHER PUBLICATIONS

Altman et al., "Phenotypic Analysis of Antigen-Specific T Lymphocytes," Science. vol. 274 pp. 94-96 (1996).
Ansede et al., "O-Alkoxyamidine Prodrugs of Furamidine: In Vitro Transport and Microsomal Metabolism as Indicators of In Vivo Efficacy in a Mouse Model of *Trypanosoma brucei rhodesiense* Infection," Journal of Medicinal Chemistry. vol. 47 pp. 4335-4338 (2004).
Ashley et al. "A chemotherapeutic comparison of the trypanocidal action of some aromatic diamidines," Journal of the Chemical Society. pp. 103-116 (1942).
Bailly et al., "Relationship between topoisomerase II inhibition, sequence-specificity and DNA binding mode of dicationic diphenylfuran derivatives," Anti-Cancer Drug Design. vol. 14, No. 1 pp. 47-60 (1999).
Bouteille et al., "Treatment perspectives for human trypanosomiasis," Fundamental Clinical Pharmacology. vol. 17, pp. 171-181 (2003).
Boykin et al., "2,5-Bis[4-(N-alkylamidino)phenyl]furans as Anti-Pneumocystis carinii Agents," Journal of Medicinal Chemistry. vol. 41 pp. 124-129 (1998).
Boykin et al., "Anti-Pneumocystis Activity of Bis-amidoximes and Bis-O-alkylamidoximes Prodrugs," Bioorganic and Medicinal Chemistry Letters. vol. 6 pp. 3017-3020 (1996).
Boykin et al., "Dicationic Diarylfurans as Anti-Pneumocystis Carinii Agents," Journal of Medicinal Chemistry. vol. 38 pp. 912-916 (1995).
Brun et al., "In Vitro Typanocidal Activities of New S-Adenosylmethionine Decarboxylase Inhibitors," Antimicrobial Agents and Chemotherapy. vol. 40, No. 6 pp. 1442-1447 (1996).
Cory et al., "Structure and DNA Binding Activity of Analogues of 1,5-Bis(4-amidinophenoxy)pentane (Pentamidine)," Journal of Medicinal Chemistry. vol. 35 pp. 431-438 (1992).

(Continued)

*Primary Examiner* — James O Wilson
*Assistant Examiner* — Douglas M Willis
(74) *Attorney, Agent, or Firm* — Jenkins, Wilson, Taylor & Hunt, P.A.

(57) ABSTRACT

Novel aza analogues of dicationic terphenyl compounds for use in combating microbial infections are described. The compounds include those of Formula (III):

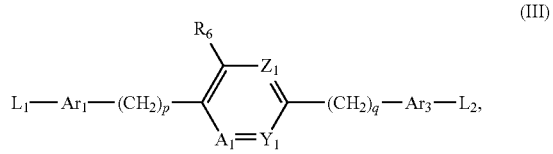

wherein one of $A_1$, $Y_1$, and $Z_1$ is N; $Ar_1$ is phenylene; and $Ar_3$ is a nitrogen-containing aromatic group. An exemplary compound of Formula (III) is:

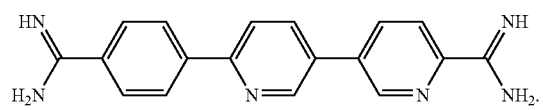

9 Claims, No Drawings

OTHER PUBLICATIONS

Czarny et al., "Analysis of van der Waals and Electrostatic Contributions in the Interactions of Minor Groove Binding Benzimidazoles with DNA," Journal of American Chemical Society. vol. 117, No. 16 pp. 4716-4717 (1995).

Dann et al., "Trypanocide Diamidine Mit Drei Isolierten Ringsystemen," Justus Liebigs Annalen der Chemie. pp. 160-194 (1975).

Das, B. P., and Boykin, D. W., "Synthesis and Antiprotozoal Activity of 2,5-Bis(4-guanylphenyl)furans," Journal of Medicinal Chemistry. vol. 20, No. 4 pp. 531-536 (1976).

Das et al., "Synthesis and Antitrypanosomal Activity of Some Bis(4-guanylphenyl) Five- and Six-Membered Ring Heterocycles," Journal of Medicinal Chemistry. vol. 23, No. 5 pp. 578-581 (1980).

Dorwald, "Side Reactions in Organic Synthesis: A Guide to Successful Synthesis Design," Weinheim: Wiley-VCH Verlag GmbH & Co. KGaA, Preface (2005).

Dykstra et al., "Selective Inhibition of Topoisomerases from Pneumocystis Carinii Compound with That of Topoisomerases from Mammalian Cells," Antimicrobial Agents and Chemotherapy. vol. 38, No. 9 pp. 1890-1898 (1994).

Ellingson et al., "Bromination of 2-amino-3-carbomethoxypyrazine," Journal of the American Chemical Society. vol. 71 pp. 2798-2800 (1949).

European Search Report corresponding to European Patent Application No. 06 011 533.4-1211 dated Oct. 6, 2006.

European Search Report corresponding to European Patent Application No. 08 150 205.6-1211 dated Jul. 2, 2008.

Fairlamb, "Chemotherapy of human African trypanosomiasis: current and future Prospects," Trends in Parasitology. vol. 19, No. 11 pp. 488-494 (2003).

Fitzgerald, D. J., and Anderson, J.N., "Selective Nucleotide Disruption by Drugs That Bind in the Minor Groove of DNA," The Journal of Biological Chemistry. vol. 274, No. 38 pp. 27128-27138 (1999).

Garner et al., "The Benefits of Artemisinin Combination Therapy for Malaria Extend Beyond the Individual Patient," PLoS Medicine. vol. 2, No. 4 pp. 0287-0288 (2005).

Hall et al., "Anti-*Pneumocystis* Activity of Aromatic Diamidoxine Prodrugs," Antimicrobial Agents and Chemotherapy. vol. 42, No. 3 pp. 666-674 (1998).

Henderson, D., and Hurley, L.H., "Molecular struggle for transcriptional control," Nature Medicine. vol. 1 pp. 525-527 (1995).

Hu et al., "Azaterphenyl Diamidines as Antileishmanial Agents," Bioorganic & Medicinal Chemistry Letters. vol. 18, No. 1 pp. 247-251 (2008).

Ismail et al. "Synthesis and Antiprotozoal Activity of Aza-Analogues of Furamidine," Journal of Medicinal Chemistry. vol. 46, No. 22 pp. 4761-4769 (2003).

Ismail et al., "Synthesis, DNA Affinity, and Antiprotozoal Activity of Linear Dications: Terphenyl Diamidines and Analogues," Journal of Medicinal Chemistry. vol. 49, No. 17 pp. 5324-5332 (2006).

Jampilek et al., "Novel regioselective preparation of 5-chloropyrazine-2-carbonitrile from pyrazine-2-carboxamide and coupling study of substituted phenylsulfanylpyrazine-2-carboxylic acid derivatives," Current Organic Chemistry. vol. 9, No. 1 pp. 49-60 (2005).

Jordan, Nature Reviews: Drug Discovery vol. 2 p. 205 (2003).

Kumar et al., "Palladium catalyzed cross-coupling reactions for the synthesis of 2,5-disubstituted furans," Heterocyclic Communications. vol. 5, No. 4 pp. 301-304 (1999).

Kumar et al., "Synthesis of dicationic diarylpyridines as nucleic-acid binding agents," European Journal of Medicinal Chemistry. vol. 30, No. 2 pp. 99-106 (1995).

Liebeskind, L.S., and Pena-Cabrera, E., "Stille Couplings Catalyzed by Palladium-on-Carbon with CuI as a Cocatalyst: Synthesis of 2-(4'-Acetylphenyl)thiopehene," Organic Syntheses, Coll. vol. 10 p. 9 (2004); vol. 77 p. 135 (2000).

Lim, "Growth and Control of Growth," Microbiology, 3$^{rd}$ Edition, McGraw-Hill Co., Chapter 5, pp. 122-161 (2003).

Mazur et al., "A Thermodynamic and Structural Analysis of DNA Minor-Groove Complex Formation," Journal of Molecular Biology. vol. 300 pp. 321-337 (2000).

Nguyen et al., "Characterization of a Novel DNA Minor-Groove Complex," Biophysical Journal. vol. 86 pp. 1028-1041 (2004).

Nguyen et al., "Strong Binding in the DNA Minor Groove by an Aromatic Diamidine with a Shape That Does Not Match the Curvature of the Groove," Journal of the American Chemical Society. vol. 124 pp. 13680-13681 (2002).

Noga, "Fish Disease: Diagnosis and Treatment," Wiley-Blackwell. pp. 123-126 (2000).

Notice of Allowance corresponding to U.S. Appl. No. 11/436,045 dated Aug. 31, 2011.

Notice of Allowance corresponding to U.S. Appl. No. 11/698,257 dated Feb. 14, 2011.

Official Action corresponding to European Patent Application No. 06 011 533.4-1211 dated Mar. 27, 2007.

Official Action corresponding to European Patent Application No. 06 011 533.4-1211 dated Mar. 26, 2009.

Official Action corresponding to European Patent Application No. 08 150 205.6-1211 dated Jan. 30, 2009.

Official Action corresponding to U.S. Appl. No. 11/436,045 dated Oct. 31, 2007.

Official Action corresponding to U.S. Appl. No. 11/436,045 dated Jan. 24, 2008.

Official Action corresponding to U.S. Appl. No. 11/436,045 dated Oct. 3, 2008.

Official Action corresponding to U.S. Appl. No. 11/436,045 dated Aug. 12, 2010.

Official Action corresponding to U.S. Appl. No. 11/436,045 dated Mar. 3, 2011.

Official Action corresponding to U.S. Appl. No. 11/698,257 dated May 12, 2008.

Official Action corresponding to U.S. Appl. No. 11/698,257 dated Nov. 26, 2008.

Official Action corresponding to U.S. Appl. No. 11/698,257 dated Jun. 11, 2009.

Official Action corresponding to U.S. Appl. No. 11/698,257 dated Dec. 10, 2009.

Official Action corresponding to U.S. Appl. No. 11/698,257 dated Oct. 26, 2010.

Published Patent Application corresponding to Chinese Patent Application No. 20081000859.2 dated Sep. 24, 2008.

Schmid, "10-Day Melarsoprol Treatment of *Trypanosoma brucei gambiense* Sleeping Sickness: From Efficacy to Effectiveness," Doctoral Dissertation. Universitat Basel (2004).

Shaikh et al., "A molecular thermodynamic view of DNA-drug interactions: a case study of 25 minor-groove binders," Archives of Biochemistry and Biophysics. vol. 429, No. 1 pp. 81-99 (2004).

Sheehan, J.C., and Hlavka, J.J., "The Use of Water-Soluble and Basic Carbodiimides in Peptide Synthesis," Journal of Organic Chemistry. vol. 21, No. 4 pp. 439-441 (1956).

Steck et al., "*Leishmania donovani, Plasmodium berghei, Trypanosoma rhodesiense*: Antiprotozoal Effects of Some AmidineTypes," Experimental Parasitology. vol. 52, No. 3 pp. 404-413 (1981).

Stephens et al., "The Activity of Diguanidino and 'Reversed' Diamidino 2,5-Diarylfurans versus *Trypanosoma cruzi* and *Leishmania donovani*," Bioorganic and Medicinal Chemistry Letters. vol. 13 pp. 2065-2069 (2003).

Tidwell, "Dicationic DNA Minor Groove Binders as Antimicrobial Agents," Small Molecule DNA and RNA Binders: From Synthesis to Nucleic Acid Complexes. vol. 2 pp. 414-460 (2003).

Wiles et al., "Biological evaluation of isothiazoloquinolones containing aromatic heterocycles at the 7-position: In vitro activity of a series of potent antibacterial agents that are effective against methicillin-resistant *Staphylococcus aureus*," Bioorganic & Medicinal Chemistry Letters. vol. 16, No. 5 pp. 1277-1281 (2006).

Wilson et al., "Nucleic Acid Interaction of Unfused Aromatic Cations: Evaluation of Proposed Minor-Groove, Major-Groove, and Intercalation Binding Modes," Journal of American Chemical Society. vol. 120, No. 40 pp. 10310-10321 (1998).

SUBSTITUTED PYRIDINES AS ANTIPARASITIC AZA TERARYL COMPOUNDS

CROSS REFERENCE TO RELATED APPLICATIONS

This application is a divisional application of U.S. patent application Ser. No. 11/698,257, filed Jan. 25, 2007, now U.S. Pat. No. 7,964,619 the disclosure of which is incorporated herein by reference in its entirety, which is a continuation-in-part of U.S. patent application Ser. No. 11/436,045, filed May 17, 2006, now U.S. Pat. No. 8,101,636 the disclosure of which is incorporated herein by reference in its entirety; which claims the benefit of and priority to U.S. Provisional Patent Application Ser. No. 60/687,092, filed Jun. 3, 2005, the disclosure of which is incorporated herein by reference in its entirety.

TECHNICAL FIELD

The presently disclosed subject matter relates to methods for combating microbial infections with novel dicationic terphenyl compounds and their aza analogues, processes for synthesizing novel dicationic terphenyl compounds and their aza analogues, and the novel dicationic terphenyl compounds and their aza analogues themselves.

ABBREVIATIONS

| | |
|---|---|
| δ = | chemical shift |
| Ac = | acetyl |
| AcO = | acetoxyl |
| AcOH = | acetic acid |
| Ac$_2$O = | acetic anhydride |
| Am = | amidine |
| AmOH = | amidoxime |
| Bu = | butyl |
| ° C. = | degrees Celsius |
| calcd = | calculated |
| cm = | centimeters |
| Cs$_2$CO$_3$ = | cesium carbonate |
| CT = | cytotoxicity |
| dec = | decomposition point |
| DIBAL = | diisobutylaluminium hydride |
| DMF = | dimethylformamide |
| DMSO = | dimethylsulfoxide |
| D$_2$O = | deuterium oxide |
| EtOAc = | ethyl acetate |
| EtOH = | ethanol |
| g = | grams |
| h = | hours |
| HAT = | human *African trypanosomiasis* |
| HCl = | hydrogen chloride or hydrochloric acid |
| HPLC = | high-pressure liquid chromatography |
| Hz = | hertz |
| ip = | intraperitoneal |
| kg = | kilograms |
| KO-t-Bu = | potassium tert-butoxide |
| L. d. = | *Leishmania donovani* |
| M = | molar |
| Me = | methyl |
| MeO = | methoxyl |
| MHz = | megahertz |
| mL = | milliliters |
| mm = | millimeters |
| mM = | millimolar |
| m.p. = | melting point |
| MS = | mass spectroscopy |
| Na$_2$CO$_3$ = | sodium carbonate |
| Na$_2$SO$_4$ = | sodium sulfate |
| NBS = | N-bromosuccinimide |
| NH$_2$OH•HCl = | hydroxylamine hydrochloride |
| NMR = | nuclear magnetic resonance |
| p = | para |
| Pd—C = | 10% palladium on carbon |
| Pd(PPh$_3$)$_4$ = | tetrakis(triphenylphosphine)palladium |
| P. f. = | *Plasmodium falciparum* |
| po = | oral |
| psi = | pounds per square inch |
| spp. = | species |
| T. b. r. = | *Trypanosoma brucei rhodesiense* |
| T. cruzi = | *Trypanosoma cruzi* |
| THF = | tetrahydrofuran |
| TLC = | thin-layer chromatography |
| TMS = | trimethylsilyl |
| UV = | ultraviolet |

BACKGROUND

The antimicrobial activity of aromatic diamidines was first reported in the 1930's. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460. Since that time dicationic molecules have received considerable attention as potential new therapeutic agents. Despite these efforts, pentamidine, first reported in 1942, see Ashley, J. N., et al., *J. Chem. Soc.*, 103-106, (1942), is the only compound from this class of molecules for which there has been significant human use. Pentamidine is currently used against primary stage human African trypanosomiasis (HAT), antimony-resistant leishmaniasis and also as a secondary drug for AIDS-related *P. carinii* pneumonia (PCP). See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460. Pentamidine, however, must be administered parenterally, and causes potentially severe side effects. Further, drug resistance among parasites is emerging. Thus, there continues to be a need for improvement in the art for additional compounds having desirable antimicrobial activity, whether against the representative pathogens referenced above or against other pathogens.

SUMMARY

In some embodiments, the presently disclosed subject matter provides a compound of Formula (I):

$$L_1\text{-Ar}_1\text{—(CH}_2)_p\text{—Ar}_2\text{—(CH}_2)_q\text{—Ar}_3\text{-}L_2 \quad (I)$$

wherein:

p and q are each independently an integer from 0 to 8;

Ar$_1$ and Ar$_3$ are independently selected from the group consisting of:

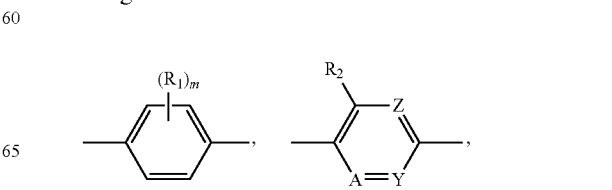

-continued

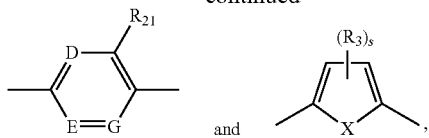
and wherein:

each A, D, E, G, Y, and Z is independently selected from the group consisting of N and $CR_4$, wherein $R_4$ is selected from the group consisting of H, hydroxyl, halo, nitro, alkyl, substituted alkyl, alkoxyl, aryl, substituted aryl, and aryloxyl;

X is selected from the group consisting of O, S, NH, and Se;

each m is independently an integer from 0 to 4;

each s is independently an integer from 0 to 2;

each $R_1$, $R_2$, $R_3$, and $R_{21}$ is independently selected from the group consisting of H, hydroxyl, halo, nitro, alkyl, substituted alkyl, alkoxyl, aryl, substituted aryl, and aryloxyl;

$Ar_2$ is selected from the group consisting of:

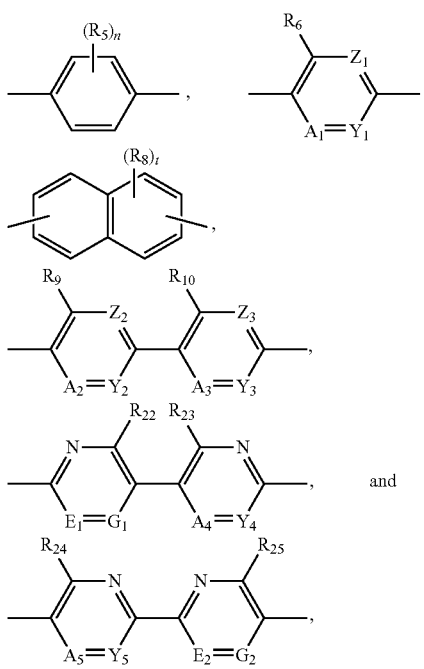

wherein:

$A_1, A_2, A_3, A_4, A_5, E_1, E_2, G_1, G_2, Y_1, Y_2, Y_3, Y_4, Y_5, Z_1, Z_2,$ and $Z_3$ are independently selected from the group consisting of N and $CR_7$, wherein $R_7$ is selected from the group consisting of H, hydroxyl, halo, nitro, alkyl, substituted alkyl, alkoxyl, aryl, substituted aryl, and aryloxyl;

n is an integer from 0 to 4;

t is an integer from 0 to 6;

each $R_5$, $R_6$, $R_8$, $R_9$, $R_{10}$, $R_{22}$, $R_{23}$, $R_{24}$, and $R_{25}$ is independently selected from the group consisting of H, hydroxyl, halo, nitro, alkyl, substituted alkyl, alkoxyl, aryl, substituted aryl, aryloxyl; and $L_1$ and $L_2$ are independently selected from the group consisting of:

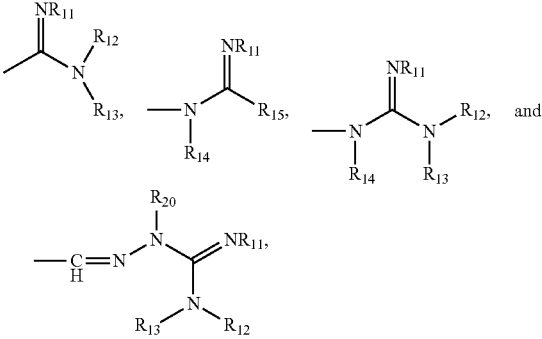

wherein:

$R_{11}$, $R_{12}$, $R_{13}$, $R_{14}$, $R_{15}$, and $R_{20}$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_{11}$ and $R_{12}$ together represent a $C_2$ to $C_{10}$ alkyl, $C_2$ to $C_{10}$ hydroxyalkyl, or a $C_2$ to $C_{10}$ alkylene; or $R_{11}$ and $R_{12}$ together are:

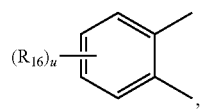

wherein u is an integer from 1 to 4, and $R_{16}$ is H or —$CONHR_{17}NR_{18}R_{19}$, wherein $R_{17}$ is alkyl, and $R_{18}$ and $R_{19}$ are each independently selected from the group consisting of H and alkyl;

or a pharmaceutically acceptable salt thereof.

In some embodiments, the compound is a compound of Formula (I) wherein at least one of $Ar_1$ and $Ar_3$ is

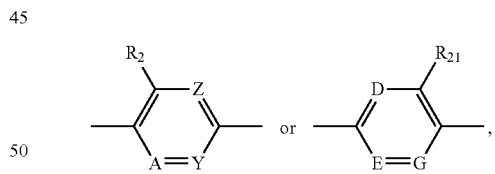

and at least one of A, D, E, G, Y, or Z is nitrogen wherein at least one of $L_1$ or $L_2$ is ortho to the at least one nitrogen A, D, E, G, Y, or Z.

In some embodiments, the presently disclosed subject matter provides a method for treating a microbial infection in a subject in need of treatment thereof, the method comprising administering to the subject an effective amount of a compound of Formula (I). In some embodiments, the infection is caused by one of the group selected from a *Trypanosoma* species, a *Plasmodium* species, and a *Leishamania* species. In some embodiments the infection is caused by one of the group selected from *Trypanosoma brucei rhodesiense*, *Plasmodium falciparum*, and *Leishmania donovoni*.

In some embodiments, the presently disclosed subject matter provides the use of an active compound as described hereinabove, i.e., a compound of Formula (I), for the preparation of a medicament for treating a microbial infection.

In some embodiments, the presently disclosed subject matter provides a pharmaceutical formulation comprising a compound of Formula (I).

In some embodiments, the presently disclosed subject matter provides a method for treating an infection caused by a *Leishmania* species in a subject in need of treatment thereof. In some embodiments, the method comprises administering to the subject an effective amount of an aza teraryl compound, wherein the compound has a structure selected from the group consisting of Formula (IIe) and Formula (IIh):

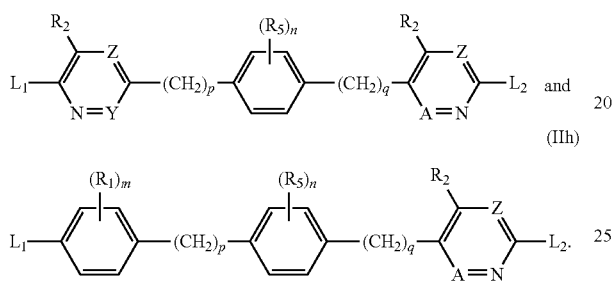

wherein:
p and q are each independently an integer from 0 to 8;
m is an integer from 0 to 4;
n is an integer from 0 to 4;
each Z, A, and Y is independently selected from the group consisting of N and $CR_4$, wherein $R_4$ is selected from the group consisting of H, hydroxyl, halo, nitro, alkyl, substituted alkyl, alkoxyl, aryl, substituted aryl, and aryloxyl;
each $R_1$, $R_2$ and $R_5$ is independently selected from the group consisting of H, hydroxyl, halo, nitro, alkyl, substituted alkyl, alkoxyl, aryl, substituted aryl, and aryloxyl; and
$L_1$ and $L_2$ are independently selected from the group consisting of:

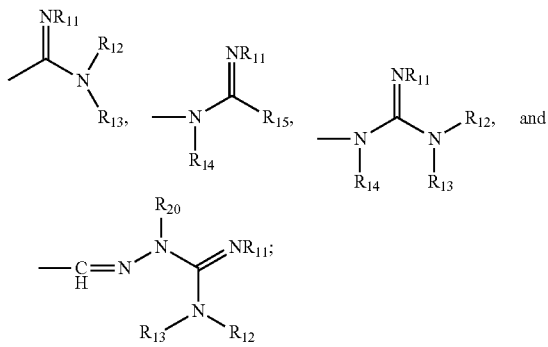

wherein:
$R_{11}$, $R_{12}$, $R_{13}$, $R_{14}$, $R_{15}$, and $R_{20}$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_{11}$ and $R_{12}$ together represent a $C_2$ to $C_{10}$ alkyl, $C_2$ to $C_{10}$ hydroxyalkyl, or a $C_2$ to $C_{10}$ alkylene; or
$R_{11}$ and $R_{12}$ together are:

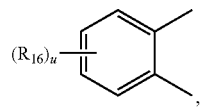

wherein u is an integer from 1 to 4, and $R_{16}$ is H or —$CONHR_{17}NR_{18}R_{19}$, wherein $R_{17}$ is alkyl, and $R_{18}$ and $R_{19}$ are each independently selected from the group consisting of H and alkyl; or
a pharmaceutically acceptable salt thereof.

In some embodiments, the compound is selected from the group consisting of:

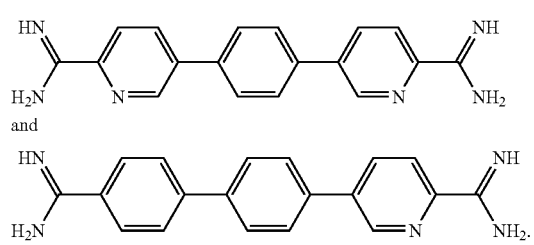

In some embodiments, the *Leishmania* species is *Leishmania donovani*. In some embodiments, the *Leishmania* species is *Leishmania mexicana amazonensis*.

It is accordingly an object of the presently disclosed subject matter to provide methods and compositions for treating microbial infections, such as, but not limited to, those caused by *Trypanosoma* species (spp.), including, but not limited to, *Trypanosoma brucei rhodesiense, Trypanosoma brucei gambiense, Trypanosoma brucei brucei*, and *Trypanosoma cruzi; Plasmodium* spp., including but not limited to *Plasmodium falciparum;* and *Leishmania* spp., including but not limited to *Leishmania donovani* and *Leishmania mexicana amazonensis*, in a subject in need thereof.

An object of the presently disclosed subject matter having been stated hereinabove, which are addressed in whole or in part by the presently disclosed subject matter, other objects and aspects will become evident as the description proceeds when taken in connection with the accompanying Examples as best described herein below.

DETAILED DESCRIPTION

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with one or more atoms or functional groups, including for example, alkyl, substituted alkyl, halogen, e.g., —$CH_2X$, —$CHX_2$, and —$CX_3$, wherein X is a halogen selected from the group consisting of Cl, Br, F, and I, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

As used herein, the term "teraryl" refers to a compound comprising at least three aryl groups. In some embodiments, the at least three aryl groups are directly attached to one another. The term "terphenyl" can refer to a compound comprising three benzene rings.

As used herein, the term "aza" refers to a heterocyclic ring structure containing at least one nitrogen atom. Specific examples of aza groups include, but are not limited to, pyrrolidine, piperidine, quinuclidine, pyridine, pyrrole, indole, purine, pyridazine, pyrimidine, and pyrazine.

A structure represented generally by a formula such as:

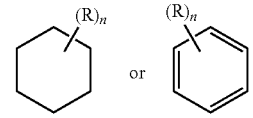

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure, replacing an H atom that would be bonded to that carbon in the absence of the R group. The presence or absence of the R group and the number of R groups is determined by the value of the integer n. Each R group, if more than one, is substituted on an available carbon of the ring structure rather than on another R group. For example, the structure:

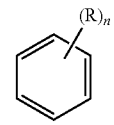

wherein n is an integer from 0 to 2 comprises compound groups including, but not limited to:

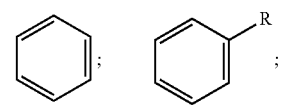

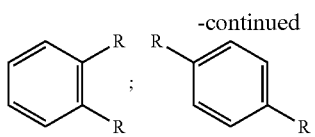

and the like.

In the case of a fused cyclic system, the R group may be substituted on any otherwise unsubstituted carbon through the fused system. Thus, the case of a napthyl group with the structure:

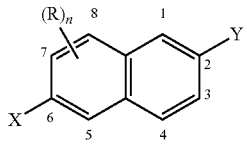

already substituted at carbons 2 and 6 by substituents X and Y, wherein n is one (1) comprises compound groups including:

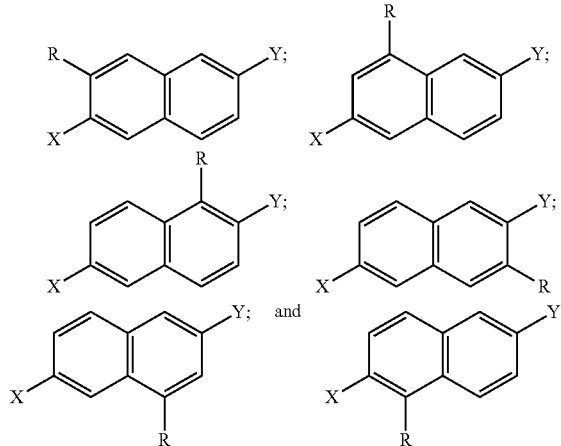

wherein the one (1) R substituent can be attached at any carbon on the naphthyl parent structure not occupied by another designated substituent, as in this case carbon 6 is substituted by X and carbon 2 is substituted by Y.

In some embodiments, the compounds described by the presently disclosed subject matter contain a linking group. As used herein, the term "linking group" comprises a chemical moiety, such as a alkylene, furanyl, phenylene, thienyl, and pyrrolyl radical, which is bonded to two or more other chemical moieties, in particular aryl groups, to form a stable structure.

The term "phenylene" refers to a bivalent organic radical, $C_6H_4$, derived from benzene by removal of two hydrogen atoms and which, in some embodiments, has a structure selected from the group consisting of:

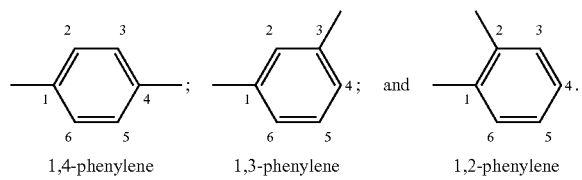

Thus, the term "phenylene" can refer to "1,4-phenylene," "1,3-phenylene," and "1,2-phenylene," respectively.

The term "furanyl" refers to a bivalent organic radical, $C_4H_2O$, derived from furan by removal of two hydrogens and which, in some embodiments, has a structure selected from the group consisting of:

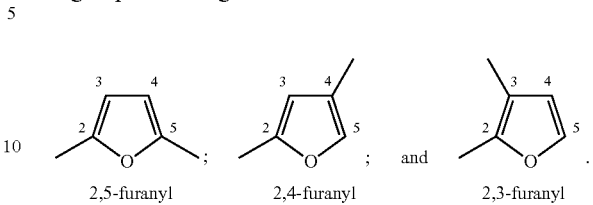

Thus, the term "furanyl" can refer to "2,5-furanyl," "2,4-furanyl," and "2,3-furanyl," respectively.

The term "naphthyl" refers to a bivalent organic radical, $C_{10}H_6$, derived from naphthalene by removal of two hydrogens and which, in some embodiments, has a structure selected from the group consisting of:

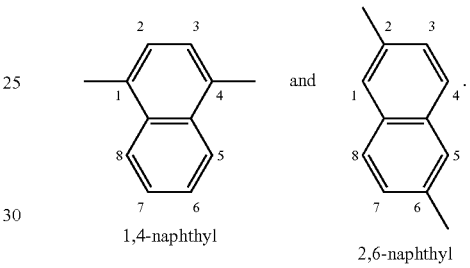

Thus, the term "naphthyl" can refer to "1,4-naphthyl," "2,6-naphthyl," and the like.

The term "ortho" refers to an aryl substitutent that is attached to the aryl group at a position directly adjacent to the reference position. For example, substituent R group can be referred to as ortho to the heteroaryl nitrogen atom in the pyrimidyl group:

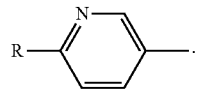

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

As used herein, the term "acyl" refers to an organic acid group wherein the —OH of the carboxyl group has been replaced with another substituent (i.e., as represented by RCO—, wherein R is an alkyl, substituted alkyl, aryl, or substituted aryl group as defined herein). In some embodiments, the term acyl can refer to the group RCO— wherein R is an amino-substituted alkyl group, an alkylamino-substituted alkyl group, a dialkylamino-substituted alkyl group, or a hydroxyl-substituted alkyl group. Thus, the term "acyl" can refer to groups such as H$_2$NR$_1$CO—, R$_2$HNR$_1$CO—, R$_3$R$_2$NR$_1$CO—, and HOR$_1$CO—, wherein R$_1$ is alkylene and R$_2$ and R$_3$ are lower alkyl. The term "acyl" also specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" or "alkoxyalkyl" refer to an alkyl-O— group wherein alkyl is as previously described. The term "alkoxyl" as used herein can refer to C$_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino. The term "alkylamino" refers to an —NHR group wherein R is an alkyl or substituted alkyl group.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H$_2$N—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

The term "amino" refers to the —NH$_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

When the term "independently selected" is used, the substituents being referred to (e.g., R groups, such as groups R$_1$ and R$_2$, or groups X and Y), can be identical or different. For example, both R$_1$ and R$_2$ can be substituted alkyls, or R$_1$ can be hydrogen and R$_2$ can be a substituted alkyl, and the like.

A named "R", "R'," "X," "Y," "A," "D," "E," "G," "L," or "Z" group will generally have the structure that is recognized in the art as corresponding to a group having that name, unless specified otherwise herein. For the purposes of illustration, certain representative "R," "X," "Y", "D," "E," "G," "L," and "A" groups as set forth above are defined below. These definitions are intended to supplement and illustrate, not preclude, the definitions that would be apparent to one of ordinary skill in the art upon review of the present disclosure.

The term "reflux" and grammatical derivations thereof refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "metal alkyl" refers to a compound of the general formula $MR_n$, wherein M is a metal atom, including, but not limited to aluminum, boron, magnesium, zinc, gallium, indium, antimony and related metals, R is an alkyl group as defined herein, and n is an integer. A representative metal alkyl is trimethylaluminum, abbreviated as $Al(CH_3)_3$ or $AlMe_3$.

The term "alkali metal alcoholate" refers to an alkali metal derivative of an alcohol having the general formula $M_aOR_n$, wherein $M_a$ is an alkali metal, such as lithium, sodium, or potassium, O is oxygen, R is an alkyl group as defined herein, and n is an integer. Representative alkali metal alcoholates include, but are not limited to, sodium methanolate, abbreviated as $NaOCH_3$ or NaOMe, and potassium butoxide, abbreviated as $KOC(CH_3)_3$.

The term "acid anhydride" refers to an anhydride of an organic acid and includes, but is not limited to acetic anhydride (($CH_3C\!=\!O)_2O$ or $Ac_2O$) and benzoic anhydride (($C_6H_5C\!=\!O)_2O$).

II. Novel Compounds

The structures of pentamidine (a), furamidine (b), CGP 40215A (c), 3,5-bis[4-(4,5-dihydro-1H-imidazol-2-yl)phenyl]pyridine (d), bis-4,4'-amidinobiphenyl (e), and bis-4,4'-amidinophenylethyne (f) are shown in Scheme A.

Scheme A. Structures of Representative Dicationic Antiprotozoan Agents.

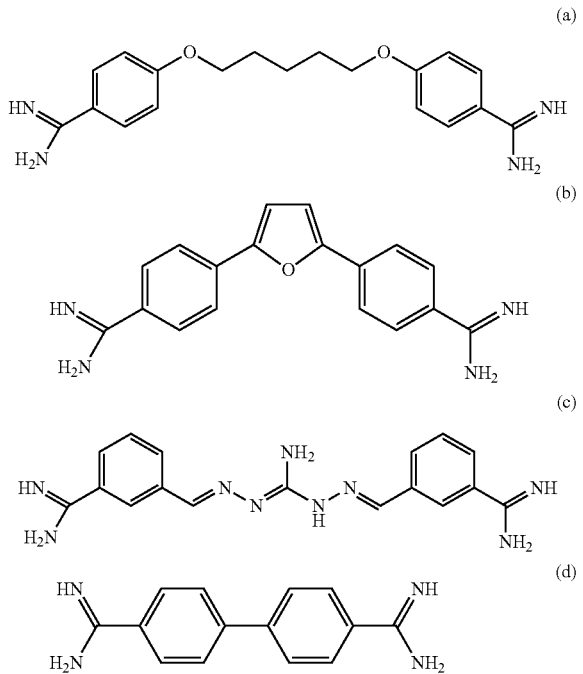

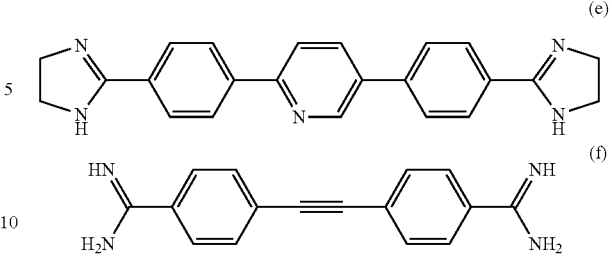

An orally effective prodrug of furamidine is currently in Phase II clinical trials against malaria, HAT and PCP. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460; Fairlamb, A. H., *Trends Parasitol.*, 19, 488-494 (2003); Bouteille, B., et al., *Fundam. Clin. Pharmacol.*, 17, 171-181 (2003). This type of dicationic molecule is thought to act by binding in the minor groove of DNA at AT rich sites, leading to inhibition of DNA dependant enzymes or possibly direct inhibition of transcription. Further, it has been postulated that minor groove binding leads to inhibition of DNA dependent enzymes or possibly direct inhibition of transcription. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460; Dykstra, C. C., et al., *Antimicrob. Agents Chemother.*, 38, 1890-1898 (1994); Bailly, C., et al., *Anti-Cancer Drug Design*, 14, 47-60 (1999); Fitzgerald, D. J. and J. N. Anderson, *J. Biol. Chem.*, 274, 27128-27138 (1999); Henderson, D. and L. H. Hurley, *Nature Med.*, 1, 525-527 (1995). Without wishing to be bound to any one particular theory, it is suggested that the selectivity of these molecules, at least for trypanosomes, likely includes a cell entry component involving amidine transporters.

An element in the design of new potential aromatic diamidine therapeutics has been that the molecular scaffold bearing the amidine units should present crescent shape geometry complimentary to the curve of the minor groove of DNA. See Corey, M., et al., *J. Med. Chem.*, 35; 431-438 (1992). Van der Waals contacts with the walls of the groove have been shown to be an important contributor to binding affinity. See Czarny, A. D., et al., *J. Am. Chem. Soc.*, 117, 4716 (1995); Mazur, S. F., et al., *J. Mol. Bio.*, 300, 321-337 (2000); Wilson, W. D., et al., *J. Am. Chem. Soc.*, 120, 10310-10321 (1998). A current theoretical analysis of the binding interactions of 25 minor groove binders shows that the small molecule curvature provides energetically favorable Van der Waals contacts. See Shaikh, S. A., et al., *Arch. Biochem. Biophys.*, 429, 81-99 (2004). Pentamidine, furamidine and many analogs meet this crescent shape profile. See Tidwell, R. R. and Boykin, D. W., Dicationic DNA Minor Groove Binders as Antimicrobial Agents, in *Small Molecule DNA and RNA Binders: From Synthesis to Nucleic Acid Complexes*, vol. 2, (M. Demeunynck, C. Bailly, and W. D. Wilson, ed., Wiley-VCH, New York, 2003), pp. 416-460; Cory, M., et al., *J. Med. Chem.*, 35, 431-438 (1992); Boykin, D. W., et al., *J. Med. Chem.*, 41, 124-129 (1998); Boykin, D. W., et al., *J. Med. Chem.*, 38, 912 (1995); Das, B. P. and Boykin, D. W., *J. Med. Chem.*, 20, 531 (1977). Further, it is thought that potent minor groove binders' solution structures either match the groove curve or easily assume low energy conformations that complement the groove on complex formation. Molecules that present too great or too small curvatures have difficulty in maximizing contacts with the minor groove and therefore typically exhibit reduced binding affinities. See Cory, M., et al., *J. Med. Chem.*, 35, 431-438 (1992).

The presently disclosed subject matter provides linear linking systems based on the terphenyl scaffold. Provided herein is the synthesis of novel teraryl dications, amidines, guanidines, and guanyl hydrazone and their evaluation as potential as minor groove binders and anti-protozoan agents.

II.A. Compounds of Formula (I)

Described herein is a compound of Formula (I):

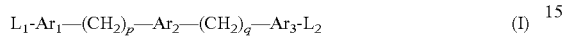

wherein:

p and q are each independently an integer from 0 to 8;

$Ar_1$ and $Ar_3$ are independently selected from the group consisting of:

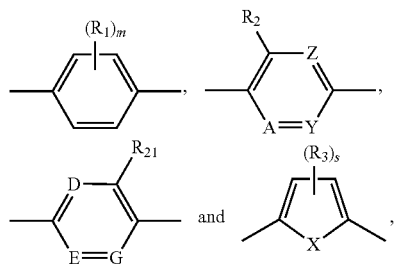

wherein:

each A, D, E, G, Y, and Z is independently selected from the group consisting of N and $CR_4$, wherein $R_4$ is selected from the group consisting of H, hydroxyl, halo, nitro, alkyl, substituted alkyl, alkoxyl, aryl, substituted aryl, and aryloxyl;

X is selected from the group consisting of O, S, NH, and Se;

each m is independently an integer from 0 to 4;

each s is independently an integer from 0 to 2;

each $R_1$, $R_2$, $R_3$, and $R_{21}$ is independently selected from the group consisting of H, hydroxyl, halo, nitro, alkyl, substituted alkyl, alkoxyl, aryl, substituted aryl, and aryloxyl;

$Ar_2$ is selected from the group consisting of:

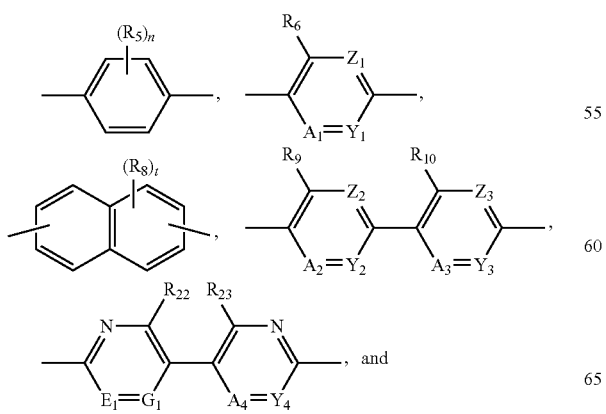

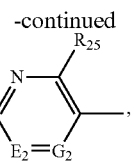

wherein:

$A_1, A_2, A_3, A_4, A_5, E_1, E_2, G_1, G_2, Y_1, Y_2, Y_3, Y_4, Y_5, Z_1, Z_2,$ and $Z_3$ are independently selected from the group consisting of N and $CR_7$, wherein $R_7$ is selected from the group consisting of H, hydroxyl, halo, nitro, alkyl, substituted alkyl, alkoxyl, aryl, substituted aryl, and aryloxyl;

n is an integer from 0 to 4;

t is an integer from 0 to 6;

each $R_5$, $R_6$, $R_8$, $R_9$, $R_{10}$, $R_{22}$, $R_{23}$, $R_{24}$, and $R_{25}$ is independently selected from the group consisting of H, hydroxyl, halo, nitro, alkyl, substituted alkyl, alkoxyl, aryl, substituted aryl, aryloxyl; and $L_1$ and $L_2$ are independently selected from the group consisting of:

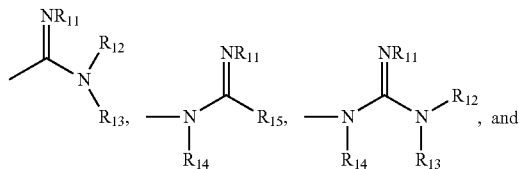

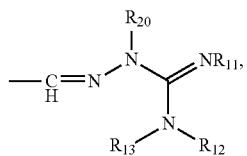

wherein:

$R_{11}$, $R_{12}$, $R_{13}$, $R_{14}$, $R_{15}$, and $R_{20}$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or $R_{11}$ and $R_{12}$ together represent a $C_2$ to $C_{10}$ alkyl, $C_2$ to $C_{10}$ hydroxyalkyl, or a $C_2$ to $C_{10}$ alkylene; or $R_{11}$ and $R_{12}$ together are:

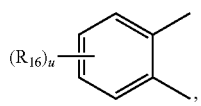

wherein u is an integer from 1 to 4, and $R_{16}$ is H or $-CONHR_{17}NR_{18}R_{19}$, wherein $R_{17}$ is alkyl, and $R_{18}$ and $R_{19}$ are each independently selected from the group consisting of H and alkyl;

or a pharmaceutically acceptable salt thereof.

In some embodiments, $Ar_2$ is phenylene and the compound of Formula (I) has the following structure:

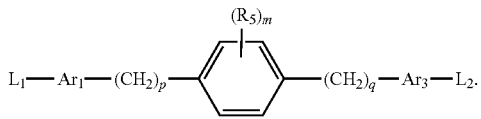
(II)

In some embodiments, $Ar_1$ is phenylene and $Ar_3$ is furanyl and the compound of Formula (II) has the following structure:

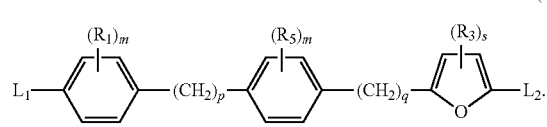
(IIa)

In some embodiments, $Ar_1$ and $Ar_3$ are each furanyl and the compound of Formula (II) has the following structure:

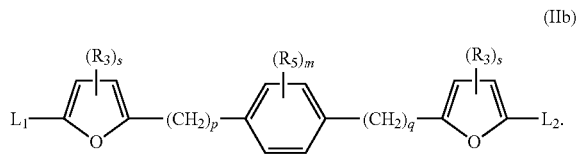
(IIb)

In some embodiments, $Ar_1$ and $Ar_3$ are each phenylene and the compound of Formula (II) has the following structure:

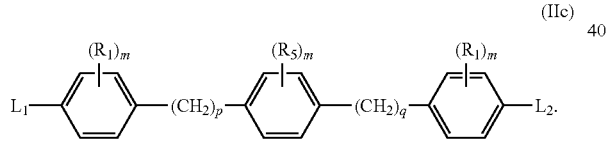
(IIc)

In some embodiments, $Ar_1$ and $Ar_3$ are each:

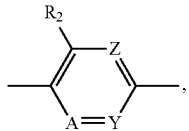

wherein at least one A and one Y are N, and the compound of Formula (II) has the following structure:

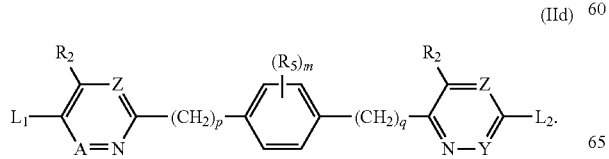
(IId)

In some embodiments, $Ar_1$ and $Ar_3$ are each:

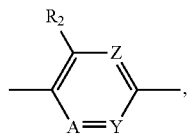

wherein at least one A and one Y are N, and the compound of Formula (II) has the following structure:

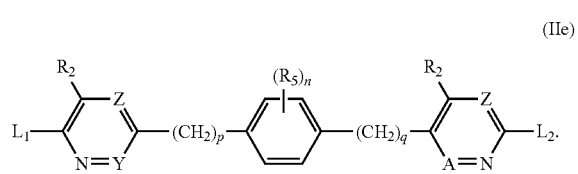
(IIe)

In some embodiments, $Ar_1$ is:

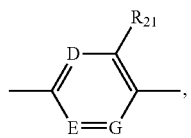

and $Ar_3$ is:

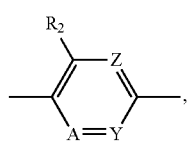

wherein the $Ar_1$ and $Ar_3$ aryl groups each comprise at least two nitrogen atoms. In some embodiments, A, D, G, and Z are each N, and the compound of Formula (II) has the following structure:

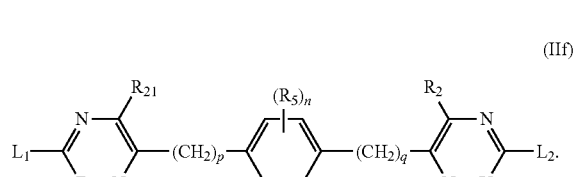
(IIf)

In some embodiments, $Ar_1$ is:

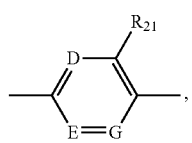

Ar₃ is:

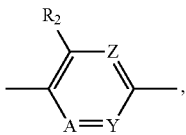

and D, E, Y and Z are each N, and the compound of Formula (II) has the following structure:

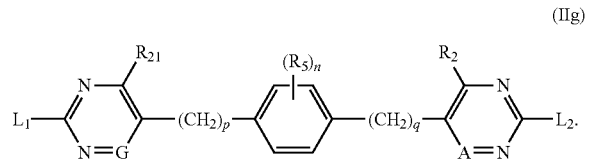
(IIg)

In some embodiments, Ar₁ is phenylene and Ar₃ is

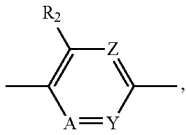

Y is N, and the compound of Formula (II) has the following structure:

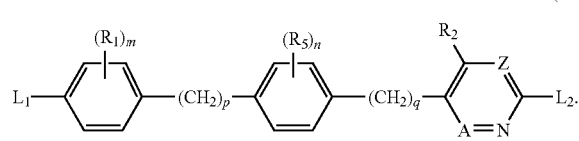
(IIh)

In some embodiments, Ar₁ is phenylene and Ar₃ is

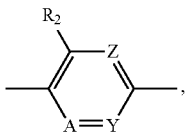

A is N, and the compound of Formula (II) has the following structure:

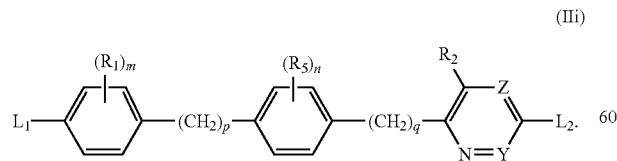
(IIi)

In some embodiments, a compound of Formula (II) is selected from the group consisting of:
N-Hydroxy-5-[4'-(N-hydroxyamidino)-biphenyl-4-yl]-furan-2--carboxamidine;
N-Methoxy-5-[4'-(N-methoxyamidino)-biphenyl-4-yl]-furan-2-carboxamidine;
5-[4'-Amidinobiphenyl-4-yl]-furan-2-carboxamidine;
N-Hydroxy-5-{4-[5-(N-hydroxyamidino)-furan-2-yl]-phenyl}-furan-2-carboxamidine;
5-[4-(5-amidinofuran-2-yl)-phenyl]-furan-2-carboxamidine;
[1,1';4',1"]Terphenyl-4,4"-bis-N-hydroxycarboxamidine;
[1,1';4',1"]Terphenyl-4,4"-bis-N-acetoxycarboxamidine;
[1,1';4',1"]Terphenyl-4,4"-bis-carboxamidine;
[1,1';4',1"]Terphenyl-4,4"-bis-N-methoxycarboxamidine;
2'-Fluoro-[1,1';4',1"]terphenyl-4,4"-bis-amidine;
2'-Fluoro-[1,1';4',1"]terphenyl-4,4"-bis-N-hydroxycarboxamidine;
2'-Fluoro-[1,1';4',1"]terphenyl-4,4"-bis-methoxycarboxamidine;
2'-Trifluoromethyl-[1,1';4',1"]terphenyl-4,4"-bis-amidine;
2'-Trifluoromethyl-[1,1';4',1"]terphenyl-4,4"-bis-N-hydroxycarbox-amidine;
2'-Trifluoromethyl-[1,1';4',1"]terphenyl-4,4"-bis-methoxycarboxamidine;
1,4-Bis-(5'-amidinopyridin-2'-yl)-phenylene;
1,4-Bis-[5'-N-hydroxyamidinopyridin-2'-yl)]-phenylene;
1,4-Bis-[5'-N-methoxyamidinopyridin-2'-yl)]-phenylene;
5-[4'-(Hydrazono)-biphenyl-4-yl]-furan-2-hydrazone;
5-{4'-[2-(4,5-Dihydro-1H-imidazol-2-yl)-hydrazono]-biphenyl-4-yl}-furan-2-(4,5-dihydro-1H-imidazol-2-yl)-hydrazone;
5-[4-(2-Hydrazono)-furan-5-yl-phenyl]-furan-2-hydrazone;
5-{4-[2-(4,5-Dihydro-1H-imidazol-2-yl)-hydrazono]-furan-5-yl-phenyl}-furan-2-(4,5-dihydro-1H-imidazol-2-yl)-hydrazone;
4,4"-Bis-guanidino-[1,1';4',1"]terphenyl;
4,4"-Bis(W-methyl)-guanidino-[1,1':4',1"]terphenyl;
4,4"-Bis(W-isopropyl-guanidino-[1,1';4',1"]terphenyl;
1,4-Bis-(5'-guanidinopyridin-2'-yl)phenylene;
1,4-Bis-{5'-[(N'-isopropyl)-guanidino]-pyridin-2'yl}phenylene;
1,4-Bis[4-amidinophenyl]-2,5-bis[methoxy]benzene;
1,4-Bis[5-(N-ethoxycarbonylguanidino)pyridin-2-yl]benzene;
1,4-Bis[5-(N-ethoxycarbonyl-N'-methylguanidino)pyridin-2-yl]benzene;
1,4-Bis[5-(N-methylguanidino)pyridin-2-yl]benzene;
1-[4-amidinophenyl]-4-[4-amidinobenzyl]benzene;
1,4-Bis-(2'amidinopyridin-5'yl)phenylene;
1,4-Bis-[2'-(N-hydroxyamidinopyridin-5' yl)]phenylene;
1,4-Bis-[2'-(N-methoxyamidinopyridin-5'-yl)]phenylene;
1,4-Bis-{2'-[N-(N',N'-dimethylaminoacetoxy)amidinopyridin-5'-yl]}phenylene;
1,4-Bis-(2'-amidinopyrazin-5'-yl)phenylene;
1,4-Bis-(2'-amidinopyrimidin-5'-yl)phenylene;
Phenyl[1,1']phenyl[4,5"]pyridinyl-4,2"-bis-amidine;
Phenyl[1,1']phenyl[4',5"]pyrimidinyl-4,2"-bis-amidine;
Phenyl[1,1]phenyl[4',2"]pyridinyl-4,5"-bis-amidine; and
a pharmaceutically acceptable salt thereof.

In some embodiments of the compound of Formula (I), Ar₂ is:

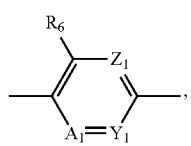

wherein at least one of $Z_1$, $A_1$, and $Y_1$ is N, and the compound of Formula (I) has the following structure:

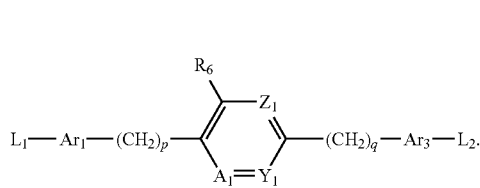
(III)

In some embodiments, $A_1$ is N and the compound of Formula (III) has the following structure:

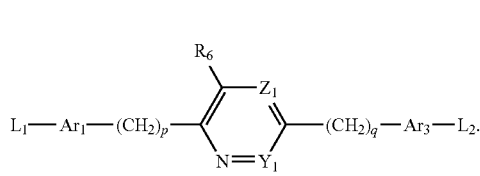
(IIIa)

In some embodiments, $Ar_1$ is phenylene, $Ar_3$ is furanyl, and the compound of Formula (IIIa) has the following structure:

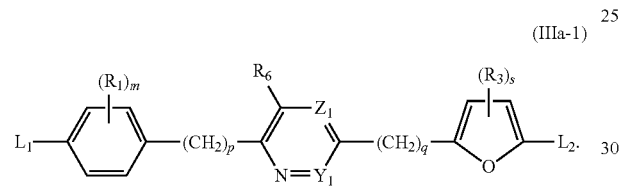
(IIIa-1)

In some embodiments, $Ar_1$ and $Ar_3$ are each phenylene, p is 0, and q is 1, and the compound of Formula (IIIa) has the following structure:

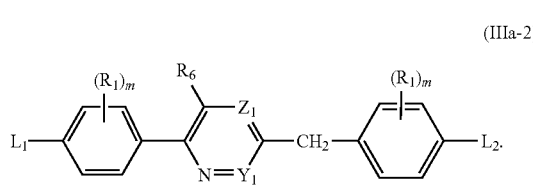
(IIIa-2)

In some embodiments, $Ar_1$ is phenylene and $Ar_3$ is:

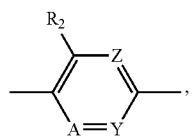

wherein A is N, and the compound of Formula (III) has the following structure:

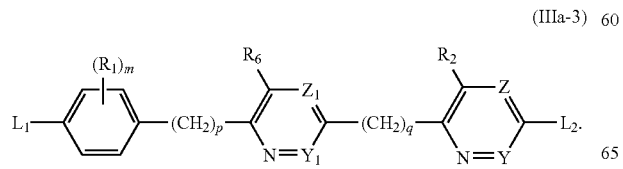
(IIIa-3)

In some embodiments, $Ar_1$ is phenylene and $Ar_3$ is:

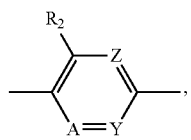

wherein Y is N, and the compound of Formula (III) has the following structure:

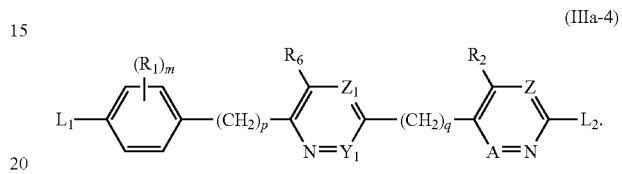
(IIIa-4)

In some embodiments, $Ar_1$ is phenylene and $Ar_3$ is:

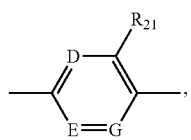

wherein D and G are each N, and the compound of Formula (III) has the following structure:

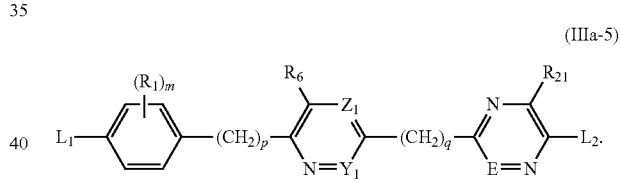
(IIIa-5)

In some embodiments, $Y_1$ is N and the compound of Formula (III) has the following structure:

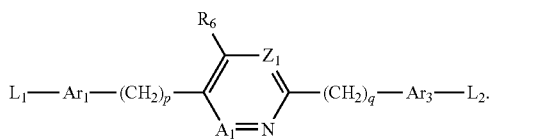
(IIIb)

In some embodiments, $Ar_1$ and $Ar_3$ are each phenylene and the compound of Formula (IIIb) has the following structure:

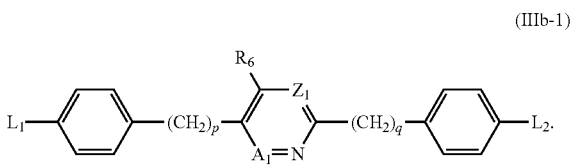
(IIIb-1)

In some embodiments, $Ar_1$ is phenylene and $Ar_3$ is furanyl and the compound of Formula (IIIb) has the following structure:

(IIIb-2)

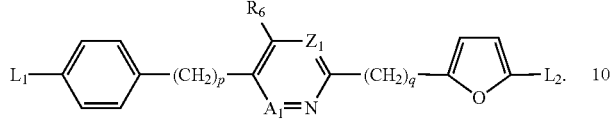

In some embodiments, $Z_1$ and $Y_1$ are each N and the compound of Formula (I) has the following structure:

(IIIc)

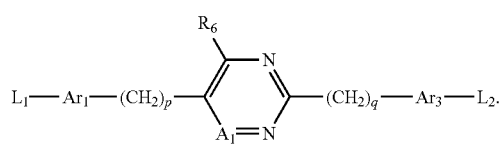

In some embodiments, $Ar_1$ and $Ar_3$ are each phenylene and the compound of Formula (IIIc) has the following structure:

(IIIc-1)

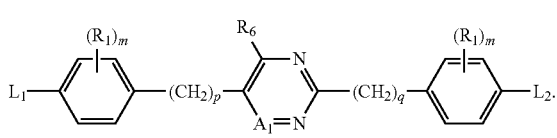

In some embodiments, $Ar_1$ is:

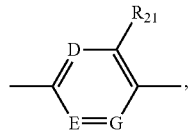

$Ar_3$ is:

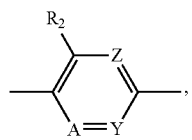

and E and Y are each N, and the compound of Formula (III) has the following structure:

(IIIc-2)

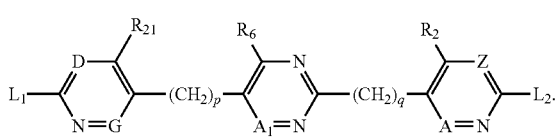

In some embodiments, $A_1$ and $Y_1$ are each N and the compound of Formula (III) has the following formula:

(IIId)

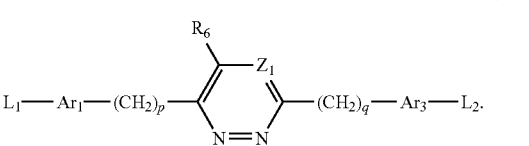

In some embodiments, $A_1$ and $Z_1$ are each N and the compound of Formula (III) has the following formula:

(IIIe)

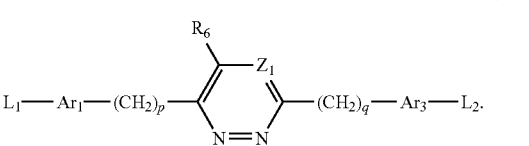

In some embodiments, the compound of Formula (III) is selected from the group consisting of:

N-Hydroxy-5-{6-[4-(N-hydroxyamidino)-phenyl]-pyridin-3-yl}-furan-2-carboxamidine;
5-[6-(4-Amidinophenyl)-pyridin-3-yl]-furan-2-carboxamidine;
Phenyl[1,1']pyridyl[4',1"]phenyl-4,4"-bis-carboxamidine;
Phenyl[1,1']pyridyl[4',1"]phenyl-4,4"-bis-N-hydroxycarbox-amidine;
Phenyl[1,1']pyridyl[4',1"]phenyl-4,4"-bis-N-methoxycarbox-amidine;
2-[4-(N-Hydroxyamidino)phenyl]-5-[4"-(N-hydroxyamidino)-benzyl]pyridine;
2-(4-Amidinophenyl)-5-(4"-amidinobenzyl)pyridine;
5-[4-(2-Hydrazono)-pyridin-5-yl-phenyl]-furan-2-hydrazone;
5-{4-[2-(4,5-Dihydro-1H-imidazol-2-yl)-hydrazono]-pyridin-5-yl-phenyl}-furan-2-(4,5-dihydro-1H-imidazol-2-yl)-hydrazone;
5-{4-[5-(4,5-Dihydro-1H-imidazol-2-yl)-hydrazono]-pyridin-2-yl-phenyl}-furan-2-(4,5-dihydro-1H-imidazol-2-yl)-hydrazone;
2,5-Bis-(4'-amidinophenyl)-pyrimidine;
2,5-Bis-[4'-(N-hydroxyamidino)phenyl]-pyrimidine;
2,5-Bis-[4'-(N-methoxyamidino)phenyl]-pyrimidine;
3,6-Bis[4-amidinophenyl]pyridazine;
3,6-Bis[4-N-hydroxyamidinophenyl]pyridazine;
3,6-Bis[4-N-methoxyamidinophenyl]pyridazine;
2,5-Bis-(4'-amidinophenyl)pyrazine;
2,5-Bis-(2'-amidinopyridin-5'-yl)pyrimidine;
Phenyl[1,2']pyridinyl[5',5"]pyridinyl-4,2"-bis-amidine;
Phenyl[1,2']pyridinyl[5',5"]pyridinyl-4,2"-bis-N-hydroxyamidine;
Phenyl[1,2']pyridinyl[5',5"]pyridinyl-4,2"-bis-N-methoxyamidine;
Phenyl[1,2']pyridinyl[5',2"]pyridinyl-4,5"-bis-amidine;
Phenyl[1,2']pyridinyl[5',5"]pyrazinyl-4,2"-bis-amidine;
Phenyl[1,2']pyridinyl[5',5"]pyrimidinyl-4,2"-bis-amidine; and
a pharmaceutically acceptable salt thereof.

In some embodiments of the compound of Formula (I), $Ar_2$ is napthyl and the compound of Formula (I) has the following structure:

(IV)

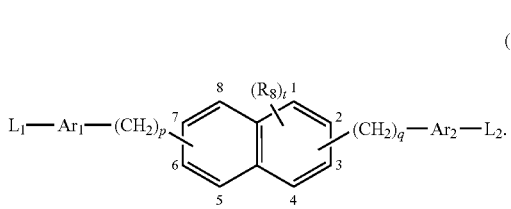

In some embodiments, $Ar_1$ and $Ar_3$ are each phenylene and the compound of Formula (IV) has the following structure:

(IVa)

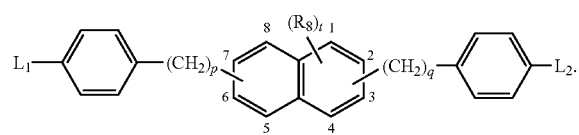

In some embodiments, the naphthyl group is substituted in the 1 and 4 positions and the compound of Formula (IVa) has the following structure:

(IVa-1)

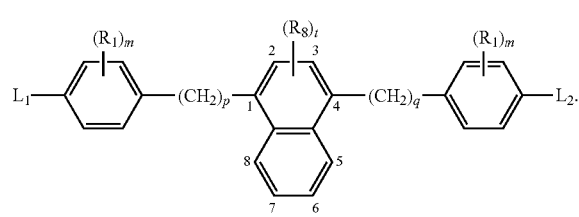

In some embodiments, the naphthyl group is substituted in the 2 and 6 positions and the compound of Formula (IVa) has the following structure:

(IVa-2)

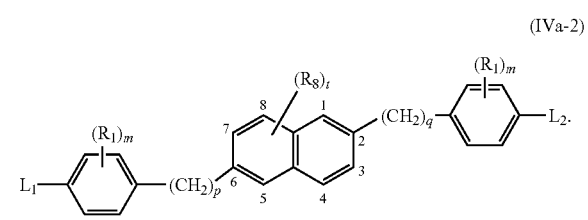

In some embodiments, the compound of Formula (I) is selected from the group consisting of:

Phenyl[1,1']napthyl[4',1'']phenyl-4,4''-bis-amidine;
Phenyl[1,1']napthyl[4',1'']phenyl-4,4''-bis-N-hydroxycarbox-amidine;
Phenyl[1,1']napthyl[4',1'']phenyl-4,4''-bis-N-methoxycarbox-amidine;
Phenyl[1,2']napthyl[6',1'']phenyl-4,4''-bis-amidine; and
a pharmaceutically acceptable salt thereof.

In some embodiments of the compound of Formula (I), $Ar_2$ is:

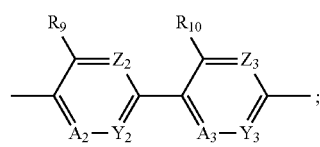

and the compound of Formula (I) has the following formula:

(V)

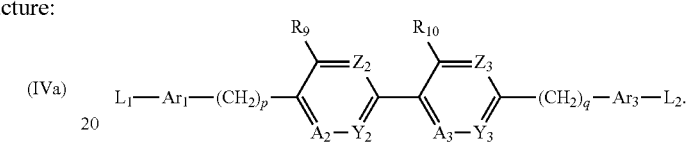

In some embodiments, $A_2$ and $Y_3$ are each N and the compound of Formula (V) has the following formula:

(Va)

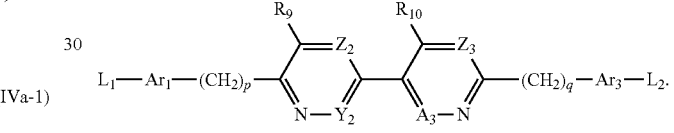

In some embodiments, $Ar_1$ and $Ar_3$ are each phenylene and the compound of Formula (Va) has the following formula:

(Va-1)

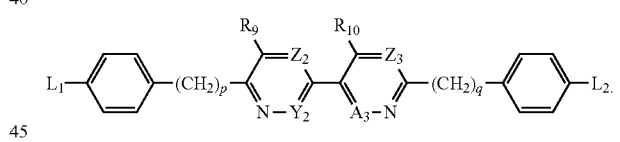

In some embodiments of the compounds of Formula (I-V), $L_1$ and $L_2$ are each:

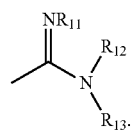

In some embodiments of the compounds of Formula (I-V), $L_1$ and $L_2$ are each:

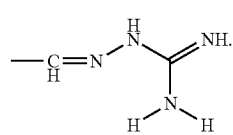

In some embodiments of the compounds of Formula (I-V), $L_1$ and $L_2$ are each:

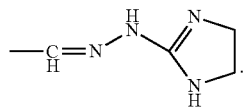

In some embodiments, the compound of Formula (I-V) comprises a pharmaceutically acceptable salt. In some embodiments, the pharmaceutically acceptable salt comprises a hydrochloride salt. In some embodiments, the pharmaceutically acceptable salt comprises an acetate salt.

II.B. Prodrugs

In representative embodiments, compounds disclosed herein are prodrugs. A prodrug means a compound that, upon administration to a recipient, is capable of providing (directly or indirectly) a compound of the presently disclosed subject matter or an inhibitorily active metabolite or residue thereof. Prodrugs can increase the bioavailability of the compounds of the presently disclosed subject matter when such compounds are administered to a subject (e.g., by allowing an orally administered compound to be more readily absorbed into the blood) or can enhance delivery of the parent compound to a biological compartment (e.g., the brain or lymphatic system) relative to a metabolite species, for example. A number of the compounds (e.g., Compounds 18, 21, 24a, 25a, 24b, 25b, 50a, 50b, 50c, 57b, 57c, 57a, 24c, 25c, 67, 68, 33, 29, 3, 4, 67, 68, 69, 90 and 91) disclosed herein are prodrugs.

II.C. Pharmaceutically Acceptable Salts

Additionally, the active compounds as described herein can be administered as a pharmaceutically acceptable salt. Such pharmaceutically acceptable salts include the gluconate, lactate, acetate, tartarate, citrate, phosphate, borate, nitrate, sulfate, and hydrochloride salts. The salts of the compounds described herein can be prepared, for example, by reacting two equivalents of the base compound with the desired acid in solution. After the reaction is complete, the salts are crystallized from solution by the addition of an appropriate amount of solvent in which the salt is insoluble. In some embodiments, as described in more detail herein below, the hydrochloride salt of an amidoxime compound is made by passing hydrogen chloride gas into an ethanolic solution of the free base. In some embodiments, as described in more detail herein below, the acetate salt of the presently disclosed diamidine compounds and/or the corresponding N-methoxy analogues are made directly from the appropriate N-hydroxy analogue. Accordingly, in some embodiments, the pharmaceutically acceptable salt is a hydrochloride salt. In some embodiments, the pharmaceutically acceptable salt is an acetate salt.

III. Pharmaceutical Formulations

The compounds of Formula (I-V), the pharmaceutically acceptable salts thereof, prodrugs corresponding to compounds of Formula (I-V), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations for administration, for example, as by intravenous or intramuscular injection.

The therapeutically effective dosage of any specific active compound, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the present methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments, provided herein. The pharmaceutical formulations comprise a compound of Formula (I-V) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formula (I-V) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I-V), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

IV. Methods for Treating Microbial Infections

Subjects with microbial infections can be treated by methods described herein. Such infections can be caused by a variety of microbes, including fungi, algae, protozoa, bacteria, and viruses. Exemplary microbial infections that can be treated by the method of the presently disclosed subject matter include, but are not limited to, infections caused by *Trypanosoma* spp. (e.g., *Trypanosoma brucei rhodesiense*, *Trypanosoma brucei gambiense*, *Trypanosoma brucei brucei*, and *Trypanosoma cruzi*), *Plasmodium* spp. (e.g.; *Plasmodium falciparum*), *Mycobacterium tuberculosis*, *Pneumocystis carinii*, *Giardia lamblia*, *Cryptosporidium parvum*, *Cryptococcus neoformans*, *Candida albicans*, *Candida tropicalis*, *Salmonella typhimurium*, *Leishmania donovani*, and *Leishmania mexicana amazonensis*. As used herein the terms *Trypanosoma* spp., *Plasmodium* spp., and *Leishmania* spp. encompass microbes classified under the genera *Trypanosoma*, *Plasmodium*, and *Leishmania* respectively.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat," "treating," and grammatical variations thereof, as well as the phrase "method of treating," are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

The methods for treating microbial infections comprise administering to a subject in need thereof an active compound as described herein. These active compounds, as set forth above, include compounds of Formula (I-V), their corresponding prodrugs, and pharmaceutically acceptable salts of the compounds and prodrugs.

With regard to the presently described method embodiments, compounds of Formula (I) can be defined as having a structure as follows:

$$L_1\text{-}Ar_1\text{—}(CH_2)_p\text{—}Ar_2\text{—}(CH_2)_q\text{—}Ar_3\text{-}L_2 \qquad (I)$$

wherein:

p and q are each independently an integer from 0 to 8;

$Ar_1$ and $Ar_3$ are independently selected from the group consisting of:

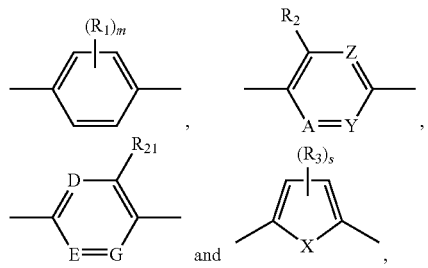

wherein:
each A, D, E, G, Y, and Z is independently selected from the group consisting of N and $CR_4$, wherein $R_4$ is selected from the group consisting of H, hydroxyl, halo, nitro, alkyl, substituted alkyl, alkoxyl, aryl, substituted aryl, and aryloxyl;
X is selected from the group consisting of O, S, NH, and Se;
each m is independently an integer from 0 to 4;
each s is independently an integer from 0 to 2;
each $R_1$, $R_2$, $R_3$, and $R_{21}$ is independently selected from the group consisting of H, hydroxyl, halo, nitro, alkyl, substituted alkyl, alkoxyl, aryl, substituted aryl, and aryloxyl;
$Ar_2$ is selected from the group consisting of:

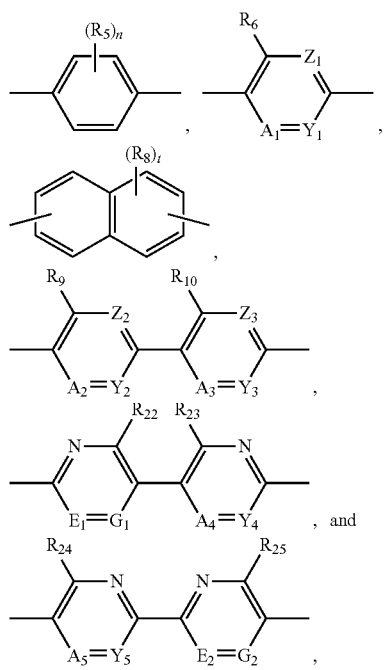

wherein:
$A_1, A_2, A_3, A_4, A_5, E_1, E_2, G_1, G_2, Y_1, Y_2, Y_3, Y_4, Y_5, Z_1, Z_2,$ and $Z_3$ are independently selected from the group consisting of N and $CR_7$, wherein $R_7$ is selected from the group consisting of H, hydroxyl, halo, nitro, alkyl, substituted alkyl, alkoxyl, aryl, substituted aryl, and aryloxyl;
n is an integer from 0 to 4;
t is an integer from 0 to 6;

each $R_5$, $R_6$, $R_8$, $R_9$, $R_{10}$, $R_{22}$, $R_{23}$, $R_{24}$, and $R_{25}$ is independently selected from the group consisting of H, hydroxyl, halo, nitro, alkyl, substituted alkyl, alkoxyl, aryl, substituted aryl, aryloxyl; and
$L_1$ and $L_2$ are independently selected from the group consisting of:

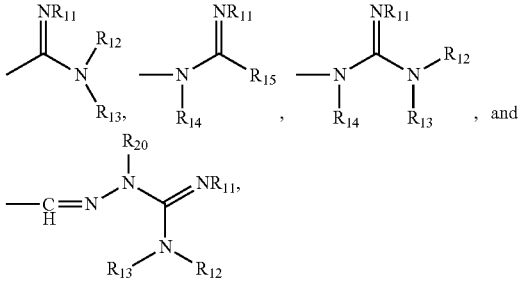

wherein:
$R_{11}$, $R_{12}$, $R_{13}$, $R_{14}$, $R_{15}$, and $R_{20}$ are each independently selected from the group consisting of H, alkyl, substituted alkyl, cycloalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl; or
$R_{11}$ and $R_{12}$ together represent a $C_2$ to $C_{10}$ alkyl, $C_2$ to $C_{10}$ hydroxyalkyl, or a $C_2$ to $C_{10}$ alkylene; or
$R_{11}$ and $R_{12}$ together are:

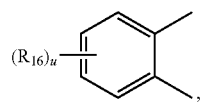

wherein u is an integer from 1 to 4, and $R_{16}$ is H or —$CONHR_{17}NR_{18}R_{19}$, wherein $R_{17}$ is alkyl, and $R_{18}$ and $R_{19}$ are each independently selected from the group consisting of H and alkyl;

or a pharmaceutically acceptable salt thereof.

In some embodiments, $Ar_2$ is phenylene and the compound of Formula (I) has the following structure:

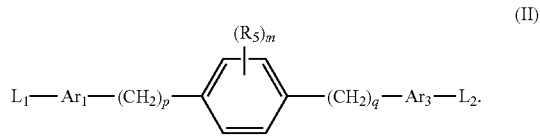

(II)

In some embodiments, $Ar_1$ is phenylene and $Ar_3$ is furanyl and the compound of Formula (II) has the following structure:

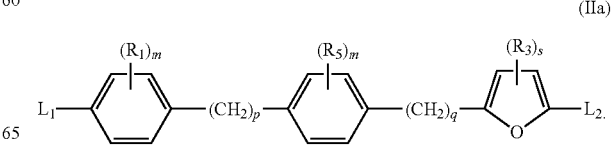

(IIa)

In some embodiments, Ar$_1$ and Ar$_3$ are each furanyl and the compound of Formula (II) has the following structure:

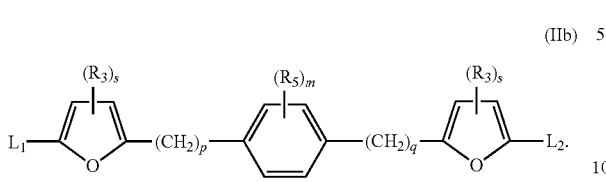
(IIb)

In some embodiments, Ar$_1$ and Ar$_3$ are each phenylene and the compound of Formula (II) has the following structure:

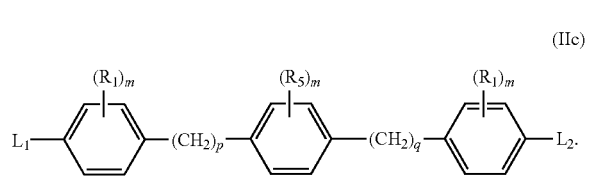
(IIc)

In some embodiments, Ar$_1$ and Ar$_3$ are each:

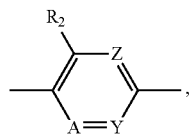

wherein at least one A and one Y are N, and the compound of Formula (II) has the following structure:

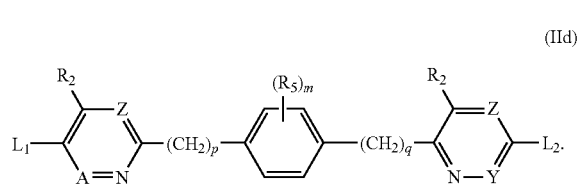
(IId)

In some embodiments, Ar$_1$ and Ar$_3$ are each:

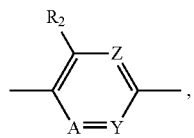

wherein at least one A and one Y are N, and the compound of Formula (II) has the following structure:

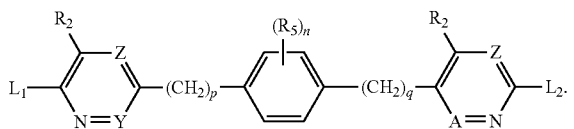
(IIe)

In some embodiments, Ar$_1$ is:

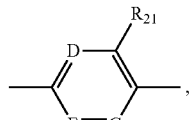

and Ar$_3$ is:

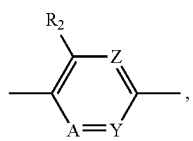

wherein the Ar$_1$ and Ar$_3$ aryl groups each comprise at least two nitrogen atoms. In some embodiments, A, D, G, and Z are each N, and the compound of Formula (II) has the following structure:

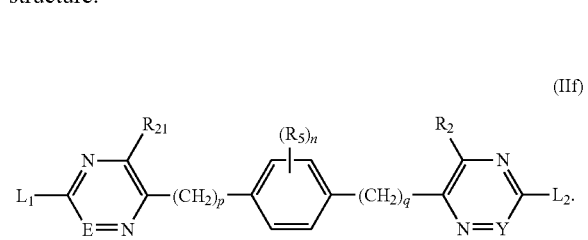
(IIf)

In some embodiments, Ar$_1$ is:

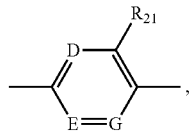

Ar$_3$ is:

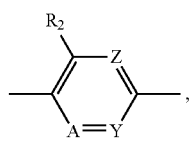

and D, E, Y and Z are each N, and the compound of Formula (II) has the following structure:

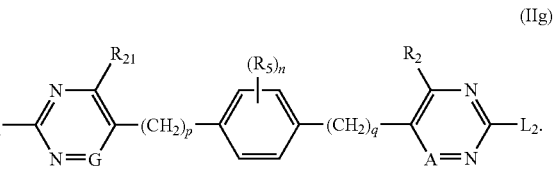
(IIg)

In some embodiments, $Ar_1$ is phenylene and $Ar_3$ is

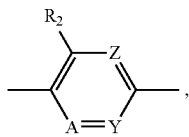

wherein Y is N, and the compound of Formula (II) has the following structure:

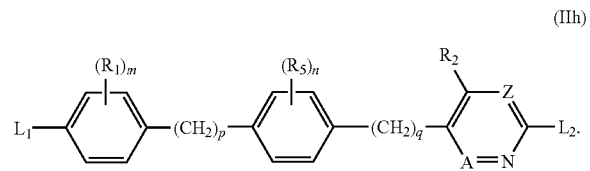

(IIh)

In some embodiments, $Ar_1$ is phenylene and $Ar_3$ is

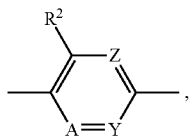

wherein A is N, and the compound of Formula (II) has the following structure:

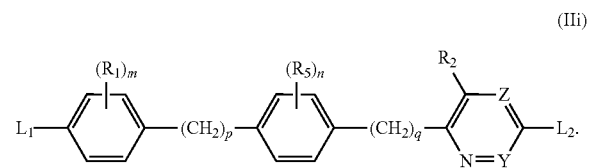

(IIi)

In some embodiments, a compound of Formula (II) is selected from the group consisting of:
N-Hydroxy-5-[4'-(N-hydroxyamidino)-biphenyl-4-yl]-furan-2-carboxamidine;
N-Methoxy-5-[4'-(N-methoxyamidino)-biphenyl-4-yl]-furan-2-carboxamidine;
5-[4'-Amidinobiphenyl-4-yl]-furan-2-carboxamidine;
N-Hydroxy-5-{4-[5-(N-hydroxyamidino)-furan-2-yl]-phenyl}-furan-2-carboxamidine;
5-[4-(5-amidinofuran-2-yl)-phenyl]-furan-2-carboxamidine;
[1,1';4',1"]Terphenyl-4,4"-bis-N-hydroxycarboxamidine;
[1,1';4',1"]Terphenyl-4,4"-bis-N-acetoxycarboxamidine;
[1,1';4',1"]Terphenyl-4,4"-bis-carboxamidine;
[1,1';4',1"]Terphenyl-4,4"-bis-N-methoxycarboxamidine;
2'-Fluoro-[1,1';4',1"]terphenyl-4,4"-bis-amidine;
2'-Fluoro-[1,1';4',1"]terphenyl-4,4"-bis-N-hydroxycarboxamidine;
2'-Fluoro-[1,1';4',1"]terphenyl-4,4"-bis-methoxycarboxamidine;
2'-Trifluoromethyl-[4',1';4',1"]terphenyl-4,4"-bis-amidine;
2'-Trifluoromethyl-[1,1';4',1"]terphenyl-4,4"-bis-N-hydroxycarbox-amidine;
2'-Trifluoromethyl-[1,1';4',1"]terphenyl-4,4"-bis-methoxycarboxamidine;
1,4-Bis-(5'-amidinopyridin-2'-yl)-phenylene;
1,4-Bis-[5'-N-hydroxyamidinopyridin-2'-yl)]-phenylene;
1,4-Bis-[5'-N-methoxyamidinopyridin-2'-yl)]-phenylene;
5-[4'-(Hydrazono)-biphenyl-4-yl]-furan-2-hydrazone;
5-{4'-[2-(4,5-Dihydro-1H-imidazol-2-yl)-hydrazono]-biphenyl-4-yl}-furan-2-(4,5-dihydro-1'-1-imidazol-2-yl)-hydrazone;
5-[4-(2-Hydrazono)-furan-5-yl-phenyl]-furan-2-hydrazone;
5-{4-[2-(4,5-Dihydro-1H-imidazol-2-yl)-hydrazono]-furan-5-yl-phenyl}-furan-2-(4,5-dihydro-1H-imidazol-2-yl)-hydrazone;
4,4"-Bis-guanidino-[1,1';4',1"]terphenyl;
4,4"-Bis(N'-methyl)-guanidino-[1,1';4',1"]terphenyl;
4,4"-Bis(N'-isopropyl-guanidino-[1,1';4',1"]terphenyl;
1,4-Bis-(5'-guanidinopyridin-2'-yl)phenylene;
1,4-Bis-{5'-[(N'-isopropyl)-guanidino]-pyridin-2'yl}phenylene;
1,4-Bis[4-amidinophenyl]-2,5-bis[methoxy]benzene;
1,4-Bis[5-(N-ethoxycarbonylguanidino)pyridin-2-yl]benzene;
1,4-Bis[5-(N-ethoxycarbonyl-N'-methylguanidino)pyridin-2-yl]benzene;
1,4-Bis[5-(N-methylguanidino)pyridin-2-yl]benzene;
1-[4-amidinophenyl]-4-[4-amidinobenzyl]benzene;
1,4-Bis-(2'amidinopyridin-5'yl)phenylene;
1,4-Bis-[2'-(N-hydroxyamidinopyridin-5'yl)]phenylene;
1,4-Bis-[2'-(N-methoxyamidinopyridin-5'-yl)]phenylene;
1,4-Bis-{2'-[N-(N',N'-dimethylaminoacetoxy)amidinopyridin-5'-yl]}phenylene;
1,4-Bis-(2'-amidinopyrazin-5'yl)phenylene;
1,4-Bis-(2'-amidinopyrimidin-5'yl)phenylene;
Phenyl[1,1']phenyl[4,5"]pyridinyl-4,2"-bis-amidine;
Phenyl[1,1']phenyl[4',5"]pyrimidinyl-4,2"-bis-amidine;
Phenyl[1,1]phenyl[4',2"]pyridinyl-4,5"-bis-amidine; and
a pharmaceutically acceptable salt thereof.

In some embodiments of the compound of Formula (I), $Ar_2$ is:

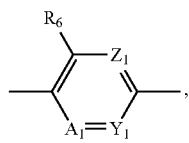

wherein at least one of $Z_1$, $A_1$, and $Y_1$ is N, and the compound of Formula (I) has the following structure:

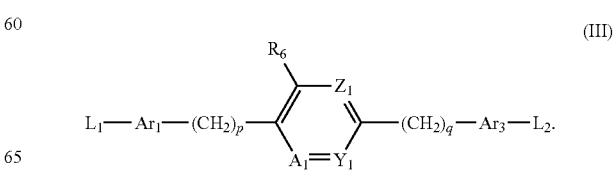

(III)

In some embodiments, $A_1$ is N and the compound of Formula (III) has the following structure:

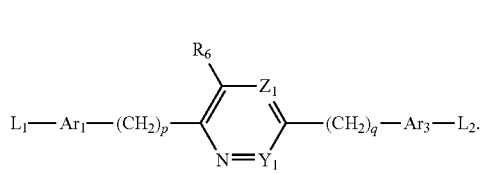
(IIIa)

In some embodiments, $Ar_1$ is phenylene, $Ar_3$ is furanyl, and the compound of Formula (IIIa) has the following structure:

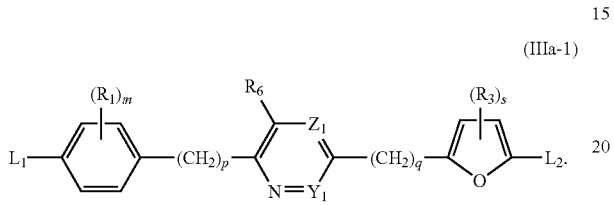
(IIIa-1)

In some embodiments, $Ar_1$ and $Ar_3$ are each phenylene, p is 0, and q is 1, and the compound of Formula (IIIa) has the following structure:

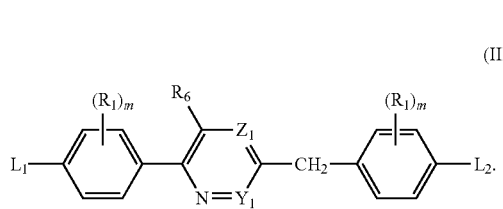
(IIIa-2)

In some embodiments, $Ar_1$ is phenylene and $Ar_3$ is:

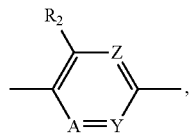

wherein A is N, and the compound of Formula (III) has the following structure:

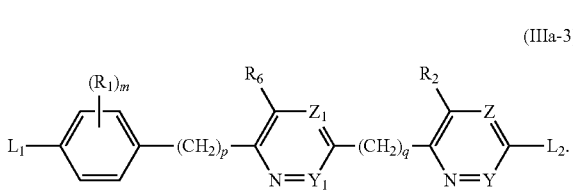
(IIIa-3)

In some embodiments, $Ar_1$ is phenylene and $Ar_3$ is:

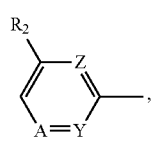

wherein Y is N, and the compound of Formula (III) has the following structure:

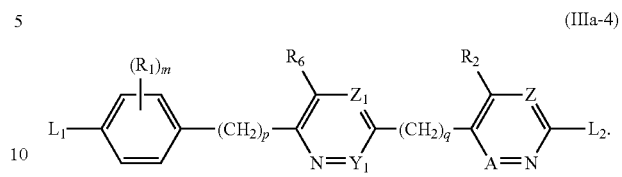
(IIIa-4)

In some embodiments, $Ar_1$ is phenylene and $Ar_3$ is:

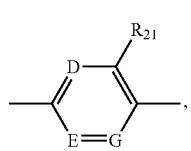

wherein D and G are each N, and the compound of Formula (III) has the following structure:

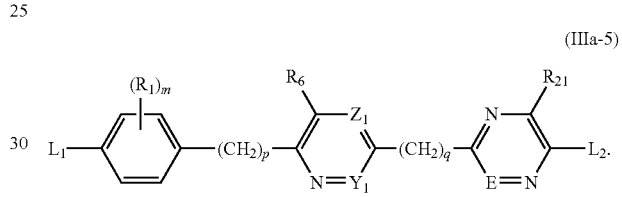
(IIIa-5)

In some embodiments, $Y_1$ is N and the compound of Formula (III) has the following structure:

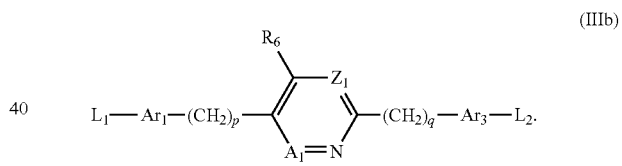
(IIIb)

In some embodiments, $Ar_1$ and $Ar_3$ are each phenylene and the compound of Formula (IIIb) has the following structure:

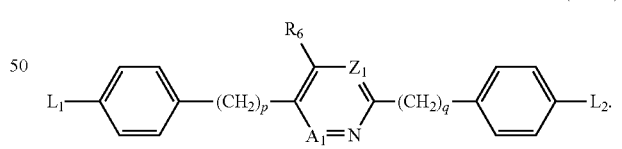
(IIIb-1)

In some embodiments, $Ar_1$ is phenylene and $Ar_3$ is furanyl and the compound of Formula (IIIb) has the following structure:

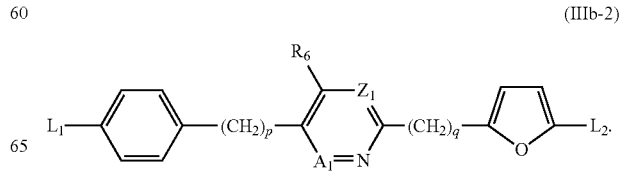
(IIIb-2)

In some embodiments, $Z_1$ and $Y_1$ are each N and the compound of Formula (I) has the following structure:

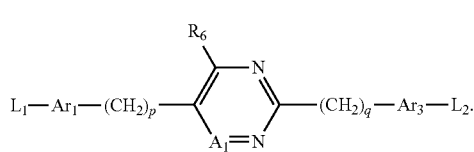

(IIIc)

In some embodiments, $Ar_1$ and $Ar_3$ are each phenylene and the compound of Formula (IIIc) has the following structure:

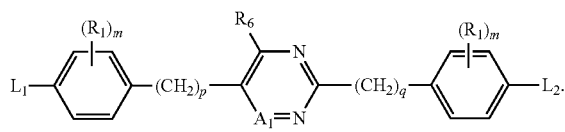

(IIIc-1)

In some embodiments, $Ar_1$ is:

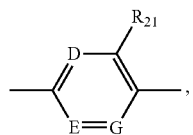

$Ar_3$ is:

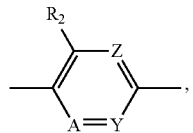

and E and Y are each N, and the compound of Formula (III) has the following structure:

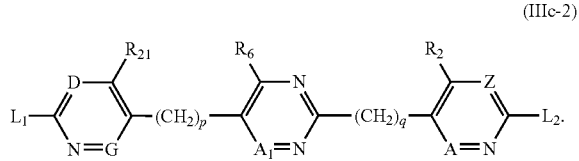

(IIIc-2)

In some embodiments, $A_1$ and $Y_1$ are each N and the compound of Formula (III) has the following formula:

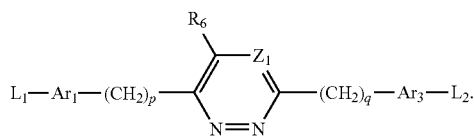

(IIId)

In some embodiments, $A_1$ and $Z_1$ are each N and the compound of Formula (III) has the following formula:

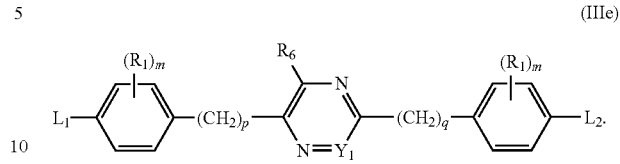

(IIIe)

In some embodiments, the compound of Formula (III) is selected from the group consisting of:
N-Hydroxy-5-{6-[4-(N-hydroxyamidino)-phenyl]-pyridin-3-yl}-furan-2-carboxamidine;
5-[6-(4-Amidinophenyl)-pyridin-3-yl]-furan-2-carboxamidine;
Phenyl[1,1']pyridyl[4',1"]phenyl-4,4"-bis-carboxamidine;
Phenyl[1,1']pyridyl[4',1"]phenyl-4,4"-bis-N-hydroxycarbox-amidine;
Phenyl[1,1']pyridyl[4',1"]phenyl-4,4"-bis-N-methoxycarbox-amidine;
2-[4-(N-Hydroxyamidino)phenyl]-5-[4"-(N-hydroxyamidino)-benzyl]pyridine;
2-(4-Amidinophenyl)-5-(4"-amidinobenzyl)pyridine;
5-[4-(2-Hydrazono)-pyridin-5-yl-phenyl]-furan-2-hydrazone;
5-{4-[2-(4,5-Dihydro-1H-imidazol-2-yl)-hydrazono]-pyridin-5-yl-phenyl}-furan-2-(4,5-dihydro-1H-imidazol-2-yl)-hydrazone;
5-{4-[5-(4,5-Dihydro-1H-imidazol-2-yl)-hydrazono]-pyridin-2-yl-phenyl}-furan-2-(4,5-dihydro-1H-imidazol-2-yl)-hydrazone;
2,5-Bis-(4'-amidinophenyl)-pyrimidine;
2,5-Bis-[4'-(N-hydroxyamidino)phenyl]-pyrimidine,
2,5-Bis-[4'-(N-methoxyamidino)phenyl]-pyrimidine;
3,6-Bis[4-amidinophenyl]pyridazine;
3,6-Bis[4-N-hydroxyamidinophenyl]pyridazine;
3,6-Bis[4-N-methoxyamidinophenyl]pyridazine;
2,5-Bis-(4'-amidinophenyl)pyrazine;
2,5-Bis-(2'-amidinopyridin-5'-yl)pyrimidine;
Phenyl[1,2']pyridinyl[5',5"]pyridinyl-4,2"-bis-amidine;
Phenyl[1,2']pyridinyl[5',5"]pyridinyl-4,2"-bis-N-hydroxyamidine;
Phenyl[1,2']pyridinyl[5',5"]pyridinyl-4,2"-bis-N-methoxyamidine;
Phenyl[1,2']pyridinyl[5',2"]pyridinyl-4,5"-bis-amidine;
Phenyl[1,2']pyridinyl[5',5"]pyrazinyl-4,2"-bis-amidine;
Phenyl[1,2"]pyridinyl[5',5"]pyrimidinyl-4,2"-bis-amidine; and
a pharmaceutically acceptable salt thereof.

In some embodiments of the compound of Formula (I), $Ar_2$ is napthyl and the compound of Formula (I) has the following structure:

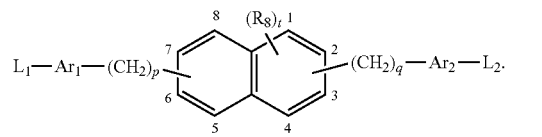

(IV)

In some embodiments, $Ar_1$ and $Ar_3$ are each phenylene and the compound of Formula (IV) has the following structure:

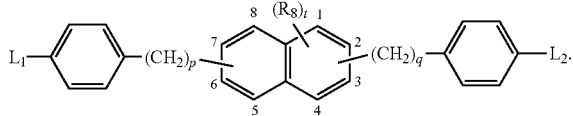
(IVa)

In some embodiments, the naphthyl group is substituted in the 1 and 4 positions and the compound of Formula (IVa) has the following structure:

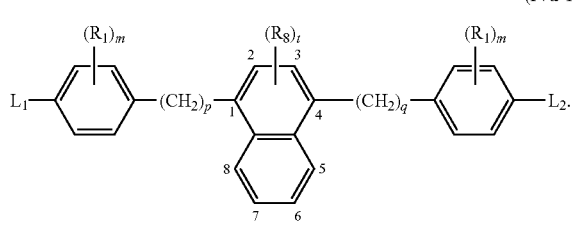
(IVa-1)

In some embodiments, the naphthyl group is substituted in the 2 and 6 positions and the compound of Formula (IVa) has the following structure:

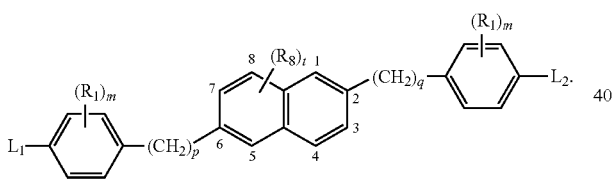
(IVa-2)

In some embodiments, the compound of Formula (I) is selected from the group consisting of:

Phenyl[1,1']napthyl[4',1"]phenyl-4,4"-bis-amidine;
Phenyl[1,1']napthyl[4',1"]phenyl-4,4"-bis-N-hydroxycarbox-amidine;
Phenyl[1,1']naphthyl[4',1"]phenyl-4,4"-bis-N-methoxycarbox-amidine;
Phenyl[1,2']naphthyl[6',1"]phenyl-4,4"-bis-amidine; and
a pharmaceutically acceptable salt thereof.

In some embodiments of the compound of Formula (I), $Ar_2$ is:

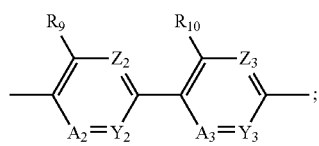

and the compound of Formula (I) has the following formula:

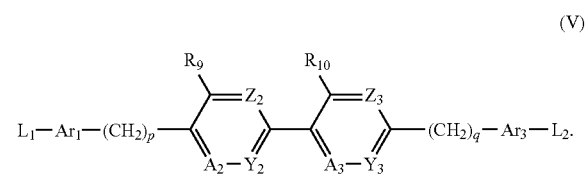
(V)

In some embodiments, $A_2$ and $Y_3$ are each N and the compound of Formula (V) has the following formula:

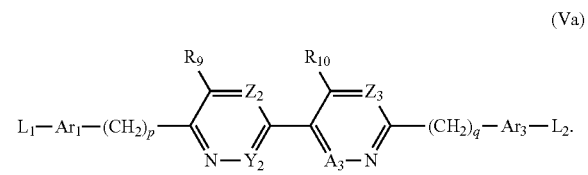
(Va)

In some embodiments, $Ar_1$ and $Ar_3$ are each phenylene and the compound of Formula (Va) has the following formula:

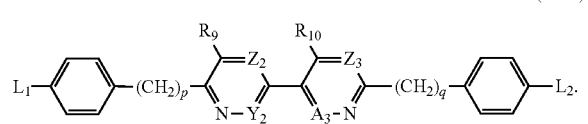
(Va-1)

In some embodiments of the compounds of Formula (I-V), $L_1$ and $L_2$ are each:

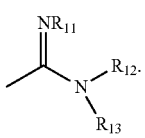

In some embodiments of the compounds of Formula (I-V), $L_1$ and $L_2$ are each:

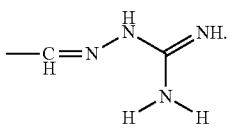

In some embodiments of the compounds of Formula (I-V), $L_1$ and $L_2$ are each:

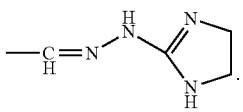

In some embodiments, the compound of Formula (I-V) comprises a pharmaceutically acceptable salt. In some embodiments, the pharmaceutically acceptable salt comprises a hydrochloride salt. In some embodiments, the pharmaceutically acceptable salt comprises an acetate salt.

In some embodiments, the compound of Formula (I-V) is administered in the form of a pharmaceutically acceptable salt. In some embodiments, the pharmaceutically acceptable salt comprises a hydrochloride salt. In some embodiments, the pharmaceutically acceptable salt comprises an acetate salt.

In some embodiments, the microbial infection comprises an infection caused by a *Trypanosoma* spp., including, but not limited to, *Trypanosoma brucei rhodesiense*, *Trypanosoma brucei gambiense*, *Trypanosoma brucei brucei*, and *Trypanosoma cruzi*. In some embodiments, the microbial infection comprises a *Plasmodium falciparum* infection. In some embodiments, the microbial infection comprises an infection caused by a *Leishmania* spp., including, but not limited to, *Leishmania donovani* and *Leishmania mexicana amazonensis*.

In some embodiments, the compound of Formula (I-V) is administered to a subject with an existing microbial infection. In some embodiments, the compound of Formula (I-V) is administered prophylactically to prevent a microbial infection or to prevent the recurrence of a microbial infection. Thus, in some embodiments, the compound of Formula (I-V) is administered prophylactically to prevent or reduce the incidence of one of: (a) a microbial infection in a subject at risk of infection; (b) a recurrence of the microbial infection; and (c) combinations thereof.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment and/or prevention of infectious diseases in warm-blooded vertebrates. Thus, the methods can be used as treatment for mammals and birds.

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided herein is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they also are of economical importance to humans. Thus, embodiments of the methods described herein include the treatment of livestock, including, but not limited to, domesticated swine (pigs and hogs), ruminants, horses, poultry, and the like.

V. General Processes for the Synthesis of Compounds of Formula (I)

The synthetic procedures provided herein below comprise representative novel methods of producing the presently disclosed compounds. The methods are outlined in Schemes 1-16 presented herein below and representative, non-limiting embodiments are described in the Examples.

In some embodiments, the presently disclosed subject matter provides a method for preparing a compound of Formula (I) and pharmaceutically acceptable salts thereof, the method comprising:

(a) forming a teraryl dinitrile compound by one of:

(i) contacting a halogenated aryl nitrile and a 1,4-phenylenebisboronic acid in the presence of a palladium catalyst and a first base in a first aprotic solvent to form a teraryl dinitrile compound;

(ii) contacting a dihalogenated aryl compound with p-cyanophenylboronic acid in the presence of a palladium catalyst and a first base in a first aprotic solvent to form a teraryl dinitrile compound;

(iii) contacting a teraryl dialdehyde compound with hydroxylamine hydrochloride followed by refluxing in acetic anhydride for a period of time to form a teraryl dinitrile compound;

(iv) contacting a teraryl dihalide compound with cuprous cyanide in a first aprotic solvent to form a teraryl dinitrile compound; and (v) contacting a halogenated diarylnitrile with a palladium catalyst and hexa-n-butylditin in a first aprotic solvent;

(b) contacting the teraryl dinitrile compound with one of:

(i) a mixture of hydroxyamine hydrochloride and a second base in a second aprotic solvent to form a dicationic teraryl compound of Formula (I), wherein the dicationic teraryl compound of Formula (I) comprises a diamidoxime teraryl compound of Formula (I); and (ii) a lithium trialkylsilylamide in an second aprotic solvent, followed by a strong acid to form a dicationic teraryl compound of Formula (I), wherein the dicationic teraryl compound of Formula (I) comprises a diamidino compound of Formula (I).

In some embodiments, the method further comprises a step selected from the group consisting of:

(a) contacting the diamidoxime teraryl compound of Formula (I) with a metal hydroxide hydrate followed by a dialkyl sulfate to form a dicationic teraryl compound of Formula (I), wherein the dicationic teraryl compound of Formula (I) comprises a dialkoxyamidino teraryl compound of Formula (I);

(b) contacting the diamidoxime teraryl compound of Formula (I) with acetic acid and acetic anhydride followed by hydrogen and a palladium-on-carbon catalyst to form a dicationic teraryl compound of Formula (I), wherein the dicationic teraryl compound of Formula (I) comprises a diamidino teraryl compound of Formula (I); and (c) dissolving the diamidoxime teraryl compound of Formula (I) in glacial acetic acid and adding acetic anhydride to form a diacetoxyamidino teraryl compound of Formula (I).

In some embodiments, the method comprises forming a teraryl dialdehyde compound by one of:

(a) contacting 4-formylphenylboronic acid with a 5-(haloaryl)-furan-2-carboxaldehyde in the presence of a palladium catalyst and a third base to form a teraryl dialdehyde compound;

(b) contacting 4-formylphenylboronic acid with a dihaloaryl compound in the presence of a palladium catalyst and a third base to form a halogenated diaryl aldehyde, followed by contacting the halogenated diaryl aldehyde with a palladium catalyst and 5-(diethoxymethyl-furan-2-yl)-trimethylstannane to form a teraryl dialdehyde compound;

(c) contacting a 5-halofuran-2-carboxaldehyde and 1,4-phenylenebisboronic acid in the presence of a palladium catalyst and a third base to form a teraryl dialdehyde compound; and
(d) contacting a dihaloaryl compound with (5-diethoxymethyl-furan-2-yl)-trimethyl-stannane and a palladium catalyst, followed by a strong acid to form a 2-haloaryl-5-formyl furan, followed by contacting the 2-haloaryl-5-formyl furan with 4-formylphenylboronic acid in the presence of a second palladium catalyst and a third base to form a teraryl dialdehyde compound.

In some embodiments, the method comprises forming a teraryl dihalide compound by:
(a) contacting 1,4-dibromobenzene and 2-tributylstannyl-furan in the presence of a palladium catalyst to form 2-(4-furan-2-yl-phenyl)-furan; and
(b) contacting 2-(4-furan-2-yl-phenyl)-furan with N-bromosuccinimide (NBS) in a third aprotic solvent to form a dibromide.

In some embodiments, the halogenated aryl nitrile is selected from the group consisting of 4-bromobenzonitrile and 6-chloronicotinonitrile. In some embodiments, the dihalogenated aryl compound is selected from the group consisting of: 2,5-dibromo-1-fluorobenzene; 1,4-dibromo-2-trifluoromethylbenzene; 2,5-dibromopyridine; 2-chloro-5-bromopyrimidine; 2-chloro-5-(chloromethyl)pyridine), 1,4-dibromonaphthalene, and 2,6-dibromonaphthalene.

In some embodiments the presently disclosed subject matter provides a method for preparing a dicationic teraryl compound of Formula (I), the method comprising:
(a) providing a teraryl diamine;
(b) contacting the teraryl diamine with one of
  (i) a mixture of 1,3-bis(t-butoxycarbonyl)-2-methylthiopseudourea and a tertiary amine followed by mercury(II) chloride; and
  (ii) ethyl isothiocyanatoformate, a primary amine, a water-soluble carbodiimide, and a tertiary amine;
  to form a bis-(alkoxycarbonyl)-guanidino teraryl compound; and
(c) contacting the bis-(alkoxycarbonyl)-guanidino teraryl compound with one of an acid and a hydroxide to form a dicationic teraryl compound of Formula (I), wherein the dicationic teraryl compound of Formula (I) comprises a bis-guanidino teraryl compound of Formula (I).

In some embodiments, the teraryl diamine is formed by
(a) contacting a halogenated nitroaryl compound with 1,4-phenylenebisboronic acid in the presence of a palladium catalyst and a base to form a dinitro teraryl compound; and
(b) contacting the dinitro teraryl compound with a palladium-on-carbon catalyst and hydrogen to form the teraryl diamine.

In some embodiments, the presently disclosed subject matter provides a method for preparing a dicationic teraryl compound of Formula (I), the method comprising:
(a) providing a teraryl dialdehyde; and
(b) contacting the teraryl dialdehyde with one of
  (i) aminoguanidine and a base in a polar, protic solvent to form a dicationic teraryl compound of Formula (I), wherein the dicationic teraryl compound of Formula (I) comprises a bis-hydrazone teraryl compound of Formula (I); and
  (ii) 2-hydrazino-2-imidazoline and a base in a polar, protic solvent to form a dicationic teraryl compound of Formula (I), wherein the dicationic teraryl compound of Formula (I) comprises a bis-hydrazone teraryl compound of Formula (I).

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Methods and Materials

Melting points were recorded using a Thomas-Hoover (Uni-Melt) capillary melting point apparatus (Thomas Scientific, Swedesboro, N.J., United States of America) and are uncorrected. TLC analysis was carried out on silica gel 60 $F_{254}$ precoated aluminum sheets and detected under UV light. $^1H$ and $^{13}C$ NMR spectra were recorded employing a Varian GX400 or Varian Unity Plus 300 spectrometer (Varian, Inc., Palo Alto, Calif., United States of America), and chemical shifts (δ) are in ppm relative to TMS as internal standard. Mass spectra were recorded on a VG analytical 70-SE spectrometer (VG Analytical, Ltd., Manchester, United Kingdom). Elemental analyses were obtained from Atlantic Microlab Inc: (Norcross, Ga., United States of America) and are within ±0.4 of the theoretical values. The compounds reported as salts frequently analyzed correctly for fractional moles by water and/or ethanol of solvation. In each case, proton NMR showed the presence of indicated solvent (s). Aldrich Chemical Co. (St. Louis, Mo., United States of America), Fisher Scientific (Fairlawn, N.J., United States of America), Frontier Scientific (Logan, Utah, United States of America) or Lancaster Synthesis, Inc. (Windham, N.H., United States of America).

Example 1

Scheme 1

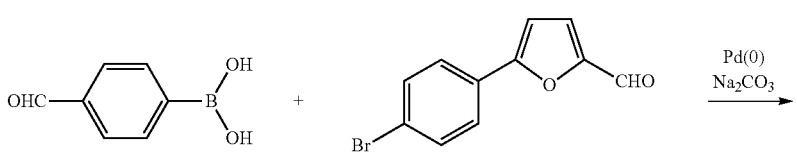

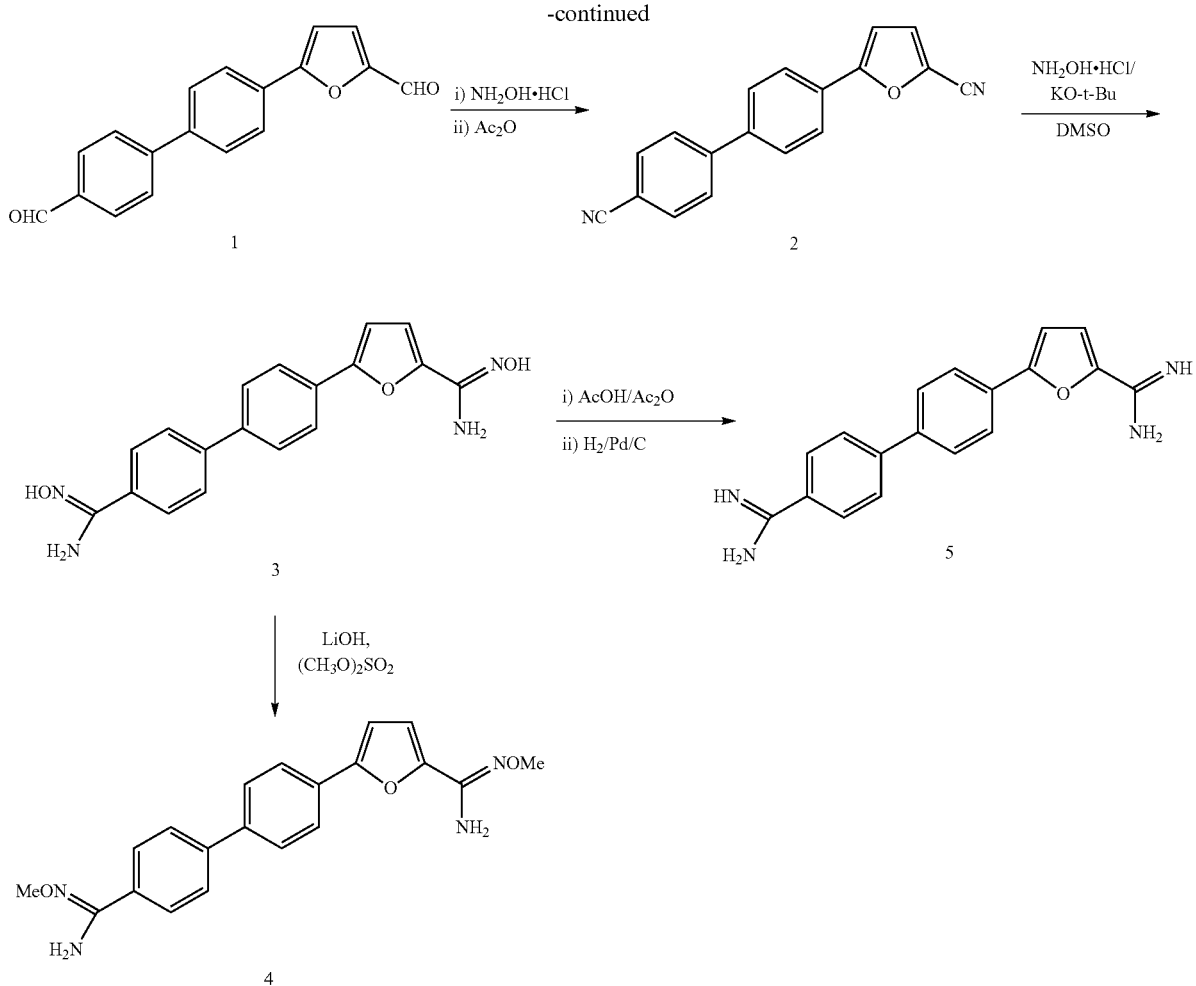

5-(4'-Formylbiphenyl-4-yl)-furan-2-carboxaldehyde (1). To a stirred solution of 5-(4-bromophenyl)-furan-2-carboxaldehyde (5 mmol), and tetrakis(triphenylphosphine) palladium (200 mg) in toluene (10 mL) under a nitrogen atmosphere was added 5 mL of a 2 M aqueous solution of $Na_2CO_3$ followed by 4-formylphenylboronic acid (6 mmol) in 5 mL of methanol. The vigorously stirred mixture was warmed to 80° C. for 12 h. The solvent was evaporated, the precipitate was partitioned between methylene chloride (200 mL) and 2 M aqueous $Na_2CO_3$ (15 mL) containing 3 mL of concentrated ammonia. The organic layer was dried ($Na_2SO_4$), and then concentrated to dryness under reduced pressure to afford 1 in 85% yield; mp 173-174° C. ($SiO_2$, hexanes/EtOAc, 70:30). $^1$H NMR (DMSO-$d_6$); δ 7.42 (d, J=3.6 Hz, 1H), 7.70 (d, J=3.6 Hz, 1H), 7.93-8.01 (m, 8H), 9.64 (s, 1H), 10.07 (s, 1H). $^{13}$C NMR (DMSO-$d_6$); δ 192.7, 177.9, 157.6, 151.8, 144.6, 139.6, 135.3, 130.2, 128.6, 127.9, 127.3, 125.7, 109.5. MS (ESI) m/e (rel. int.): 276 (M+, 100), 247 (5), 219 (25), 189 (25). Anal. Calc. for $C_{18}H_{12}O_3$: C % 78.24; H %, 4.37. Found C %, 77.99; H %, 4.44.

5-(4'-Cyanobiphenyl-4-yl)-furan-2-carbonitrile (2). To a stirred solution of 1 (2 mmol) in 10 mL of methanol was slowly added an aqueous solution (8 mL) of hydroxylamine hydrochloride (4 mmol) and sodium carbonate (4 mmol). The reaction mixture was allowed to reflux for 6 h. The solvent was evaporated, the precipitate was partitioned between water and ethyl acetate (150 mL), the organic layer was dried ($Na_2SO_4$), and then concentrated to dryness under reduced pressure. The crude oxime was allowed to reflux in acetic anhydride (8 mL) for 4 h. The reaction mixture was poured slowly onto ice water and the precipitate was filtered and washed with water to afford 2 in 89% yield; mp 216-218° C. $^1$H NMR (DMSO-$d_6$); δ 7.38 (d, J=3.6 Hz, 1H), 7.75 (d, J=3.6 Hz, 1H), 7.88-7.96 (m, 8H). $^{13}$C NMR ((DMSO-$d_6$); δ 157.4, 143.4, 138.9, 132.9, 128.3, 127.8, 127.5, 125.8, 125.4, 124.3, 118.7, 112.0, 110.4, 108.3. MS (ESI) m/e (rel. int.): 270 (M+, 100), 241 (5), 214 (10). Anal. Calc. for $C_{18}H_{10}N_2O$: C %, 79.99; H %, 3.73. Found C %, 79.85; H %, 3.91.

N-Hydroxy-5-[4'-(N-hydroxyamidino)-biphenyl-4-yl]-furan-2-carboxamidine (3). A mixture of hydroxylamine hydrochloride (1.83 g, 26.3 mmol, 10 equiv) in anhydrous DMSO (30 mL) was cooled to 5° C., and then potassium t-butoxide (2.95 g, 26.3 mmol, 10 equiv) was added portion wise. To the mixture was added the dinitrile 2 (2.6 mmol) and the reaction was kept stirring overnight at room temperature. The reaction mixture was poured onto ice/water whereupon a white precipitate of the bisamidoxime was formed. The product was collected by filtration and washed with water to afford 3 (free base) in 92% yield; mp 229-230° C. $^1$H NMR (DMSO-$d_6$); δ 5.87 (s, 4H), 6.85 (d, J=3.6 Hz, 1H), 7.06 (d, J=3.6 Hz, 1H), 7.71-7.87 (m, 8H), 9.70 (s, 2H).

3 Hydrochloride salt. mp >300° C. $^1$H NMR (DMSO-$d_6$); 7.38 (d, J=3.9 Hz, 1H), 7.82 (d, J=3.9 Hz, 1H), 7.87 (d, J=8.4 Hz, 2H), 7.92 (d, J=8.4 Hz, 2H), 8.01 (d, J=8.4 Hz, 2H), 8.15

(d, J=8.4 Hz, 2H), 9.14 (br s, 4H), 11.36 (br s, 2H), 13.19 (br s, 2H). $^{13}$C NMR (DMSO-d$_6$); δ 158.7, 158.5, 148.7, 143.5, 138.8, 138.4, 128.6, 128.5, 127.4, 126.9, 125.5, 124.6, 119.2, 108.8. MS (ESI) m/e (rel. int.): 337 (M$^+$, 65), 322 (50), 307 (100), 272 (40). Anal. Calc. for C$_{18}$H$_{16}$N$_4$O$_3$-2.0HCl: C %, 52.82; H %, 4.43; N %, 13.68. Found C %, 52.60; H %, 4.45; N %, 13.30.

N-Methoxy-5-[4'-(N-methoxyamidino)-biphenyl-4-yl]-furan-2-carboxamidine (4). To a suspension of the amidoxime 3 (1 mmol) in DMF (15 mL) was added LiOH.H$_2$O (6 mmol, in 3 mL H$_2$O) followed by dimethyl sulfate (5 mmol). The reaction was kept stirring overnight after which it was poured onto ice/water and the precipitate was filtered, washed with water and dried to give the desired compound in 92% yield; mp 214-215° C. $^1$H NMR (DMSO-d$_6$); δ 3.75 (s, 6H), 6.12 (d, J=3.6 Hz, 1H), 6.17 (d, J=3.6 Hz, 1H), 7.76-8.00 (m, 8H).

4 Hydrochloride salt. mp 194-196° C. $^1$H NMR (D$_2$O/DMSO-d$_6$); δ 3.88 (s, 6H), 7.20 (d, J=3.6 Hz, 1H), 7.34 (d, J=3.6 Hz, 1H), 7.77-8.13 (m, 8H). Anal. Calc. for C$_{20}$H$_{20}$N$_4$O$_3$-2.0HCl: C %, 54.92; H %, 5.07; N %, 10.97. Found C %, 54.88; H %, 5.29; N %, 10.99.

5-(4'-Amidinobiphenyl-4-yl)-furan-2-carboxamidine acetate salt (5). To a solution of 3 (1 mmol) in glacial acetic acid (10 mL) was slowly added acetic anhydride (0.35 mL). After stirring for overnight TLC indicated complete acylation of the starting material, then was added 10% palladium on carbon (80 mg). The mixture was placed on Parr hydrogenation apparatus at 50 psi for 4 h at room temperature. The mixture was filtered through hyflo and the filter pad washed with water. The filtrate was evaporated under reduced pressure and the precipitate was collected and washed with ether to give 5 in 71% yield, mp 236-238° C. $^1$H NMR (D$_2$O/DMSO-d$_6$); δ 1.78 (s, 2×CH$_3$), 7.31 (d, J=3.6 Hz, 1H), 7.61 (d, J=3.6 Hz, 1H), 7.85-8.11 (m, 8H). EIMS m/e (rel. int.); 304 (M$^+$, 20), 287 (100), 270 (50), 216 (30), 190 (10). High resolution Calc. for C$_{18}$H$_{16}$N$_4$O ms 304.13241. Observed 304.13201. Anal. Calc. for C$_{16}$H$_{14}$N$_4$O$_2$-2.0AcOH-1.75H$_2$O-0.25EtOH: C %, 57.81; H %, 6.25; N %, 11.98. Found C %, 58.18; H %, 5.90; N %, 11.56.

Example 2

Scheme 2

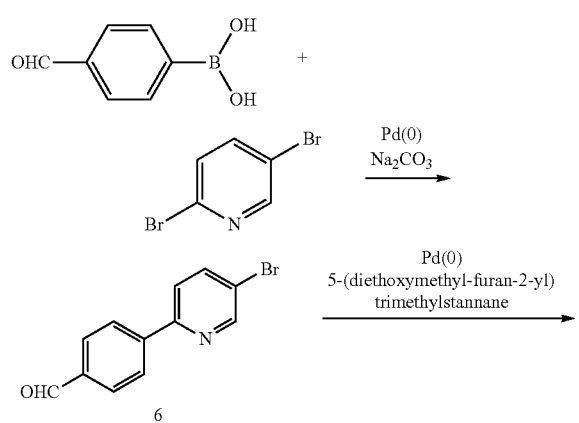

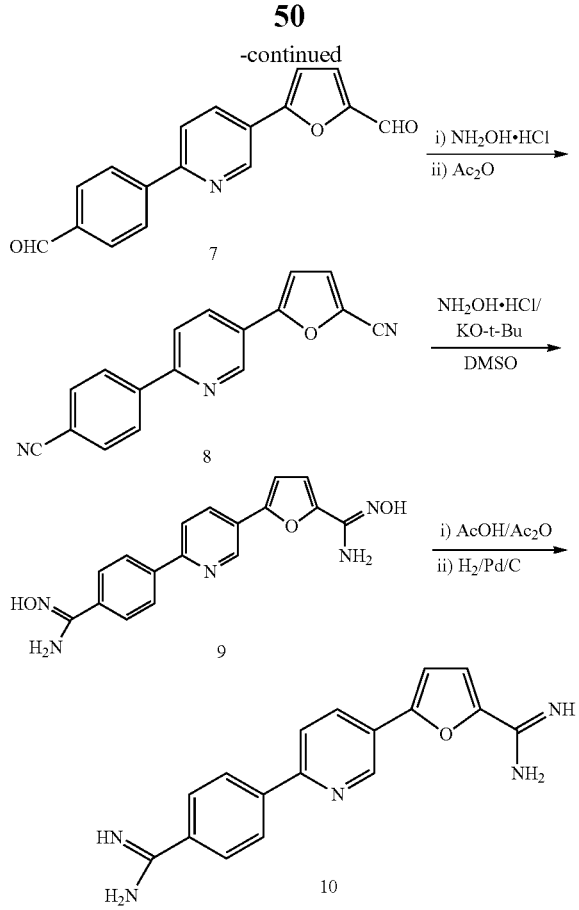

4-(5-Bromopyridin-2-yl)-benzaldehyde (6). The same procedure described for 1 was used by employing 2,5-dibromopyridine (1 equiv.) and 4-formylphenyl boronic acid (1 equiv.). Yield 71%, mp 120-121° C. $^1$H NMR (DMSO-d$_6$); δ 7.97 (d, J=8.4 Hz, 2H), 8.04 (d, J=8.7 Hz, 1H), 8.16 (dd, J=2.4, 8.7 Hz, 1H), 8.26 (d, J=8.4 Hz, 2H), 8.80 (d, J=2.4 Hz, 1H), 10.08 (s, 1H). MS (ESI) m/e (rel. int.): 262 (M$^+$, 100), 232 (30), 153 (55). Anal. Calc. for C$_{12}$H$_8$BrNO: C %, 54.99; H %, 3.08. Found C %, 54.75; H %, 3.14.

5-[6-(4-Formylphenyl)-pyridin-3-yl]-furan-2-carboxaldehyde (7). To a stirred solution of 6 (10 mmol) in 40 mL dry 1,4-dioxane was added palladium tetrakis-triphenylphosphine (400 mg), then 5-(diethoxymethyl-furan-2-yl)-trimethylstannane (10 mmol) was added and the reaction mixture was refluxed at 100° C. for 24 h. The solvent was then evaporated to dryness to give a dark brown residue that was suspended in water and extracted with CH$_2$Cl$_2$. The organic layer was passed over hyflo, dried (Na$_2$SO$_4$) and evaporated to dryness under reduced pressure, followed by acid hydrolysis with 2M HCl to furnish 7. Yield 79%; mp 204-206° C. (EtOH). $^1$H NMR (DMSO-d$_6$); δ 7.55 (d, J=3.6 Hz, 1H), 7.73 (d, J=3.6 Hz, 1H), 8.06 (d, J=8.4 Hz, 2H), 8.27 (d, J=8.4 Hz, 1H), 8.37-8.41 (m, 3H), 9.24 (d, J=2.1 Hz, 1H), 9.67 (s, 1H), 10.09 (s, 1H). $^{13}$C NMR (DMSO-d$_6$); δ 192.8, 178.1, 155.2, 154.7, 152.3, 146.3, 142.9, 136.5, 133.3, 130.0, 127.2, 125.1, 124.3, 121.4, 110.6. Anal. Calc. for C$_{17}$H$_{11}$NO$_3$: C %, 73.63; H %, 3.99. Found C %, 73.75; H %, 3.81.

5-[6-(4-Cyanophenyl)-pyridin-3-yl]-furan-2-carbonitrile (8). The same procedure described for 2 was used starting with 7. Yield 40%, mp 203-205° C. $^1$H NMR (DMSO-d$_6$); δ 7.53 (d, J=3.6 Hz, 1H), 7.82 (d, J=3.6 Hz, 1H), 8.00 (d, J=8.4 Hz, 2H), 8.27 (d, J=8.4 Hz, 1H), 8.35-8.37 (m, 3H), 9.21 (d, J=2.1 Hz, 1H). Anal. Calc. for $C_{17}H_9N_3O$: C %, 75.26; H %, 3.34. Found C %, 75.44; H %, 3.54.

N-Hydroxy-5-{6-[4-(N-hydroxyamidino)-phenyl]-pyridin-3-yl}-furan-2-carboxamidine (9). The same procedure described for 3 was used starting with 8. Yield 90%; mp 194-195° C. $^1$H NMR (DMSO-$d_6$); δ 5.89 (s, 2H), 5.95 (s, 2H), 6.90 (d, J=3.6 Hz, 1H), 7.22 (d, J=3.6 Hz, 1H), 8.00 (d, J=8.4 Hz, 2H), 8.07-8.26 (m, 4H), 9.11 (d, J=2.1 Hz, 1H), 9.76 (s, 2H). Anal. Calc. for $C_{17}H_{15}N_5O_3$: C %, 60.52; H %, 4.48. Found C %, 60.73; H %, 4.22.

5-[6-(4-Amidinophenyl)-pyridin-3-yl]-furan-2-carboxamidine acetate salt (10). The same procedure described for 5 was used starting with 9. Yield 57%, mp 239-241° C. $^1$H NMR ($D_2O$/DMSO-$d_6$); δ 1.93 (s, 3×CH$_3$), 7.31 (d, J=3.6 Hz, 1H), 7.42 (d, J=3.6 Hz, 1H), 7.92 (d, J=8.4 Hz, 2H), 8.15-8.37 (m, 4H), 9.24 (s, 1H). EIMS m/e (rel. int.); 305 (M$^+$+1, 55), 289 (10), 273 (15), 237 (100). High resolution Calc. for $C_{17}H_{16}N_5O$ ms 306.1354. Observed 306.1349. Anal. Calc. for $C_{17}H_{15}N_5O$-3.0AcOH-2.4H$_2$O: C %, 52.25; H %, 6.02; N %, 13.25. Found. C %, 51.95; H %, 5.70; N %, 12.90.

Example 3

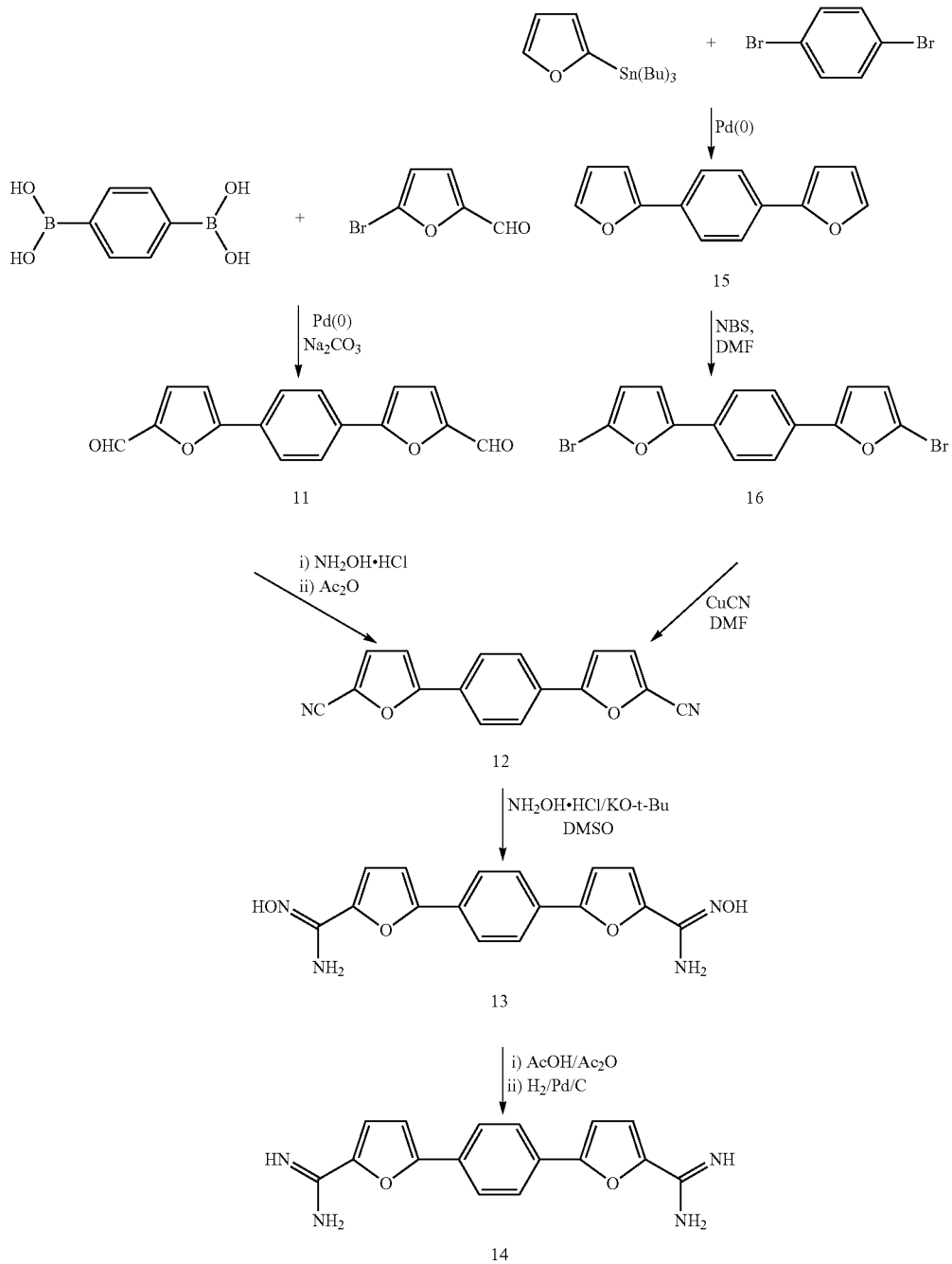

Scheme 3

5-[4-(5-Formylfuran-2-yl)-phenyl]-furan-2-carboxaldehyde (11). To a stirred solution of 5-bromofuran-2-carboxaldehyde (10 mmol), and tetrakis(triphenylphosphine) palladium (400 mg) in toluene (20 ml.) under a nitrogen atmosphere was added 10 mL of a 2 M aqueous solution of $Na_2CO_3$ followed by 1,4-phenylenebisboronic acid (5 mmol) in 6 mL of methanol. The vigorously stirred mixture was warmed to 80° C. for 12 h. The solvent was evaporated, the precipitate was partitioned between methylene chloride (300 mL) and 2 M aqueous $Na_2CO_3$ (15 mL) containing 5 mL of concentrated ammonia. The organic layer was dried ($Na_2SO_4$), and then concentrated to dryness under reduced pressure to afford 11 in 93% yield; mp 233-234° C. (EtOH). $^1$H NMR (DMSO-$d_6$); δ 9.64 (s, 2H), 8.01 (s, 4H), 7.70 (d, J=3.6 Hz, 2H), 7.43 (d, J=3.6 Hz, 2H). MS (ESI) m/e (rel. int.): 266 ($M^+$, 100), 238 (5), 209 (25). Anal. Calc. for $C_{16}H_{10}O_4$: C %, 72.16; H %, 3.78. Found C %, 72.41; H %, 3.93.

2-(4-Furan-2-yl-phenyl)-furan (15). To a stirred solution of 1,4-dibromobenzene (5 mmol) was added palladium tetrakistriphenylphosphine (400 mg). The reaction mixture was kept stirring for 15 min after which 2-tributylstannylfuran (10 mmol) was added and the reaction mixture was refluxed at 100° C. for 24 h. The solvent was then evaporated to dryness to give a dark brown residue that was suspended in water and extracted with $CH_2Cl_2$. The organic layer was passed over hyflo, dried ($Na_2SO_4$) and evaporated to dryness under reduced pressure to give 15 in 91% yield; mp 149-150° C. $^1$H NMR (DMSO-$d_6$); δ 6.62 (d, 2H), 7.01 (d, 2H), 7.76-7.79 (m, 6H). MS (ESI) m/e (rel. int.): 210 ($M^+$, 100), 181 (40), 153 (30). Anal. Calc. for $C_{14}H_{10}O_2$: C %, 79.98; H %, 4.79. Found C %, 80.12; H %, 4.59.

2-Bromo-5-[4-(5-bromofuran-2-yl)-phenyl]-furan (16). To an ice bath cooled solution of 15 (5 mmol) in 20 mL DMF was added NBS (12 mmol) in portions. The reaction mixture was kept stirring at room temperature for overnight, after which it was poured onto ice/water. The precipitate formed was collected by filtration and washed with water then dried, yield 85%; mp 155-157° C. $^1$H NMR (DMSO-$d_6$); δ 6.74 (d, J=3.6 Hz, 2H), 7.10 (d, J=3.6 Hz, 2H), 7.72 (dd, J=4.2, 8.7 Hz, 4H). MS (ESI) m/e (rel. int.): 366, 368 ($M^+$, 100:30), 339 (40), 259 (45). Anal. Calc. for $C_{14}H_5Br_2O_2$: C %, 45.69; H %, 2.19. Found C %, 45.52; H %, 2.32.

5-[4-(5-Cyanofuran-2-yl)-phenyl]-furan-2-carbonitrile (12)

Method I: The same procedure described for 2 was used starting with 11, to afford 12 in 30% yield.

Method II: To a solution of the dibromide 16 (6.25 g, 17 mmol) in dry DMF (40 mL), was added cuprous cyanide (4.58 g, 51 mmol). The reaction was heated under reflux for 24 h, poured onto ice/water, 5 mL concentrated ammonia solution was added to the mixture which was then extracted with methylene chloride (3×150 mL).

The organic layer was dried (anhydrous $Na_2SO_4$) and evaporated to dryness to give 12 in 45% yield; mp 245-246° C. $^1$H NMR (DMSO-$d_6$); δ 7.39 (d, J=3.6 Hz, 2H), 7.75 (d, J=3.6 Hz, 2H), 7.96 (s, 4H). MS (ESI) m/e (rel. int.): 260 ($M^+$, 100), 206 (15), 177 (25). Anal. Calc. for $C_{16}H_8N_2O_2$: C %, 73.82; H %, 3.10. Found C %, 73.50; H %, 3.34.

N-Hydroxy-5-{4-[5-(N-hydroxyamidino)-furan-2-yl]-phenyl}-furan-2-carboxamidine (13). The same procedure described for 3 was used starting with 12. Yield 93%; mp >300° C. $^1$H NMR (DMSO-$d_6$); δ 5.88 (br s, 4H), 6.86 (d, J=3.6 Hz, 2H), 7.06 (d, J=3.6 Hz, 2H), 7.83 (s, 4H), 9.71 (br s, 2H). MS (ESI) m/e (rel. int.): 326 ($M^+$, 100), 311 (15), 292 (15). Anal. Calc. for $C_{16}H_{14}N_4O_4$: C %, 58.89; H %, 4.32. Found C %, 58.62; H %, 4.50.

5-{4-[5-Amidinofuran-2-yl]-phenyl}-furan-2-carboxamidine acetate salt (14). The same procedure described for 4 was used starting with 13. Yield 73%, mp 228-230° C. $^1$H NMR ($D_2O$/DMSO-$d_6$); 1.90 (s, 3×$CH_3$), 7.25 (d, J=3.3 Hz, 2H), 7.55 (d, J=3.3 Hz, 2H), 8.16 (s, 4H). EIMS m/e (rel. int.); 294 ($M^+$, 35), 277 (100), 260 (50), 206 (20), 177 (10). High resolution calcd for $C_{16}H_{14}N_4O_2$ ms 294.11168. Observed 294.10975. Anal. Calc. for $C_{16}H_{14}N_4O_2 \cdot 3.0AcOH \cdot 2.5H_2O \cdot 0.5EtOH$: C %, 50.92; H %, 6.30; N %, 10.32. Found C %, 50.94; H %, 6.00; N %, 9.96.

Example 4

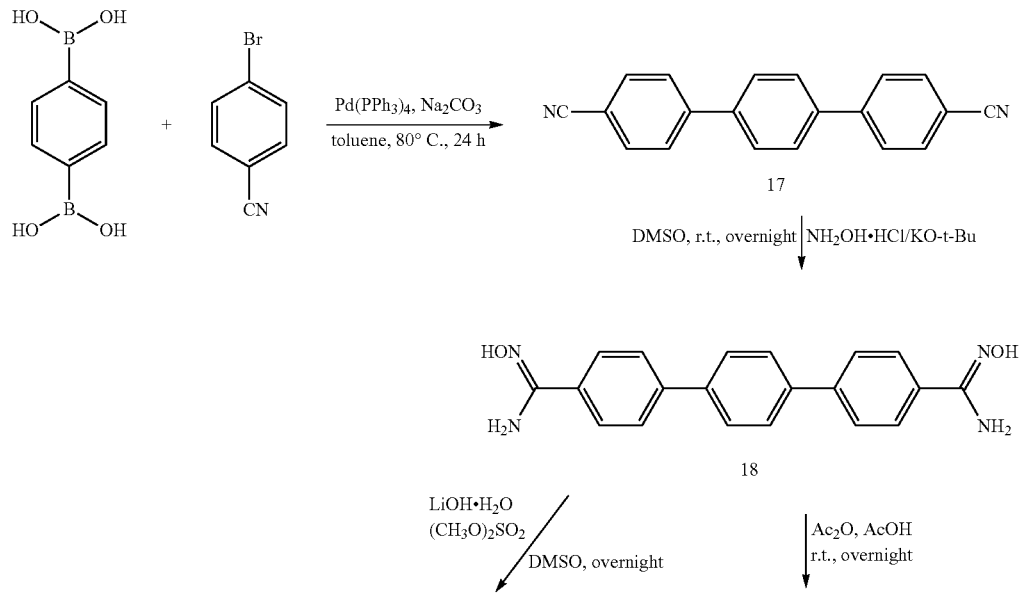

Scheme 4

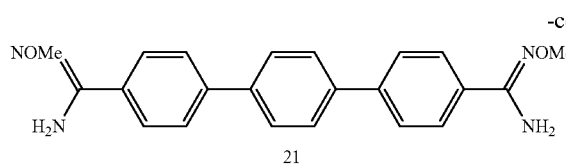

21

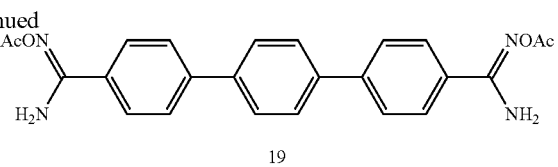

19

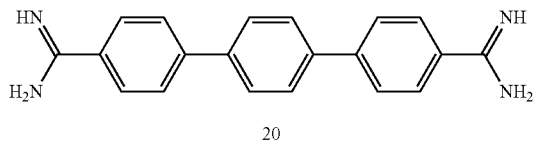

20

4,4''-Bis-cyano[1,1';4',1'']terphenyl (17). The same procedure described for 1 was used by employing 4-bromobenzonitrile (2 equiv.) and 1,4-phenylenebisboronic acid (1 equiv.) to furnish 17 as a white solid in 73% yield; mp 299-300° C. $^1$H NMR (DMSO-d$_6$): δ 7.89 (dd, J=8.1, 2.1 Hz, 4H), 7.94-7.96 (m, 8H). MS (ESI) m/e (rel. int.): 280 (M$^+$, 100). Anal. Calc. for C$_{20}$H$_{12}$N$_2$: C %, 85.69; H %, 4.31. Found C %, 85.41; H %, 4.52.

[1,1';4',1'']Terphenyl-4,4''-bis-N-hydroxycarboxamidine (18). The same procedure described for 3 was used starting with 17 to furnish 18 (free base) in 68% yield; mp >300° C. $^1$H NMR (DMSO-d$_6$): δ 5.67 (br s, 4H), 7.71-7.79 (m, 12H), 9.60 (br s, 2H). MS (ESI) m/e (rel. int.): 347 (M$^+$+1, 40), 279 (100).

Hydrochloride salt of 18 was prepared by suspending the free base in dry ethanol, cooling the mixture in an ice bath (5° C.), and passing HCl gas for about 10 min; mp >300° C. $^1$H NMR (DMSO-d$_6$): δ 7.33 (dd, J=8.1, 2.1 Hz, 4H), 7.64 (br s, 8H), 7.77-7.80 (m, 8H), 10.21 (br s, 2H). $^{13}$C NMR (DMSO-d$_6$): δ 156.1, 138.3, 137.3, 134.9, 127.7, 127.1, 124.7. Anal. Calc. for C$_{20}$H$_{18}$N$_4$O$_2$-2.0HCl-0.25H$_2$O-0.25C$_2$H$_5$OH: C %, 56.56; H %, 5.12; N %, 12.55. Found C %, 56.56; H %, 5.09; N %, 12.87.

[1,1';4',1'']Terphenyl-4,4''-bis-N-acetoxycarboxamidine (19). The diamidoxime 18 (0.60 g, 1.73 mmol) was dissolved in glacial acetic acid (17.3 mL), and then acetic anhydride (0.61 mL) was added dropwise. After letting the reaction stir at room temperature overnight, the mixture was poured onto ice/water and the precipitate formed was collected by filtration, washed with water and dried to give 19 in 89% yield; mp 293-295° C. $^1$H NMR (DMSO-d$_6$): δ 2.14 (s, 6H), 6.87 (br s, 4H), 7.82-7.84 (m, 12H). $^{13}$C NMR (DMSO-d$_6$): δ 168.4, 156.0, 141.2, 138.6, 130.7, 127.3, 126.4, 19.8. Anal. Calc. for C$_{24}$H$_{22}$N$_4$O$_4$-0.5CH$_3$CO$_2$H: C %, 65.20; H %, 5.25. Found C %, 65.10; H %, 4.99.

[1,1';4',1'']Terphenyl-4,4''-bis-carboxamidine acetate salt (20). The same procedure described for 5 was used starting with 19; mp >300° C. $^1$H NMR (D$_2$O/DMSO-d$_6$): δ 1.78 (s, 2xCH$_3$), 7.52-7.54 (m, 4H), 7.58-7.61 (d, J=8.1 Hz, 2H), 7.76-7.79 (m, 4H), 7.90 (d, J=8.1 Hz, 2H). MS (ESI) m/e (rel. int.): 315 (M$^+$+1, 33), 158 (100), 121 (40). Anal. Calc. for C$_{24}$H$_{22}$N$_4$O$_4$-2.0CH$_3$CO$_2$H-0.5H$_2$O: C %, 64.99; H %, 6.13; N %, 12.63. Found C %, 64.97; H %, 6.01; N %, 12.60.

[1,1';4',1'']Terphenyl-4,4''-bis-N-methoxycarboxamidine (21). The same procedure described for 4 was used starting with 18 to give free base of 21 in 72% yield; mp 270-272° C. $^1$H NMR (DMSO-d$_6$): δ 3.75 (s, 6H), 6.10 (br s, 4H), 7.75-7.80 (m, 12H).

Hydrochloride salt of 21, mp 240-242° C. $^1$H NMR (DMSO-d$_6$): δ 3.86 (s, 6H), 7.95-7.90 (m, 12H), 8.45 (br s, 4H). Anal. Calc. for C$_{20}$H$_{18}$N$_4$O$_2$-2.0HCl: C %, 59.07; H %, 5.41; N %, 12.52. Found C %, 59.54; H %, 5.44; N %, 12.10.

Example 5

Scheme 5

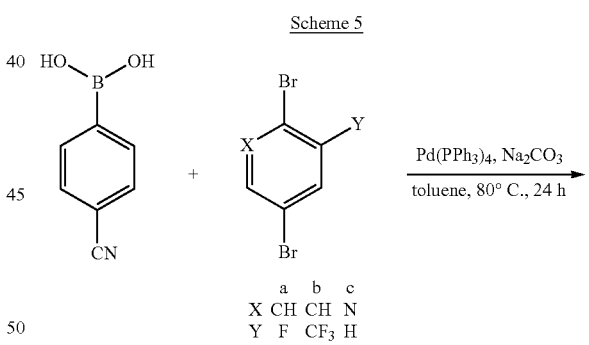

| | a | b | c |
|---|---|---|---|
| X | CH | CH | N |
| Y | F | CF$_3$ | H |

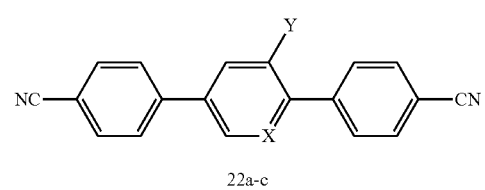

22a-c

NH$_2$OH·HCl/KO-t-Bu, DMSO
r.t., overnight
or
a) LiN(TMS)$_2$, THF,
b) HCl (gas), dry EtOH -continued

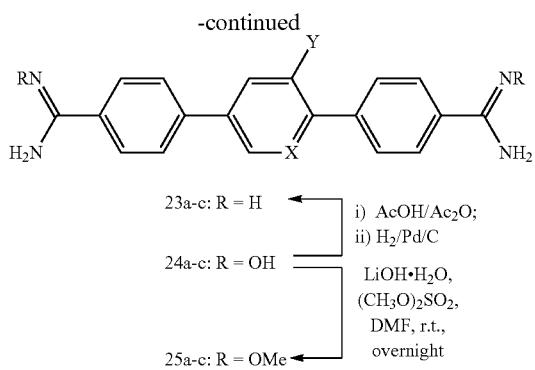

23a-c: R = H
24a-c: R = OH
25a-c: R = OMe i) AcOH/Ac$_2$O;
ii) H$_2$/Pd/C

LiOH·H$_2$O,
(CH$_3$O)$_2$SO$_2$,
DMF, r.t.,
overnight

2'-Fluoro-[1,1';4',1"]terphenyl-4,4"-bis-carbonitrile (22a). Adopting the same procedure used for the preparation of 17, a Suzuki coupling reaction was performed using 2,5-dibromo-1-fluorobenzene (3.50 g, 13.78 mmol) and p-cyanophenyl boronic acid (4.45 g, 30.32 mmol) to yield the target bis-cyano derivative in 89% yield, mp 289-291° C. $^1$H NMR (DMSO-d$_6$): δ 7.72-7.83 (m, 5H) 7.90-7.99 (m, 6H). Anal. Calc. for C$_{20}$H$_{11}$N$_2$: C %, 80.52; H %, 3.71. Found C %, 80.24; H %, 3.95.

2'-Fluoro-[1,1';4',1"]terphenyl-4,4"-bis-amidine hydrochloride salt (23a). The dinitrile 22a (0.5 g, 1.67 mmol), suspended in freshly distilled THF (5 mL), was treated with lithium trimethylsilylamide (2% solution in THF, 3.67 mmol) and the reaction was kept stirring overnight. The reaction mixture was then cooled to 0° C. and four equivalents of 6N HCl saturated ethanol (100 mL) whereupon a precipitate started forming. The reaction was left to run overnight whereafter it was diluted with ether and the formed solid was filtered to give the diamidine salt; mp >300° C. $^1$H NMR (DMSO-d$_6$): δ 7.72-7.89 (m, 5H), 7.97-8.07 (m, 6H), 9.34 (br s, 4H), 9.54 (br s, 4H). MS (ESI) m/e (rel. int.): 333 (M$^+$, 100), 316 (23), 299 (27). Anal. Calc. for C$_{20}$H$_{11}$N$_2$·2.0HCl·0.5H$_2$O: C %, 57.35; H %, 4.93; N %, 13.37. Found C %, 57.54; H %, 4.88; H %, 13.35.

2'-Fluoro-[1,1';4',1"]terphenyl-4,4"-bis-N-hydroxycarboxamidine (24a). The same procedure described for preparation of 3 was used starting with 22a. Yield % 96, mp >300° C. $^1$H NMR (DMSO-d$_6$): δ 5.83 (br s, 4H), 7.62-7.73 (m, 5H), 7.79-7.81 (m, 6H), 9.60 (br s, 2H). MS (ESI) m/e (rel. int.): 364 (M$^+$, 100), 183 (42).

24a hydrochloride salt: mp 282-284° C. $^1$H NMR (DMSO-d$_6$): δ 7.74-7.86 (m, 9H), 8.02-8.05 (m, 2H), 9.10 (br s, 4H), 11.31 (br s, 2H). Anal. Calc for C$_{20}$H$_{17}$FN$_4$O$_2$·2.0HCl·0.75H$_2$O: C %, 53.82; H %, 4.51; N %, 12.55. Found C %, 53.88; H %, 4.43; N %, 12.29.

2'Fluoro-[1,1';4',1"]terphenyl-4,4"-bis-methoxycarboxamidine (25a). The target compound was prepared adopting the same procedure mentioned for 4 starting with 24a, yield 74%; mp 172-174° C. $^1$H NMR (DMSO-d$_6$): δ 3.76 (s, 6H), 6.11 (br s, 4H), 7.60-7.78 (m, 11H). MS (ESI) m/e (rel. int.): 393 (M$^+$, 100), 197 (28).

25a hydrochloride salt: mp 250-252° C. Anal. Calc. for C$_{22}$H$_{21}$FN$_4$O$_2$·2.0HCl·0.25H$_2$O·0.25C$_2$H$_5$OH: C %, 56.14; H %, 5.23; N %, 11.63. Found C %, 56.13; H %, 4.93; N %, 11.43.

2'-Trifluoromethyl-[1,1';4',1"]terphenyl-4,4"-bis-carbonitrile (22b). Following the same synthetic procedure employed for 22a using 1,4-dibromo-2-trifluoromethylbenzene (3.33 g, 10 mmol) and p-cyanophenyl boronic acid (3.23 g, 22 mmol) to yield the dinitrile as a white solid (87%); mp 181-183° C. $^1$H NMR (DMSO-d$_6$): δ 7.55-7.58 (m, 3H), 7.94-8.02 (m, 6H), 8.04-8.16 (m, 2H). MS (ESI) m/e (rel. int.): 298 (M$^+$, 100), 149 (62), 122 (42). Anal. Calc. for C$_{21}$H$_{11}$F$_3$N$_2$: C %, 72.41; H %, 3.18. Found C %, 72.68; H %, 3.34.

2'-Trifluoromethyl-[1,1';4',1"]terphenyl-4,4"-bis-amidine hydrochloride salt (23b). The amidine was prepared following the procedure which used for 23a; mp >300° C. $^1$H NMR (DMSO-d$_6$): δ 7.56-7.64 (m, 3H), 7.96 (dd, J=1.5, 8.1 Hz, 2 H), 8.02 (dd, J=1.5, 8.1 Hz, 2 H), 8.10 (dd, J=1.5, 8.1 Hz, 2 H), 8.18 (dd, J=1.5, 8.1 Hz, 2 H), 9.36 (br s, 4H), 9.57 (br s, 4H). MS (ESI) m/e (rel. int.): 383 (M$^+$, 23), 192 (100). Anal. Calc. for C$_{21}$H$_{17}$F$_3$N$_4$·2.0HCl·0.5H$_2$O·0.1C$_2$H$_5$OH: C %, 54.30; H %, 4.42; N %, 11.94. Found C %, 54.11; H %, 4.24; N %, 11.66.

2'-Trifluoromethyl-[1,1';4',1"]terphenyl-4,4"-bis-N-hydroxycarboxamidine (24b). The same procedure described for preparation of 3 was used starting with 22b. Yield 94%; mp 204-206° C. $^1$H NMR (DMSO-d$_6$): δ 5.96 (br s, 4H), 7.37 (dd, J=1.8, 8.7 Hz, 2 H), 7.50 (d, J=7.8 Hz, 1H), 7.75 (dd, J=1.8, 8.7 Hz, 2 H), 7.80-7.82 (m, 4H), 8.03-8.07 (m, 2H), 9.76 (br s, 2H). MS (ESI) m/e (rel. int.): 415 (M$^+$, 26), 208 (100).

24b hydrochloride salt: mp 229-231° C. $^1$H NMR (DMSO-d$_6$): δ 7.55-7.61 (m, 3H), 7.84-7.92 (m, 4H), 8.07 (dd, J=1.8, 8.7 Hz, 2 H), 8.14-8.18 (m, 2H), 9.11 (br s, 4H), 11.35 (br s, 2H). Anal. Calc. for C$_{21}$H$_7$N$_4$O$_2$·2.0HCl·1.25H$_2$O·0.25C$_2$H$_5$OH: C %, 49.53; H %, 4.44; N %, 10.74. Found C %, 49.55; H %, 4.40; N %, 10.55.

2'-Trifluoromethyl-[4',1';4',1"]terphenyl-4,4"-bis-methoxycarboxamidine (25b). The amidoxime 24b was used to prepare the corresponding methoxime using the above-mentioned method in 72% yield; mp 186-188° C. $^1$H NMR (DMSO-d$_6$): δ 3.75 (s, 3H), 3.76 (s, 3H), 6.14 (br s, 4H), 7.36 (dd, J=1.8, 8.4 Hz, 2H), 7.50 (d, J=8.1 Hz, 1H), 7.73 (dd, J=1.8, 8.1 Hz), 7.80-7.82 (m, 4H), 8.03-8.07 (m, 2H). MS (ESI) m/e (rel. int.): 443 (M$^+$, 59), 222 (100).

25b hydrochloride salt: mp 214-216° C. Anal. Calc. for C$_{23}$H$_{21}$F$_3$N$_4$O$_2$·2.0HCl·1.25H$_2$O·0.5C$_2$H$_5$OH: C %, 51.39; H %, 5.12; N %, 9.98. Found C %, 51.54; H %, 4.84; N %, 9.94.

Phenyl[1,1']pyridyl[4',1"]phenyl-4,4"-bis-carbonitrile (22c). 2,5-Dibromopyridine and p-cyanophenylboronic acid were reacted under the above mentioned Suzuki coupling conditions to give the target dinitrile, which was purified by column chromatography (EtOAc:Hexane, 80:20), yield 84%; mp 270-272° C. $^1$H NMR (DMSO-d$_6$): δ 7.97-8.00 (m, 4H), 8.05 (dd, J=1.8, 8.4 Hz, 2 H), 8.25 (dd, J=1.8, 8.1 Hz, 1H), 8.33-8.38 (m, 3H), 9.13 (d, J=1.8 Hz, 1H). MS (ESI) m/e (rel. int.): 281 (M$^+$, 100).

Phenyl[1,1']pyridyl[4',1"]phenyl-4,4"-bis-carboxamidine acetate salt (23c). The amidine was synthesized in two consecutive steps as described for compounds 5 and 10, starting with compound 24c, first by acetylation of the amidoxime to give the acetoxime intermediate, followed by direct reductive hydrolysis; mp 273-275° C. $^1$H NMR (D$_2$O/DMSO-d$_6$): δ 1.70 (s, 2.8×CH$_3$), 7.84-7.89 (m, 4H), 8.06-8.25 (m, 6H), 8.95 (s, 1H). MS (ESI) m/e (rel. int.): 316 (M$^+$, 100), 158 (98). $^{13}$H NMR (D$_2$O/DMSO-d$_6$, of hydrochloride salt): δ 165.9, 154.8, 148.4, 143.5, 142.2, 136.5, 134.2, 129.3, 129.0, 128.5, 127.9, 127.8, 127.7, 122.0. Anal. Calc. for C$_{19}$H$_{17}$N$_5$·2.8CH$_3$CO$_2$H·0.75H$_2$O: C %, 59.44; H %, 6.02; N %, 14.09. Found C %, 59.27; H %, 5.92; N %, 14.16.

Phenyl[1,1']pyridyl[4',1"]phenyl-4,4"-bis-N-hydroxycarboxamidine (24c). The bis-amidoxime was obtained from the corresponding bis-nitrile using the standard procedure in 97% yield; mp >300° C. $^1$H NMR (DMSO-d$_6$): δ 5.89 (br s, 4H), 7.79-7.81 (m, 6H), 8.08-8.23 (m, 4H), 9.03 (d, J=1.5 Hz, 1H), 9.74 (br s, 2H). $^{13}$C NMR (DMSO-d$_6$): δ 154.3, 150.4, 150.3, 147.2, 138.3, 136.8, 134.6, 133.7, 133.4, 132.8, 126.1, 125.9, 125.8, 125.5, 119.9. MS (ESI) m/e (rel. int.): 348 (M⁺, 52), 174 (100).

24c hydrochloride salt: mp 292-294° C. ¹H NMR (DMSO-d₆): δ 7.91 (dd, J=1.8, 7.8 Hz, 4H), 8.09 (d, J=8.7 Hz, 2 H), 8.27 (d, J=8.4 Hz, 1 H), 8.36-8.40 (m, 3H), 9.15 (d, J=1.8 Hz, 1 H), 9.21 (br s, 4H), 11.42 (br s, 2H). Anal. Calc. for $C_{19}H_{17}N_5O_2$-3.0HCl-1.0H₂O-0.3C₂H₅OH: C %, 48.18; H %, 4.90; N %, 14.33. Found C %, 48.18; H %, 4.74; N %, 14.18.

Phenyl[1,1']pyridyl[4',1"]phenyl-4,4"-bis-N-methoxycarboxamidine (25c). The bis-amidoxime was used to prepare the target compound using the standard procedure in 89% yield; mp 245-247° C. ¹H NMR (DMSO-d₆): δ 3.76 (s, 6H), 6.13 (br s, 4H), 7.78-7.84 (m, 6H), 8.08-8.23 (m, 4H), 9.03 (d, J=2.4 Hz, 1H). ¹³C NMR (DMSO-d₆): δ 154.3, 150.6, 150.5, 147.5, 138.8, 137.4, 134.9, 133.5, 133.0, 132.2, 126.4, 126.3, 126.1, 126.0, 120.2, 60.6. MS (ESI) m/e (rel. int.): 376 (M⁺, 100).

25c hydrochloride salt: mp 241-242° C. ¹H NMR (DMSO-d₆): δ 3.88 (s, 6H), 7.94 (dd, J=1.8, 8.7 Hz, 4H), 8.05 (dd, J=1.8, 8.7 Hz, 2H), 8.27 (d, J=8.7 Hz, 1H), 8.34-8.41 (m, 3H), 9.14 (d, J=2.4 Hz, 1H). Anal. Calc. for $C_{21}H_{21}N_5O_2$-3.0HCl-1.75H₂O-0.5C₂H₅OH: C %, 48.88; H %, 5.69; N %, 12.98. Found C %, 48.99; H %, 5.56; N %, 12.75.

Example 6

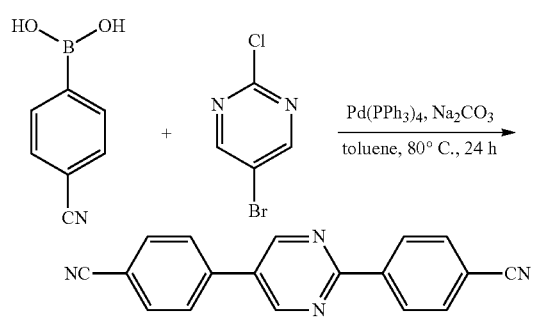

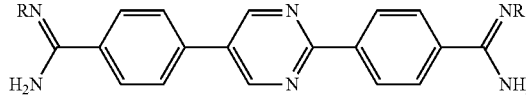

2,5-Bis-(4'-cyanophenyl)-pyrimidine (26). 2-Chloro-5-bromopyrimidine and p-cyanophenylboronic acid were reacted under the above-mentioned Suzuki coupling conditions to give the target dinitrile. Yield 91%, mp 305-306.5° C. (DMF). ¹H NMR (DMSO-d₆): δ 7.98-8.07 (m, 6H), 8.58 (s, 2H), 9.34 (s, 2H). ¹³C NMR (DMSO-d₆): δ 161.1, 155.5, 140.4, 137.8, 132.6, 132.3, 129.9, 128.0, 127.4, 118.06, 118.00, 113.0, 111.3. MS (ESI) m/e (rel. int.): 282 (M⁺, 100), 141 (10), 127 (80).

2,5-Bis-(4'-amidinophenyl)-pyrimidine (27). The same procedure described for preparation of 23a was used starting with 26. Yield 86%, mp >300° C. ¹H NMR (D₂O/DMSO-d₆): δ 7.91-8.00 (m, 6H), 8.54 (s, 2H), 9.26 (s, 2H). ¹³C NMR (D₂O/DMSO-d₆): δ 166.09, 166.00, 162.4, 156.3, 142.0, 139.3, 131.1, 130.3, 129.4, 129.0, 128.5, 128.0, 122.2. MS (ESI) m/e (rel. int.): 317 (M⁺+1, 100), 159 (45). Anal. Calc. for $C_{16}H_{16}N_6$-3.0HCl-0.25H₂O): C %, 50.24; H %, 4.57; N %, 19.53. Found C %, 50.33; H %, 4.80; N %, 19.47.

2,5-Bis-[4'-(N-hydroxyamidino)phenyl]-pyrimidine (28). The same procedure described for preparation of 3 was used starting with 26. Yield 97%, mp 290-292° C. ¹H NMR (DMSO-d₆): δ 5.71 (s, 4H), 7.84-7.87 (m, 6H), 8.42 (s, 2H), 9.23 (s, 2H), 9.58 (s, 2H). ¹³C NMR (DMSO-d₆): δ 161.6, 154.7, 150.2, 150.1, 136.9, 135.2, 133.7, 133.4, 130.2, 127.0, 126.0, 125.8, 125.3. MS (ESI) m/e (rel. int.): 349 (M⁺+1, 100), 332 (15), 315 (10), 282 (60).

2,5-Bis-[4'-(N-methoxyamidino)phenyl]-pyrimidine (29). The same procedure described for preparation of 4 was used starting with 28. Free base yield 64%, mp 217-218° C. ¹H NMR (DMSO-d₆): δ 3.76 (s, 6H), 6.19 (s, 4H), 7.83-7.88 (m, 6H), 8.43 (s, 2H), 9.28 (s, 2H). ¹³C NMR (DMSO-d₆): δ 161.6, 155.0, 150.5, 150.4, 137.4, 134.5, 134.3, 132.6, 130.3, 127.2, 126.3, 126.2, 125.9, 60.5. MS (ESI) m/e (rel. int.): 377 (M⁺+1, 100), 347 (30), 330 (25).

29 hydrochloride salt: mp 242-243° C. Anal. Calc. for $C_{20}H_{20}N_6O_2$-2.6HCl-0.75C₂H₅OH): C %, 51.18; H %, 5.37; N %, 16.66. Found C %, 51.35; H %, 5.46; N %, 16.44.

Example 7

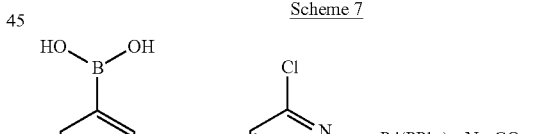

-continued

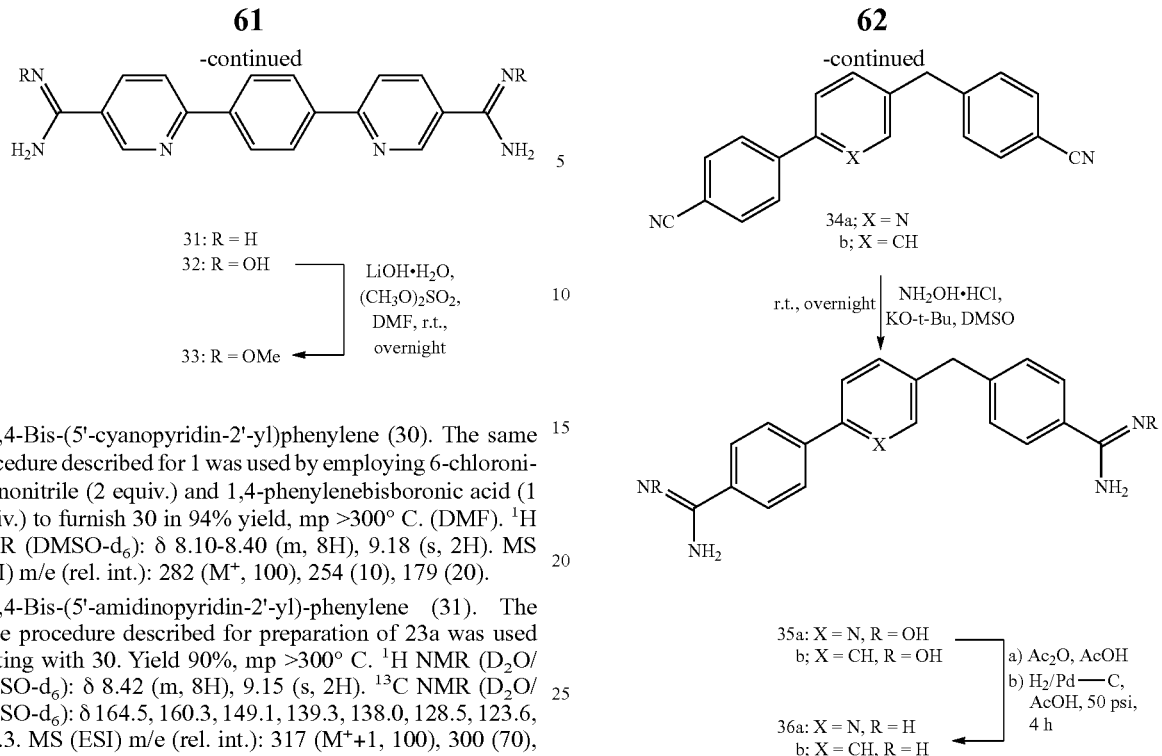

31: R = H
32: R = OH
33: R = OMe

LiOH·H₂O, (CH₃O)₂SO₂, DMF, r.t., overnight 1,4-Bis-(5'-cyanopyridin-2'-yl)phenylene (30). The same procedure described for 1 was used by employing 6-chloronicotinonitrile (2 equiv.) and 1,4-phenylenebisboronic acid (1 equiv.) to furnish 30 in 94% yield, mp >300° C. (DMF). $^1$H NMR (DMSO-d$_6$): δ 8.10-8.40 (m, 8H), 9.18 (s, 2H). MS (ESI) m/e (rel. int.): 282 (M$^+$, 100), 254 (10), 179 (20).

1,4-Bis-(5'-amidinopyridin-2'-yl)-phenylene (31). The same procedure described for preparation of 23a was used starting with 30. Yield 90%, mp >300° C. $^1$H NMR (D$_2$O/DMSO-d$_6$): δ 8.42 (m, 8H), 9.15 (s, 2H). $^{13}$C NMR (D$_2$O/DMSO-d$_6$): δ 164.5, 160.3, 149.1, 139.3, 138.0, 128.5, 123.6, 121.3. MS (ESI) m/e (rel. int.): 317 (M$^+$+1, 100), 300 (70), 283 (50), 273 (15), 246 (35). Anal. Calc. for C$_{18}$H$_{16}$N$_6$-4.0HCl): C %, 46.77; H %, 4.36; N %, 18.18. Found C %, 46.98; H %, 4.55; N %, 17.89.

1,4-Bis-[5'-(N-hydroxyamidinopyridin-2'-yl)]-phenylene (32). The same procedure described for preparation of 3 was used starting with 30. Yield 96%, mp >300° C. $^1$H NMR (DMSO-d$_6$): δ 5.88 (s, 4H), 8.03 (d, J=8.1 Hz, 2H), 8.13 (d, J=8.1 Hz, 2H), 8.23-8.36 (m, 4H), 8.99 (s, 2H), 9.75 (s, 2H). $^{13}$C NMR (DMSO-d$_6$): δ 155.3, 148.7, 146.4, 138.6, 133.6, 127.6, 126.6, 119.3. MS (ESI) m/e (rel. int.): 349 (M$^+$+1, 100), 334 (30), 282 (20).

1,4-Bis-[5'-(N-methoxyamidinopyridin-2'-yl)]phenylene (33). The same procedure described for preparation of 4 was used starting with 32. Free base yield 70%, mp 218-219° C. $^1$H NMR (DMSO-d$_6$): δ 3.78 (s, 6H), 6.29 (s, 4H), 8.05-8.15 (m, 4H), 8.26 (s, 4H), 8.95 (s, 2H). $^{13}$C NMR (DMSO-d$_6$): δ 155.7, 149.0, 146.8, 138.7, 134.3, 127.1, 126.9, 119.7, 60.8. MS (ESI) m/e (rel. int.): 377 (M$^+$+1, 100), 330 (10), 189 (25).

Hydrochloride salt of 33. mp 251-253° C. Anal. Calc. for C$_{20}$H$_{20}$N$_6$O$_2$-4.0HCl-2.0H$_2$O-0.2C$_2$H$_5$OH): C %, 43.17; H %, 5.18; N %, 14.80. Found C %, 43.32; H %, 5.04; N %, 14.42.

Example 8

Scheme 8

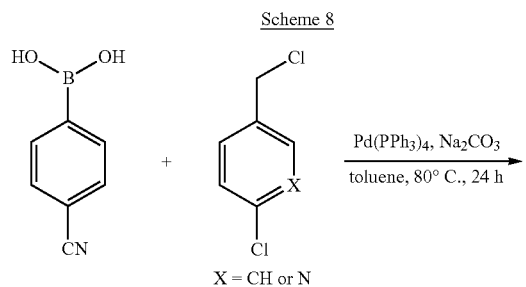

X = CH or N

Pd(PPh₃)₄, Na₂CO₃
toluene, 80° C., 24 h

-continued

[structure 34a/b]

34a; X = N
b; X = CH r.t., overnight
NH₂OH·HCl, KO-t-Bu, DMSO

[structure 35]

35a: X = N, R = OH
b; X = CH, R = OH a) Ac₂O, AcOH
b) H₂/Pd—C, AcOH, 50 psi, 4 h 36a: X = N, R = H
b; X = CH, R = H 2-(4'-Cyanophenyl)-5-(4"-cyanobenzyl)pyridine (34a). 2-Chloro-5-(chloromethyl)-pyridine (1 equiv.) and p-cyanophenylboronic acid (2 equiv.) were reacted under the above-mentioned Suzuki coupling conditions to give the target dinitrile 34a. Yield 83%, mp 187-187.5° C. $^1$H NMR (DMSO-d$_6$): δ 4.13 (s, 2H), 7.50 (d, J=8.4 Hz, 2H), 7.74-7.79 (m, 3H), 7.91 (d, J=8.4 Hz, 2H), 7.99 (d, J=7.8 Hz, 1H), 8.21-8.24 (m, 2H), 8.65 (s, 1H). $^{13}$C NMR (DMSO-d$_6$): δ 152.2, 150.0, 146.2, 142.5, 137.6, 135.8, 132.7, 132.5, 129.7, 127.0, 121.0, 118.7, 111.2, 109.2, 37.5. MS (ESI) m/e (rel. int.): 296 (M$^+$+1, 100).

2-[4-(N-Hydroxyamidino)phenyl]-5-[4"-(N-hydroxyamidino)benzyl]pyridine (35a). The same procedure described for the preparation of 3 was used starting with 34a. Yield 99%, mp 205-206° C. $^1$H NMR (DMSO-d$_6$): δ 4.01 (s, 2H), 5.77 (s, 2H), 5.85 (s, 2H), 7.28 (d, J=8.4 Hz, 2H), 7.60 (d, J=8.4 Hz, 2H), 7.68-7.78 (m, 3H), 7.90 (d, J=8.1 Hz, 1H), 8.05 (d, J=8.4 Hz, 2H), 8.59 (d, J=1.8 Hz, 1H), 9.57 (s, 1H), 9.71 (s, 1H). $^{13}$C NMR (DMSO-d$_6$): δ 153.4, 150.7, 150.5, 149.6, 141.3, 138.8, 137.2, 135.6, 133.5, 131.3, 128.4, 126.0, 125.7, 125.6, 120.0, 37.4. MS (ESI) m/e (rel. int.): 362 (M$^+$+1, 60), 181 (100).

2-(4'-Amidinophenyl)-5-(4"-amidinobenzyl)pyridine acetate salt (36a). The same procedure described for the preparation of 5 was used starting with 35a. Yield 80%, mp 258-259° C. $^1$H NMR (D$_2$O/DMSO-d$_6$): δ 1.80 (s, 3×CH₃), 4.12 (s, 2H), 7.46 (d, J=7.2 Hz, 2H), 7.72-7.78 (m, 3H), 7.87-7.98 (m, 3H), 8.18 (d, J=7.8 Hz, 2H), 8.64 (s, 1H). MS (ESI) m/e (rel. int.): 330 (M$^+$+1, 50), 165 (100). Anal. Calc. for C$_{20}$H$_{19}$N$_5$-3.0CH$_3$CO$_2$H-0.45H$_2$O): C %, 60.32; H %, 6.21; N %, 13.53. Found C %, 59.96; H %, 6.24; N %, 13.92.

1-(4'-Cyanophenyl)-4-(4"-cyanobenzyl)phenylene (34b). 1-Chloro-4-(chloromethyl)benzene (1 equiv.) and p-cyanophenylboronic acid (2 equiv.) were reacted under the above-mentioned Suzuki coupling conditions to give the target dinitrile 34b.

1-[4-(N-Hydroxyamidino)phenyl]-4-[4''-(N-hydroxyamidino)benzyl]phenylene (35b). The same procedure described for the preparation of 3 was used starting with 34b.

1-(4'Amidinophenyl)-4-(4''-amidinobenzyl)phenylene acetate salt (36b). The same procedure described for the preparation of 5 was used starting with 35b.

Example 9

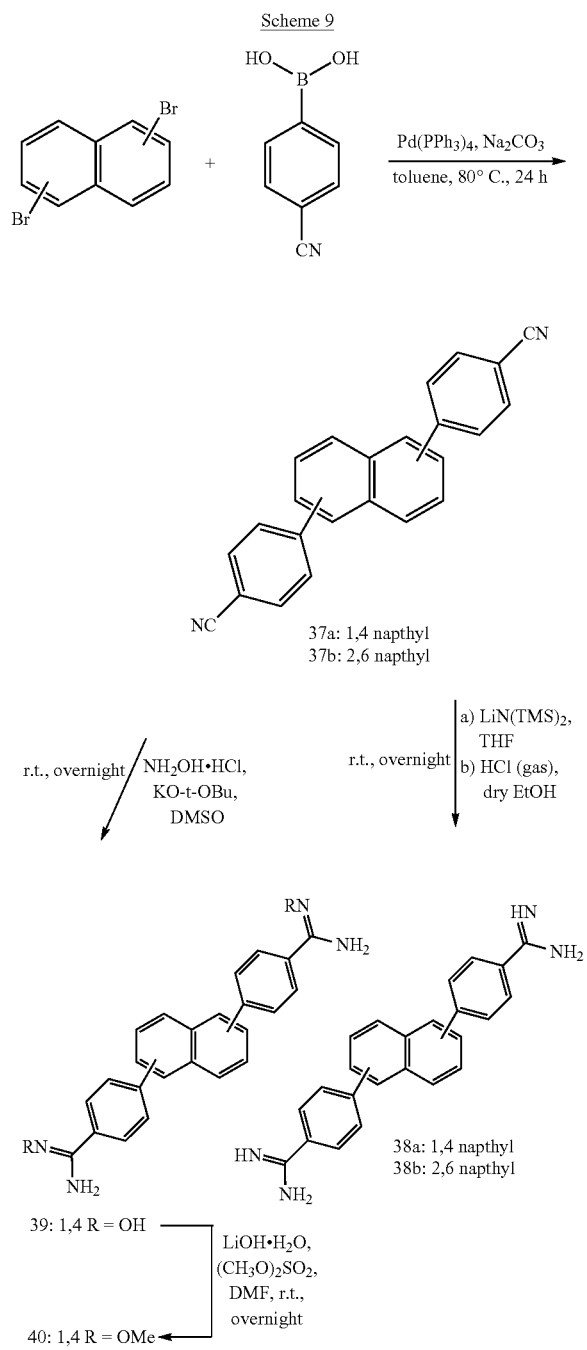

Scheme 9

37a: 1,4 napthyl
37b: 2,6 napthyl a) LiN(TMS)$_2$, THF
b) HCl (gas), dry EtOH r.t., overnight / NH$_2$OH·HCl, KO-t-OBu, DMSO r.t., overnight 38a: 1,4 napthyl
38b: 2,6 napthyl 39: 1,4 R = OH
40: 1,4 R = OMe LiOH·H$_2$O, (CH$_3$O)$_2$SO$_2$, DMF, r.t., overnight Phenyl[1,1]naphthyl[4',1'']phenyl-4,4''-bis-carbonitrile (37a). The bis-cyano compound was prepared through the coupling of 1,4-dibromonaphthalene and p-cyanophenylboronic acid using the standard conditions. The crude reaction product was recrystallized from n-butanol to give the dinitrile 37a in 73% yield; mp 239-240° C. $^1$H NMR (DMSO-d$_6$): δ 7.56-7.59 (m, 4H), 7.73 (d, J=8.1 Hz, 4H), 7.79-7.82 (m, 2H), 8.01-8.03 (d, J=8.1 Hz, 4H). $^{13}$C NMR (DMSO-d$_6$): δ 144.3, 138.0, 132.0, 130.4, 126.5, 127.4, 126.2, 125.1, 118.2, 110.2. MS (ESI) m/e (rel. int.): 330 (M$^+$, 100). Anal. Calc. for C$_{24}$H$_{14}$N$_2$: C %, 87.24; H %, 4.27. Found C %, 87.41; H %, 4.07.

Phenyl[1,1]napthyl[4',1'']phenyl-4,4''-bis-amidine (38a). The same procedure described for the preparation of 23a was used starting with 37a. mp >300° C. $^1$H NMR (DMSO-d$_6$): δ 6.75 (br s, 6H), 7.51-7.57 (m, 8H), 7.85-7.88 (m, 2H), 7.94 (dd, J=1.8, 8.4 Hz, 4H). MS (ESI) m/e (rel. int.): 365 (M$^+$, 32), 183 (100). Anal. Calc. for C$_{24}$H$_{20}$N$_4$·2.0HCl·0.25H$_2$O: C %, 65.23; H %, 5.13; N %, 12.76. Found C %, 65.31; H %, 5.19; N %, 12.52.

Phenyl[1,1']naphthyl-[4',1'']phenyl-4,4''-bis-N-hydroxycarboxamidine (39). The same procedure described for the preparation of 3 was used starting with 37a. Yield 94%; mp 216-217° C. $^1$H NMR (DMSO-d$_6$): δ 5.90 (br s, 4H), 7.51-7.54 (m, 10H), 7.83-7.90 (m, 4H), 9.72 (br s, 2H). MS (ESI) m/e (rel. int.): 397 (M$^+$, 64), 199 (100).

39 hydrochloride salt: mp 175-176° C. $^1$H NMR (DMSO-d$_6$): δ 7.57-7.60 (m, 4H), 7.74-7.83 (m, 6H), 7.94-7.96 (m, 4H), 9.18 (br s, 4H), 11.40 (br s, 2H), 13.18 (br s, 2H). Anal. Calc. for C$_{24}$H$_{20}$N$_4$O$_2$·2.0HCl·0.75H$_2$O·1.0C$_2$H$_5$OH: C %, 59.03; H %, 5.62; N %, 10.59. Found C %, 58.95; H %, 5.37; N %, 10.49.

Phenyl[1,1']naphthyl-[4',1'']phenyl-4,4''-bis-N-methoxycarboxamidine (40). The same procedure described for the preparation of 4 was used starting with 39. Yield 85%; mp 198-200° C. $^1$H NMR (DMSO-d$_6$): δ 3.77 (s, 6H), 6.16 (s, 4H), 7.51-7.54 (m, 8H), 7.81-7.89 (m, 6H). $^{13}$C NMR (DMSO-d$_6$): δ 150.9, 140.9, 138.8, 131.8, 131.1, 129.7, 126.5, 126.0, 125.8, 60.7. MS (ESI) m/e (rel. int.): 425 (M$^+$, 100).

40 hydrochloride salt: mp 226-228° C. $^1$H NMR (DMSO-d$_6$): δ 3.89 (s, 6H), 7.56-7.59 (m, 4H), 7.70 (dd, J=1.8, 8.7 Hz, 4H), 7.80-7.84 (m, 2H), 7.96 (dd, J=1.8, 8.7 Hz, 4H), 8.62 (br s, 4H). Anal. Calc. for C$_{26}$H$_{24}$N$_4$O$_2$·2.0HCl·0.5C$_2$H$_5$OH: C %, 62.30; H %, 5.61; N %, 10.76. Found C %, 62.15; H %, 5.44; N %, 10.54.

Phenyl[1,2']naphthyl[6',1'']phenyl-4,4''-bis-carbonitrile (37b). Adopting the same procedure used in the preparation of 37a starting with 2,6-dibromonaphthalene, the bisnitrile was obtained in 79% yield; mp 270-272° C. $^1$H NMR (DMSO-d$_6$): δ 7.93-7.96 (m, 6H), 8.03-8.05 (m, 4H), 8.14 (d, J=8.4 Hz, 2H), 8.37 (3, 2H). MS (ESI) m/e (rel. int.): 330 (M$^+$, 100). Anal. Calc. for C$_{24}$H$_{14}$N$_2$: C %, 87.24; H %, 4.27. Found C %, 86.98; H %, 4.53.

Phenyl[1,2']naphthyl[6',1'']phenyl-4,4''-bis-amidine (38b). The same procedure described for the preparation of 23a was used starting with 37b, the target compound was obtained; mp >300° C. $^1$H NMR (DMSO-d$_6$): δ 7.99-8.03 (m, 6H), 8.11-8.19 (m, 6H), 8.46 (s, 2H), 9.22 (br s, 4H), 9.48 (br s, 4H). MS (ESI) m/e (rel. ab.): 365 (M$^+$, 100), 331 (24). Anal. Calc. for C$_{24}$H$_{20}$N$_4$·2.0HCl·0.75H$_2$O·0.3C$_2$H$_5$OH: C, 63.58; H, 5.48; N, 12.05. Found C, 73.70; H, 5.16; N, 11.75.

Example 10

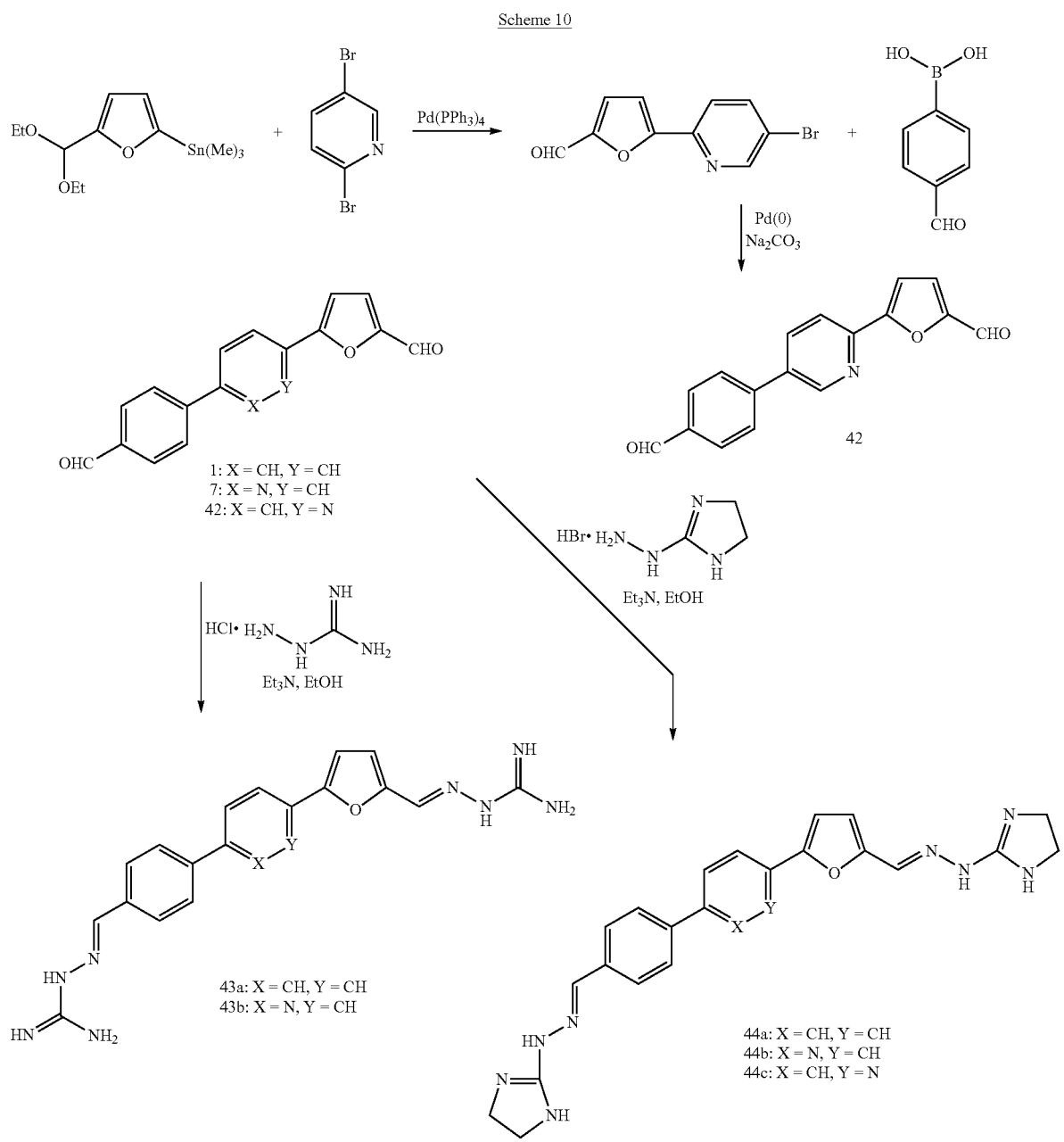

Scheme 10

5-[4'-(Hydrazono)-biphenyl-4-yl]-furan-2-hydrazone (43a). A mixture of compound 1 (1 mmol), aminoguanidine hydrochloride (4 mmol), and triethylamine (4 mmol) in absolute ethanol (50 mL) was heated at reflux for overnight. The formed precipitate was filtered, washed with water, dried to give 43a in 66% yield, mp 294-295° C. $^1$H NMR (DMSO-$d_6$); δ 6.00 (br s, 4H), 6.60 (br s, 4H), 6.84 (d, J=3.6 Hz, 1H), 7.12 (d, J=3.6 Hz, 1H), 7.67-7.86 (m, 8H), 7.93 (s, 1H), 8.10 (s, 1H). (43a hydrochloride salt); mp 276-278° C. $^1$H NMR (DMSO-$d_6$); δ 7.18 (d, J=3.6 Hz, 1H), 7.26 (d, J=3.6 Hz, 1H), 7.70 (br s, 8H), 7.82-7.99 (m, 8H), 8.15 (s, 1H), 8.23 (s, 1H), 12.07 (s, 1H), 12.12 (s, 1H). MS (ESI) m/e (rel. int.): 389 (M$^+$+1, 100), 333 (20), 247 (10). Anal. Calc. for $C_{20}H_{20}N_8O$·2.0HCl·1.1H$_2$O·0.5EtOH: C %, 50.10; H %, 5.45; N %, 22.27. Found C %, 50.30; H %, 5.17; N %, 21.90.

5-{4'-[2-(4,5-Dihydro-1H-imidazol-2-yl)-hydrazono]-biphenyl-4-yl}-furan-2-(4,5-dihydro-1H-imidazol-2-yl)-hydrazone (44a). The same procedure described for the preparation of 43a was used by employing 2-hydrazino-2-imidazoline hydrobromide instead of aminoguanidine hydrochloride. Yield 93%, mp 299-301° C. $^1$H NMR (DMSO-$d_6$); δ 6.50 (br s, 2H), 6.70 (br s, 1H), 6.74 (d, J=3.6 Hz, 1H), 6.87 (br s, 1H), 7.09 (d, J=3.6 Hz, 1H), 7.69-7.85 (m, 8H), 7.89 (s, 1H), 8.02 (s, 1H). $^{13}$C NMR; δ 157.7, 157.4, 154.6, 148.0, 147.4, 140.9, 138.8, 137.5, 132.5, 128.6, 127.9, 127.0, 126.6, 124.5, 117.0, 108.6, 42.6.

(44a hydrochloride salt); mp 302-304° C. $^1$H NMR (DMSO-$d_6$); δ 3.74 (s, 8H), 7.16 (d, J=3.6 Hz, 1H), 7.27 (d, J=3.6 Hz, 1H), 7.85-7.95 (m, 8H), 8.25 (s, 1H), 8.33 (s, 1H), 8.67 (br s, 4H), 12.84 (br s, 1H), 12.90 (br s, 1H). Anal. Calc. for $C_{24}H_{24}N_8O \cdot 2.0HCl \cdot 1.5H_2O$: C %, 53.33; H %, 5.40; N %, 20.73. Found C %, 53.35; H %, 5.33; N %, 20.37.

5-[4-(2-Hydrazono)-pyridin-5-yl-phenyl]-furan-2-hydrazone (43b). The same procedure described for the preparation of 43a was used starting with 7. Yield 83%, mp 253-255° C. $^1$H NMR (DMSO-$d_6$): δ 5.65 (br s, 4H), 6.02 (br s, 4H), 6.79 (d, J=3.6 Hz, 1H), 7.22 (d, J=3.6 Hz, 1H), 7.79 (d, J=8.4 Hz, 2H), 7.90 (s, 1H), 8.04-8.14 (m, 5H), 9.07 (s, 1H).

(43b hydrochloride salt); mp 242-244° C. $^1$H NMR (DMSO-$d_6$); δ 7.21 (d, J=3.6 Hz, 1H), 7.41 (d, J=3.6 Hz, 1H), 7.83 (br s, 8H), 8.04 (d, J=8.4 Hz, 2H), 8.18 (s, 1H), 8.22-8.36 (m, 5H), 9.22 (s, 1H), 12.18 (s, 1H), 12.27 (s, 1H). $^{13}$C NMR (DMSO-$d_6$); δ 155.1, 155.0, 154.3, 152.5, 149.2, 146.9, 145.4, 139.5, 136.7, 134.5, 133.1, 128.5, 127.2, 124.9, 121.2, 117.5, 110.6, 99.9. Anal. Calc. for $C_{19}H_{19}N_9O \cdot 3.0HCl \cdot 1.5H_2O \cdot 0.7EtOH$: C %, 43.90; H %, 5.27; N %, 22.58. Found C %, 43.99; H %, 4.95; N %, 22.28.

5-{(4-[2-(4,5-Dihydro-1H-imidazol-2-yl)-hydrazono]-pyridin-5-yl-phenyl}-furan-2-(4,5-dihydro-1H-imidazol-2-yl)-hydrazone (44b). The same procedure described for the preparation of 44a was used starting with 7. Yield 88%, mp 281-283° C. $^1$H NMR (DMSO-$d_6$): δ 3.42 (s, 8H), 6.58 (br s, 2H), 6.76 (d, J=3.6 Hz, 1H), 6.78 (s, 1H), 6.92 (s, 1H), 7.23 (d, J=3.6 Hz, 1H), 7.80 (d, J=8.4 Hz, 2H), 7.90 (s, 1H), 8.04-8.18 (m, 5H), 9.09 (s, 1H). $^{13}$C NMR (DMSO-$d_6$); δ 1166.0, 165.5, 152.6, 149.9, 144.7, 143.8, 137.6, 137.1, 134.0, 131.2, 126.6, 126.2, 124.5, 119.9, 116.5, 111.0, 109.5, 42.3, 41.7.

(44b hydrochloride salt); mp 300-302° C. $^1$H NMR (DMSO-$d_6$); δ 3.78 (s, 8H), 7.20 (d, J=3.6 Hz, 1H), 7.41 (d, J=3.6 Hz, 1H), 7.99 (d, J=8.4 Hz, 2H), 8.19-8.35 (m, 6H), 8.71 (br s, 4H), 9.22 (s, 1H), 12.89 (s, 1H), 13.0 (s, 1H). Anal. Calc. for $C_{23}H_{21}N_9O \cdot 3.0HCl \cdot 3.0H_2O \cdot 0.25EtOH$: C %, 45.94; H %, 5.17; N %, 20.51. Found C %, 45.94; H %, 5.33; N %, 20.17.

5-(4-Bromopyridin-2-yl)-furan-2-carbaldehyde (41). The same procedure employed for the preparation of 25 was adopted using 2,5-dibromopyridine and (5-diethoxymethyl-furan-2-yl)-trimethyl-stannane followed by acid hydrolysis with 2M HCl. Yield 58%; mp 105-106° C. $^1$H NMR (DMSO-$d_6$); δ 7.42 (d, J=3.9 Hz, 1H), 7.69 (d, J=3.9 Hz, 1H), 7.88 (d, J=8.4 Hz, 2H), 8.22 (dd, J=2.1, 8.4 Hz, 1H), 8.81 (d, J=2.1 Hz, 1H), 9.68 (s, 1H). $^{13}$C NMR (DMSO-$d_6$); δ 178.55, 156.27, 152.46, 150.81, 145.75, 140.10, 124.54, 121.59, 120.40, 111.71. Anal. Calc. for $C_{10}H_6BrNO_2$: C %, 47.65; H %, 2.39. Found C %, 47.79; H %, 2.46.

5-[5-(4-Formylphenyl)-pyridin-2-yl]-furan-2-carboxaldehyde (42). The same procedure described for 12 was used by employing compound 41 (1 equiv.) and 4-formylphenyl boronic acid (1 equiv.). Yield 91%, mp 217-219° C. $^1$H NMR (DMSO-$d_6$); δ 7.46 (d, J=3.6 Hz, 1H), 7.71 (d, J=3.6 Hz, 1H), 8.03-8.05 (m, 5H), 8.37 (dd, J=1.8, 8.4 Hz, 1H), 9.11 (d, J=1.8 Hz, 1H), 9.69 (s, 1H), 10.07 (s, 1H). Anal. Calc. for $C_{17}H_{11}NO_3$: C %, 73.63; H %, 3.99. Found C %, 73.51; H %, 4.23.

5-{4-[5-(4,5-Dihydro-1H-imidazol-2-yl)-hydrazono]-pyridin-2-yl-phenyl}-furan-2-(4,5-dihydro-1H-imidazol-2-yl)-hydrazone (44c). The same procedure described for the preparation of 44a was used starting with 42. Yield 75%, mp 262-264° C.

(44c hydrochloride salt); mp 260-262° C. $^1$H NMR (DMSO-$d_6$); δ 3.75 (s, 8H), 7.22 (d, J=3.6 Hz, 1H), 7.39 (d, J=3.6 Hz, 1H), 7.92-8.05 (m, 5H), 8.32-8.35 (m, 3H), 8.74 (br s, 4H), 9.04 (s, 1H), 12.95 (br s, 2H), 13.08 (br s, 1H). MS (ESI) m/e (rel. int.): 442 (M$^+$+1, 90), 332 (100), 221 (30). Anal. Calc. for $C_{23}H_{23}N_9O \cdot 3.0HCl \cdot 4.5H_2O$: C %, 43.71; H %, 5.58; N %, 19.95. Found C %, 43.50; H %, 5.42; N %, 20.07.

Example 11

Scheme 11

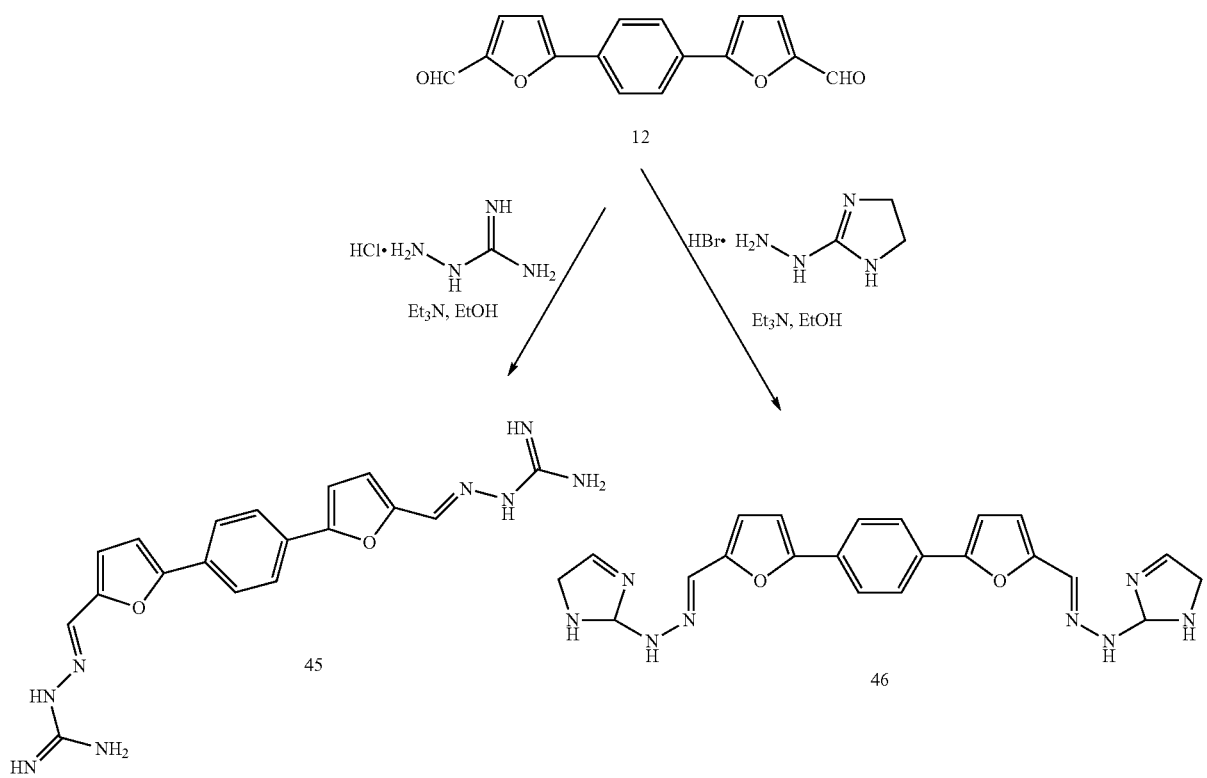

5-(4-(2-Hydrazono)-furan-5-yl-phenyl)-furan-2-hydrazone (45). Yield 89.7%, mp 273-275° C. $^1$H NMR (DMSO-$d_6$); δ 7.90 (s, 2H), 7.78 (s, 4H), 7.07 (d, J=3.6 Hz, 2H), 6.77 (d, J=3.6 Hz, 2H), 5.95 (br s, 4H), 5.69 (br s, 4H). $^{13}$C NMR (DMSO-$d_6$); δ 159.7, 152.6, 151.6, 133.8, 128.8, 123.9, 111.7, 108.3.

(45 hydrochloride salt); mp 278-280° C. $^1$H NMR (DMSO-$d_6$); δ 12.05 (s, 2H), 8.14 (s, 2H), 7.93 (s, 4H), 7.76 (br s, 8H), 7.27 (d, J=3.6 Hz, 2H), 7.18 (d, J=3.6 Hz, 2H). MS (ESI) m/e (rel. int.): 379 (M$^+$+1, 100), 307 (5), 190 (70). Anal. Calc. for $C_{18}H_{18}N_8O_2$-2.0HCl-1.25H$_2$O-0.7EtOH: C %, 46.12; H %, 5.29; N %, 22.19. Found C %, 45.90; H %, 4.95; N %, 21.90.

5-{4-[2-(4,5-Dihydro-1H-imidazol-2-yl)-hydrazono]-furan-5-yl-phenyl}-furan-2-(4,5-dihydro-1H-imidazol-2-yl)-hydrazone (46). Yield 90%, mp >300° C. $^1$H NMR (DMSO-$d_6$); δ 7.88 (s, 2H), 7.78 (s, 4H), 7.07 (d, J=3.6 Hz, 2H), 6.72 (d, J=3.6 Hz, 2H), 6.63 (br s, 2H), 6.56 (br s, 2H), 3.42 (s, 8H). $^{13}$C NMR (DMSO-$d_6$); δ 164.3, 152.7, 151.5, 135.1, 128.8, 124.0, 116.8, 112.0, 108.4, 42.1.

(46 hydrochloride salt); mp 294-296° C. $^1$H NMR (DMSO-$d_6$); δ 12.87 (s, 2H), 8.69 (br s, 4H), 8.24 (s, 2H), 7.93 (s, 4H), 7.28 (d, J=3.6 Hz, 2H), 7.16 (d, J=3.6 Hz, 2H), 3.73 (s, 8H). Anal. Calc. for $C_{22}H_{22}N_8O_2$-2.0HCl-2.25H$_2$O-0.75EtOH: C %, 48.87; H %, 5.71; N %, 19.41. Found C %, 48.72; H %, 5.36; N %, 19.19.

Example 12

(0.71 g, 2.4 mmol), triethylamine (0.74 g, 7.2 mmol) and finally mercury(II)chloride (0.73 g, 2.6 mmol). The suspension was kept stirring at room temperature for 24 h. The reaction, diluted with CH$_2$Cl$_2$ and Na$_2$CO$_3$ solution, was filtered through a pad of Celite. The organic layer was washed with water (3×) followed by brine and then dried over anhydrous Na$_2$SO$_4$. After evaporating the solvent to dryness the obtained residue was recrystallized from CH$_2$Cl$_2$/MeOH giving a creamy white solid, yield % 79; mp >300° C. $^1$H NMR (DMSO-$d_6$): δ 1.50, 1.59 (2s, 36H), 7.56-7.70 (m, 12H), 10.39 (br s, 2H), 11.65 (br s, 2H). Anal. Calc. for $C_{40}H_{52}N_6O_8$: C %, 64.49; H %, 7.03. Found C %, 64.31; H %, 6.85.

4,4''-Bis-guanidino-[1,1';4',1'']terphenyl (48). The N',N''-di-BOCguanidine (0.45 g, 0.60 mmol) was dissolved in CH$_2$Cl$_2$ (10 mL), diluted with dry EtOH (15 mL) and the chilled solution was saturated with dry HCl. The reaction was then kept stirring at room temperature for 3 days (drying tube), when by the product started forming a precipitate over time. After evaporating the solvent to dryness, the residue was washed with ether multiple times and was dried under vacuum at 50-60° C. over night to give whitish yellow solid of the bis-guanidine dihydrochloride; mp >300° C. $^1$H NMR (DMSO-$d_6$): δ 7.85 (dd, J=1.5, 8.4 Hz, 4H), 7.92 (d, J=1.2 Hz, 4H), 8.00 (dd, J=1.5, 8.4 Hz, 4H), 9.09 (br s, 4H), 11.25 (br s, 2H). $^{13}$C NMR (DMSO-$d_6$): δ 155.98, 138.35, 137.32, 135.00, 127.79, 127.22, 124.79. MS (ESI) m/e (rel. int.): 344 (M$^+$, 6), 173 (100). Anal. Calc. for $C_{20}H_{20}N_6$-2.0HCl-

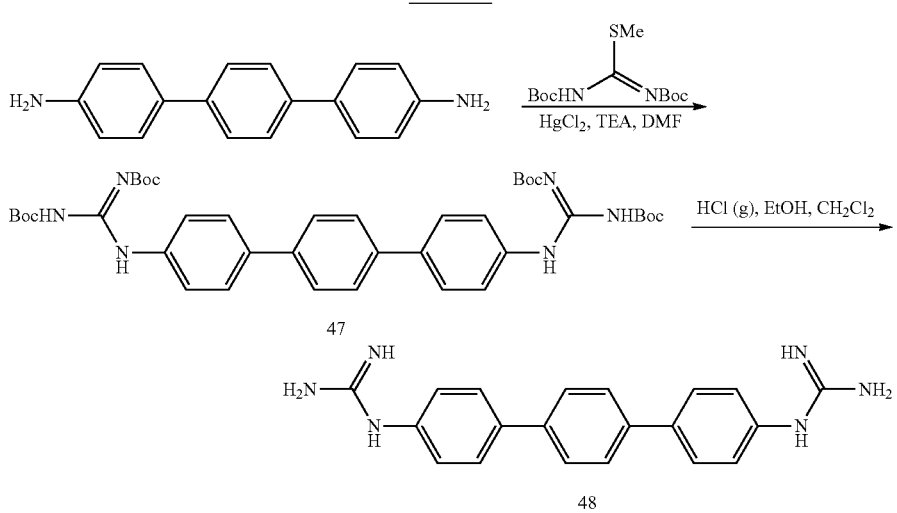

Scheme 12

4,4''-Bis(N',N''-t-butoxycarbonyl)-guanidino-[1,1';4',1''] terphenyl (47). To a solution of 4,4''-diamino-[1,1';4',1'']terphenyl (0.30 g, 1.15 mmol) in anhydrous DMF (10 mL) was added 1,3-bis(tert-butoxycarbonyl)-2-methylthiopseudourea 1.0H$_2$O-0.2C$_2$H$_5$OH: C %, 55.11; H %, 5.71; N %, 18.90. Found C %, 55.39; H %, 5.50; N %, 18.71.

Example 13

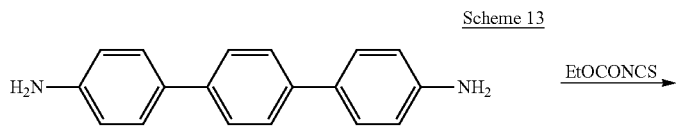

Scheme 13

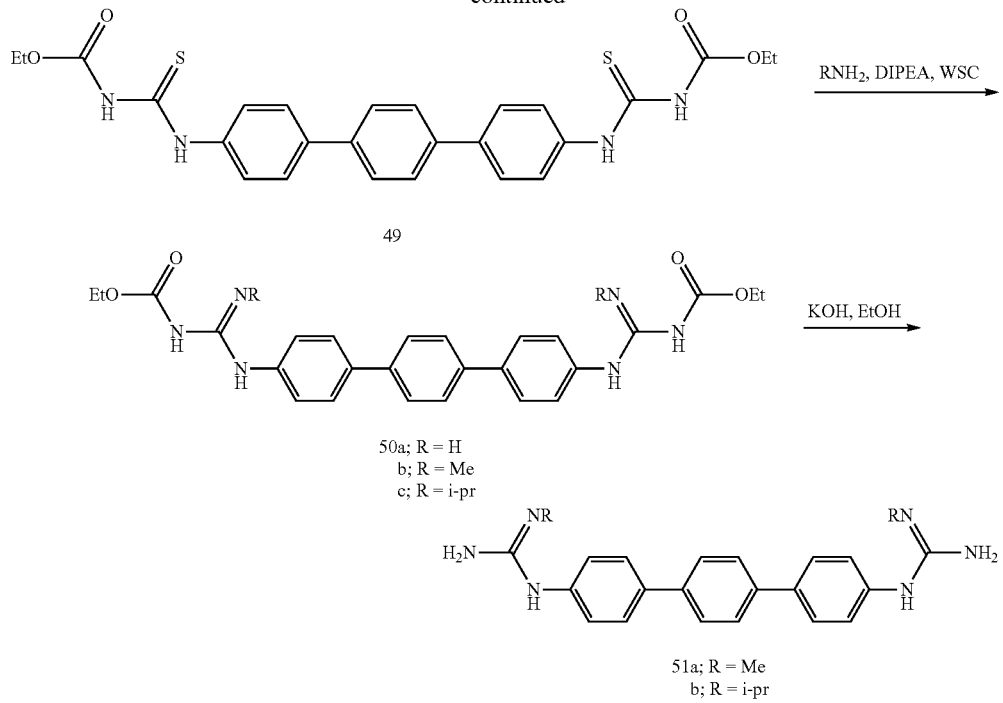

49

50a; R = H
b; R = Me
c; R = i-pr

51a; R = Me
b; R = i-pr 4,4''-Bis-(N'-ethoxycarbonylthiourea)-[1,1';4',1'']terphenyl (49). A solution of 4,4''-diamino-[1,1';4',1'']terphenyl (0.50 g, 1.92 mmol) in CH$_2$Cl$_2$ (10 mL), added to which ethyl isothiocyanatoformate (0.55 g, 4.22 mmol), was stirred at room temperature for 24 h. After flash chromatography, the reaction was diluted with hexane and the precipitate formed was collected and dried to yield the bis-carbamoylthiourea as a white solid yield % 89; mp >300° C. $^1$H NMR (DMSO-d$_6$): δ 1.26 (t, J=7.2 Hz, 6H), 4.22 (q, J=7.2 Hz, 4H), 7.70-7.79 (m, 12H), 11.29 (br s, 2H), 11.61 (br s, 2H). MS (ESI) m/e (rel. int.): 522 (M$^+$, 13), 344 (100), 328 (63). Anal. Calc. for C$_{26}$H$_{26}$N$_4$O$_4$S$_2$: C %, 59.75; H %, 5.01. Found C %, 49.58; H %, 5.23.

4,4''-Bis(N'-ethoxycarbonyl)-guanidino-[1,1';4',1'']terphenyl (50a). A stirred solution of carbamoyl thiourea (0.80 g, 1.53 mmol), 0.5 M ammonia solution in dioxane (11.7 mL, 6.12 mmol), and diisopropylethylamine (1.18 g, 9.18 mmol) in anhydrous DMF (10 mL) was cooled to 0° C. EDCl (1.17 g, 6.12 mmol) was added, and the solution was stirred at room temperature over night. The reaction mixture poured onto ice/water, the solid collected by vacuum filtration. Finally, the carbamoylguanidine was crystallized from EtOH, yield % 67; mp >300° C. $^1$H NMR (DMSO-d$_6$): δ 1.17 (t, J=6.9 Hz, 6H), 3.98 (q, J=6.9 Hz, 4H), 7.53-7.71 (m, 16H), 9.05 (br s, 2H). Anal. Calc. for C$_{26}$H$_{28}$N$_6$O$_4$-0.2C$_2$H$_5$OH: C %, 63.70; H %, 5.91; N %, 16.88. Found C %, 63.66; H %, 5.71; N %, 16.65.

4,4''-Bis(N'-ethoxycarbonyl-N''-methyl)-guanidino-[1,1';4',1'']terphenyl (50b). A stirred solution of carbamoyl thiourea (1.00 g, 1.91 mmol), methylamine hydrochloride (0.51 mL, 7.65 mmol), and diisopropylethylamine (1.48 g, 11.48 mmol) in anhydrous CH$_2$Cl$_2$ (10 mL) was cooled to 0° C. EDCl (1.46 g, 7.65 mmol) was added, and the solution was stirred at room temperature over night. The reaction mixture was washed with water (3×100 mL), followed by brine and dried over anhydrous Na$_2$SO$_4$. The residue remaining after removal of the solvent was crystallized from EtOH/water, yield % 82; mp 297-299° C. $^1$H NMR (DMSO-d$_6$): δ 1.15 (t, J=7.2 Hz, 6H), 3.32 (s, 6H), 3.95 (q, J=7.2 Hz, 4H), 7.45 (br s, 4H), 7.68-7.75 (m, 12H). $^{13}$C NMR (DMSO-d$_6$): δ 163.01, 158.53, 138.25, 137.50, 135.41, 126.76, 126.66, 124.14, 59.60, 28.17, 14.54. MS (ESI) m/e (rel. int.): 517 (M$^+$, 30), 259 (100). Anal. Calc. for C$_{28}$H$_{32}$N$_4$O$_4$-0.25C$_2$H$_5$OH: C %, 64.81; H %, 6.39; N %, 15.91. Found C %, 64.84; H %, 6.20; N %, 15.82.

4,4''-Bis(N'-methyl)-guanidino-[1,1';4',1'']terphenyl (51a). The substituted guanidine (0.5 g, 0.96 mmol) was suspended in EtOH (10 mL). 1N KOH 9.6 mL, 9.6 mmol) was then added and the reaction mixture was kept stirring over night maintaining the temperature at 55-60° C. The reaction mixture was diluted with water and the solid formed was collected by filtration, washed multiple times with water and recrystallized from aqueous EtOH to give a tan white solid, yield % 75; mp 243-244° C. $^1$H NMR (DMSO-d$_6$): δ 2.67 (s, 6H), 5.35 (br s, 6H), 6.87 (d, J=8.4 Hz, 4H), 7.53 (d, J=8.4 Hz, 4H), 7.64 (s, 4H). $^{13}$C NMR (DMSO-d$_6$): δ 152.2, 149.8, 138.2, 131.3, 126.5, 126.0, 123.2, 27.5. MS (ESI) m/e (rel. int.): 373 (M$^+$, 6), 187 (100).

51a Hydrochloride salt. The free base was dissolved in dry EtOH (20 mL) and the solution was chilled in an ice-bath. After passing HCl gas for 10 min, the reaction was concentrated under reduced pressure and then diluted with ether. The precipitate formed was collected by filtration; mp 211-214° C. $^1$H NMR (DMSO-d$_6$): δ 2.83, 2.85 (2 s, 6H), 7.33 (d, J=8.4 Hz, 4H), 7.77-7.80 (m, 8H), 7.96 (br s, 4H), 10.02 (br s, 4H). Anal. Calc. for C$_{22}$H$_{24}$N$_6$-2.0HCl-1.25H$_2$O-0.3C$_2$H$_5$OH: C %, 56.34; H %, 6.33; N %, 17.42. Found C %, 56.69; H %, 6.07; N %, 17.05.

4,4''-Bis(N'-ethoxycarbonyl-N''-isopropyl)-guanidino-[1,1';4',1'']terphenyl (50c). The same procedure described for the preparation of 50b was used by employing isopropylamine instead of methylamine. Yield % 89; mp >300° C. $^1$H NMR (DMSO-d$_6$): δ 1.11-1.18 (m, 18H), 3.94 (q, J=7.2 Hz, 4H), 4.01-4.14 (m, 2H), 7.45 (d, J=7.8 Hz, 4H), 7.68-7.75 (m, 8H), 9.24 (br s, 4H). $^{13}$C NMR (DMSO-d$_6$): δ 163.40, 157.15, 138.22, 137.49, 135.21, 126.72, 126.57, 123.95, 59.58, 42.40, 22.54, 14.53. MS (ESI) m/e (rel. int.): 573 (M$^+$, 17), 287 (100). Anal. Calc. for $C_{32}H_{40}N_6O_4$: C %, 67.11; H %, 7.03; N %, 14.67. Found C %, 66.95; H %, 7.16; N %, 14.37.

4,4"-Bis(N'-isopropyl)-guanidino-[1,1';4',1"]terphenyl (51b). The same procedure described for the preparation of 51a was used starting with 50c. Yield % 73; mp 246-247° C. $^1$H NMR (DMSO-d$_6$): δ 1.11 (d, J=6.3 Hz, 18H), 3.81-3.89 (m, 2H), 5.38 (br s, 6H), 6.87 (d, J=8.4 Hz, 4H), 7.53 (d, J=8.4 Hz, 4H), 7.74 (s, 4H). $^{13}$C NMR (DMSO-d$_6$): δ 150.95, 149.36, 138.23, 131.47, 126.69, 126.14, 123.36, 41.56, 22.84. MS (ESI) m/e (rel. int.): 429 (M$^+$, 8), 215 (100).

51b Hydrochloride salt. mp 275-277° C. $^1$H NMR (DMSO-d$_6$): δ 1.19 (d, J=6.6 Hz, 12H), 3.85-3.96 (m, 2H), 5.38 (br s, 6H), 7.31 (d, J=8.4 Hz, 4H), 7.77-7.80 (m, 8H), 8.13 (br s, 2H), 9.91 (br s, 2H). Anal. Calc. for $C_{26}H_{32}N_6$-2.0HCl-1.5H$_2$O-0.25C$_2$H$_5$OH: C %, 58.93; H %, 7.18; N %, 15.56. Found C %, 59.00; H %, 6.82; N %, 15.33.

Example 14

1,4-Bis-(5'-aminopyridin-2'-yl)phenylene (53). To a solution of 52 (10 mmol) in EtOH/EtOAc (200 mL, 1:1) was added 10% palladium on carbon (1.2 g). The mixture was placed on Parr hydrogenation apparatus at 50 psi for 8 h at room temperature. The mixture was filtered through hyflo and the filter pad. The filtrate was evaporated under reduced pressure and the precipitate was collected and washed with ether to give 53 in 77% yield, mp >250-251° C. $^1$H NMR (DMSO-d$_6$): δ 5.46 (br s, 4H), 6.98 (dd, J=8.4, 2.4 Hz, 2H), 7.65 (d, J=8.4 Hz, 2H), 7.93 (s, 4H), δ 8.02 (d, J=2.4 Hz, 2H). $^{13}$C NMR (DMSO-d$_6$): δ 144.0, 143.4, 137.8, 135.9, 125.0, 120.5, 120.0. MS (ESI) m/e (rel. int.): 263 (M$^+$+1, 100).

1,4-Bis-(5'-guanidinopyridin-2'-yl)phenylene hydrochloride salt (55). Adopting the same procedure used for the preparation of 48 starting with compound 54. Compound 54 was prepared by the same procedure described for 47, starting with compound 53.

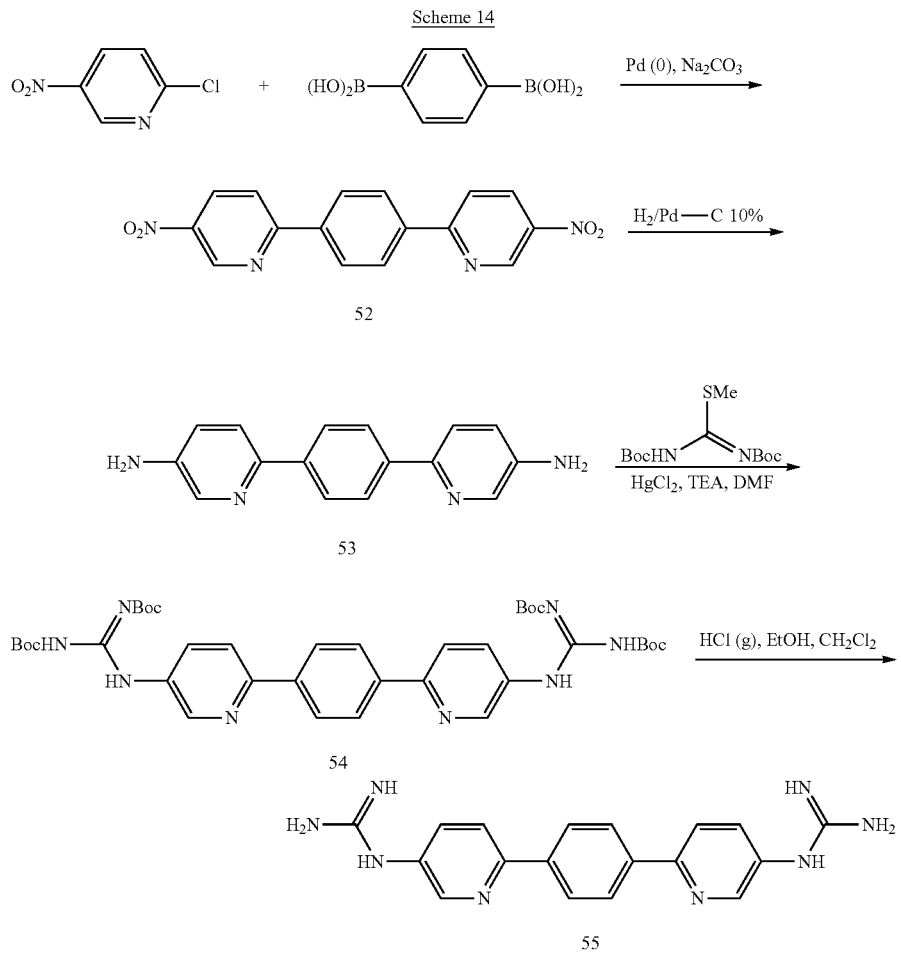

1,4-Bis-(5'-nitropyridin-2'-yl)phenylene (52). Adopting the same procedure used for the preparation of 17, a Suzuki coupling reaction was performed using 2-chloro-5-nitropyridine (20 mmol) and 1,4-phenylenebisboronic acid (10 mmol) to yield the target compound 52 in 90% yield, mp >300° C. $^1$H NMR (DMSO-d$_6$): δ 8.33-8.39 (m, 6H), 8.67 (dd, J=8.4, 2.1 Hz, 2H), 9.46 (d, J=2.1 Hz, 2H). MS (ESI) m/e (rel. int.): 323 (M$^+$+1, 100), 307 (80), 287 (15).

55 hydrochloride salt: mp 271-273° C. $^1$H NMR (D$_2$O/DMSO-d$_6$): δ 8.15-8.25 (m, 8H), 8.62 (s, 2H). $^{13}$C NMR (DMSO-d$_6$): δ 156.4, 152.3, 144.7, 137.7, 133.7, 131.7, 126.9, 121.2: MS (ESI) m/e (rel. int.): 347 (M$^+$+1, 20), 305 (40), 288 (5), 263 (10), 174 (100). Anal. Calc. for $C_{18}H_{18}N_8$-4.0HCl-1.1H$_2$O-1.0C$_2$H$_5$OH: C %, 43.04; H %, 5.40; N %, 20.07. Found C %, 43.03; H %, 5.00; N %, 19.78.

Example 15

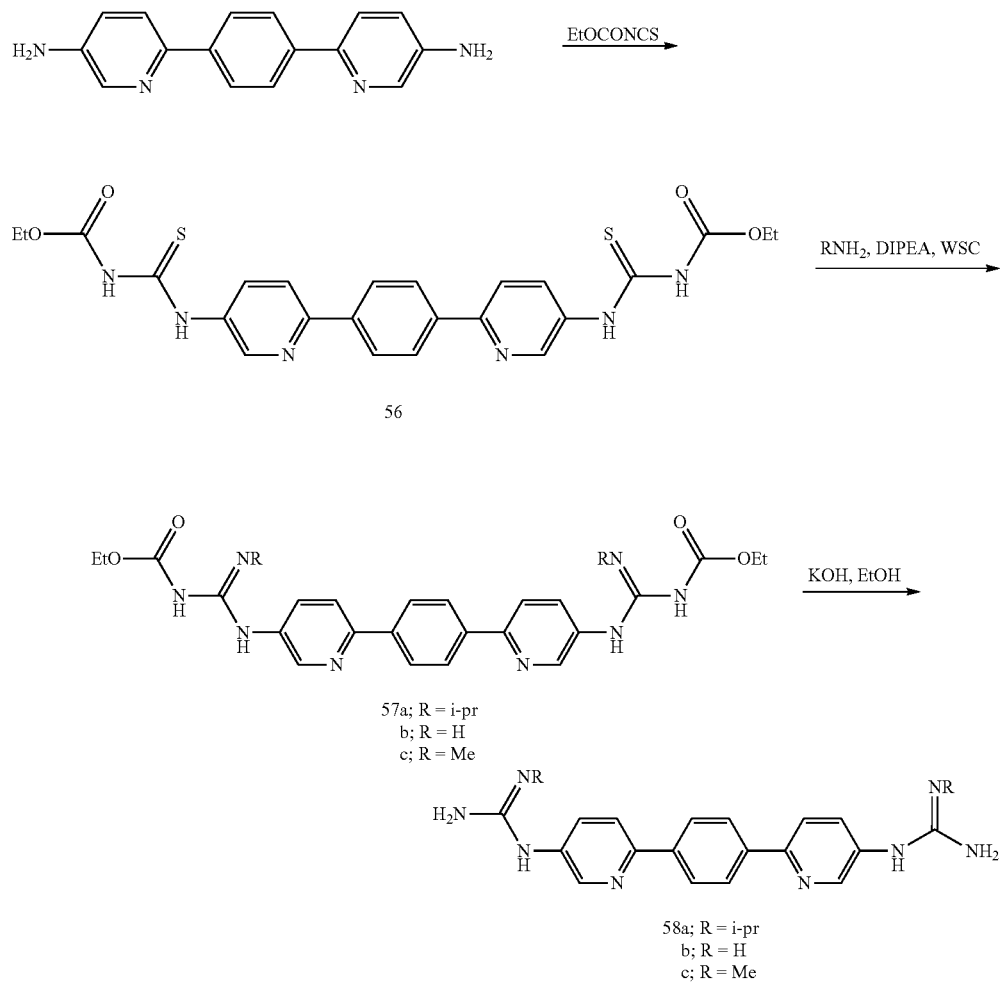

Scheme 15

1,4-Bis-[5'-(N'-ethoxycarbonylthiourido)-pyridin-2'-yl] phenylene (56). The same procedure described for the preparation of 49 was used starting with 53. Yield % 89; mp >300° C. $^1$H NMR (DMSO-$d_6$): δ 1.29 (t, J=6.9 Hz, 6H), 4.25 (q, J=6.9 Hz, 4H), 8.03 (d, J=8.7 Hz, 2H), 8.16-8.21 (m, 6H), 8.80 (s, 2H), 11.12 (br s, 2H), 11.51 (br s, 2H). $^{13}$C NMR (DMSO-$d_6$): δ 179.3, 153.0, 152.4, 145.4, 138.1, 133.9, 132.6, 126.4, 119.3, 61.7, 13.6. MS (ESI) m/e (rel. int.): 525 (M$^+$, 20), 409 (30), 241 (45), 163 (100).

1,4-Bis-{5'-[(N'-ethoxycarbonyl-N"-isopropyl)-guanidino]-pyridin-2'-yl}phenylene (57a). The same procedure described for the preparation of 50c was used starting with 56. Yield % 64; mp >300° C. $^1$H NMR (DMSO-$d_6$): δ 1.13 (t, J=7.2 Hz, 6H), 1.20 (d, J=6 Hz, 12H), 3.95 (q, J=7.2 Hz, 4H), 4.03-4.14 (m, 2H), 7.86 (s, 2H), 7.99 (d, J=8.7 Hz, 2H), 8.17 (s, 4H), 8.64 (s, 2H), 9.20 (br s, 4H). MS (ESI) m/e (rel. int.): 575 (M$^+$+1, 100), 529 (20), 503 (5). Anal. Calc. for $C_{30}H_{38}N_8O_4$-0.5$H_2O$: C %, 61.73; H %, 6.73; N %, 19.19. Found C %, 61.75; H %, 6.55; N %, 18.90.

1,4-Bis-{5'-[(N'-isopropyl)-guanidino]-pyridin-2'-yl}phenylene (58a). The same procedure used for the preparation of 51a was used starting with 57a. Yield % 59; mp 224-225° C. $^1$H NMR (DMSO-$d_6$): δ 1.16 (d, J=6.9 Hz, 12H), 3.86-3.98 (m, 2H), 6.30 (br s, 6H), 7.37 (dd, J=8.4, 2.1 Hz, 2H), 7.85 (d, J=8.4 Hz, 2H), 8.10 (s, 4H), 8.25 (d, J=2.1 Hz, 2H). $^{13}$C NMR (DMSO-$d_6$): δ 182.9, 152.3, 148.3, 144.7, 138.1, 130.5, 125.7, 119.7, 42.0, 22.4. MS (ESI) m/e (rel. int.) 431 (M$^+$+1, 100), 372 (5), 216 (65).

58a Hydrochloride salt. mp 278-280° C. Anal. Calc. for $C_{24}H_{30}N_8$-4.0HCl-0.75$H_2O$: C %, 48.90; H %, 6.06; N %, 18.99. Found C %, 49.15; H %, 6.09; N %, 18.62.

1,4-Bis-{[5'-(N'-ethoxycarbonyl)-guanidino]pyridin-2'-yl}phenylene (57b). The same procedure described for the preparation of 50a was used starting with 56.

1,4-Bis-[5'-(guanidino)-pyridin-2'-yl]phenylene (58b). The same procedure described for the preparation of 51a was used starting with 57b.

1,4-Bis-{5'-[(N'-ethoxycarbonyl-N"-methyl)-guanidino]-pyridin-2'-yl}phenylene (57c). The same procedure described for the preparation of 50b was used starting with 56.

1,4-Bis-{5'-[(N'-methyl)-guanidino]-pyridin-2'-yl}phenylene (58c). The same procedure described for the preparation of 51a was used starting with 57c.

Example 16

Compounds 61 and 64

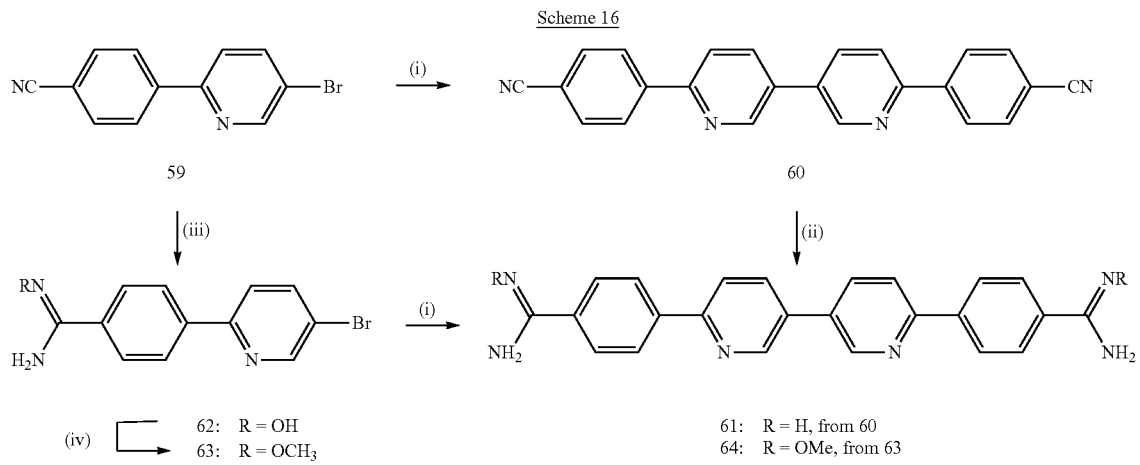

Scheme 16

Reagents and conditions: (i) Bis(tributyltin), Pd(PPh$_3$)$_4$, toluene, 120° C., 4 h; (ii) a) LiN(TMS)$_2$, THF, r.t., overnight; b) HCl (gas), dry ethanol, r.t., overnight; (iii) NH$_2$OH•HCl KO-t-Bu, DMSO; (iv) (CH$_3$O)$_2$SO$_2$, LiOH.

Compound 59. 2,5-Dibromopyridine and p-cyanophenyl-boronic acid were reacted under the above-mentioned Suzuki coupling conditions. Yield 70%, mp 174-175° C. $^1$H NMR (DMSO-d$_6$); δ 7.90-8.03 (m, 3H), 8.14-8.24 (m, 3H), 8.80 (s, 1H). $^{13}$C NMR; δ 152.6, 150.2, 141.4, 139.7, 132.4, 127.0, 122.5, 120.1, 118.3, 111.6. MS (m/z, rel. int.); 259 (M$^+$, 100), 179 (70), 152 (55).

Compound 60. Stille homocoupling starting with 59. Yield 77%, mp >300° C. $^1$H NMR (DMSO-d$_6$); δ 7.96 (d, J=8.1 Hz, 4H), 8.20-8.37 (m, 8H), 9.18 (s, 2H). $^{13}$C NMR; δ 153.4, 147.6, 142.0, 135.1, 132.3, 131.5, 126.9, 120.8, 118.2, 111.4. MS (m/z, rel. int.); 358 (M$^+$, 100), 330 (5), 256 (10), 179 (70).

Compound 61. Reduction of dinitrile 60 using LiN(TMS)$_2$. Reduction of the cyano groups of 59 using LiN(TMS)$_2$. Yield 81%, mp >300° C. $^1$H NMR (D$_2$O/DMSO-d$_6$); δ 8.00 (s, 4H), 8.23-8.43 (m, 8H), 9.15 (s, 2H). $^{13}$C NMR; δ 165.8, 154.3, 147.7, 142.9, 136.8, 132.3, 129.0, 128.6, 127.8, 122.3. MS (m/z, rel. int.); 393 (M$^+$+1, 95), 376 (8), 359 (5), 197 (100). Calcd for C$_{24}$H$_{20}$N$_6$-4.0HCl-2.5H$_2$O: C, 49.41; H, 4.99; N, 14.40. Found C, 49.18; H, 4.67; N, 14.22.

Compound 62. Direct conversion of the nitrile of 59 to an amidoxime using hydroxylamine in the presence of base. Yield 87%, mp 179-180° C. $^1$H NMR (DMSO-d$_6$); δ 5.87 (s, 2H), 7.75 (d, J=7.8 Hz, 2H), 7.92-8.09 (m, 4H), 8.73 (s, 1H), 9.73 (s, 1H). $^{13}$C NMR; δ 154.2, 150.4, 150.2, 139.7, 137.7, 134.1, 126.1, 125.7, 122.0, 119.2. MS (m/z, rel. int.); 291 (M$^+$, 90), 276 (100), 259 (50).

Compound 63. Methylation of the amidoxime of 62 using dimethyl sulfate. Yield 68%, mp 158-159° C. $^1$H NMR (DMSO-d$_6$); δ 3.76 (s, 3H), 6.13 (s, 2H), 7.76 (d, J=7.8 Hz, 2H), 7.96-8.14 (m, 4H), 8.76 (s, 1H). $^{13}$C NMR; δ 154.1, 150.5, 150.2, 139.8, 138.0, 133.3, 126.2, 126.1, 122.0, 119.3, 60.6. MS (m/z, rel. int.); 305 (M$^+$, 100), 290 (4), 274 (10), 259 (85).

Compound 64. Stille homocoupling of 63. Free base yield 73%, mp 232-233.5° C. $^1$H NMR (DMSO-d$_6$); δ 3.77 (s, 6H), 6.13 (s, 4H), 7.82 (d, J=8.4 Hz, 4H), 8.13-8.20 (m, 6H), 8.33 (dd, J=8.4, 2.4 Hz, 2H), 9.14 (d, J=2.4 Hz, 2H). $^{13}$C NMR; δ 154.7, 150.6, 147.6, 138.7, 135.1, 133.2, 131.1, 126.2, 126.1, 120.3, 60.66. MS (m/z, rel. int.); 452 (M$^+$, 100), 421 (5), 405 (50), 374 (40).

64 salt: mp 279-281° C. Calcd for C$_{26}$H$_{24}$N$_6$O$_2$-4.0HCl-4.25H$_2$O: C, 46.26; H, 5.40; N, 12.44. Found C, 46.09; H, 5.10; N, 12.11.

Example 17

Biological Results

In vitro antiprotozoal activities were measured following established protocols. See Ismail, M. A., et al., *J. Med. Chem.*, 46, 4761-4769 (2003); Stephens, C. E., et al., *Bioorg. Med. Chem. Lett.*, 13, 2065-2069 (2003) (in vitro assay against *Leishmania donovani*). The activities of the presently disclosed compounds against *Trypanosoma brucei rhodesiense* (T. b. r.), *Plasmodium falciparum* (P. f.), *Leishmania donovani* (L. d.), and L-6 rat mycoblast cells (as an assay for cell toxicity, CT) are shown in Tables 1 and 2 These values are compared to those of pentamidine and furamidine.

The activities of compounds 20, 18, 21, 48, 23c, 24c, 5, 4, and 10 against the STIB 900 strain of *Trypanosoma brucei rhodesiense* (T. b. r.) in a mouse model are shown in Table 3. These values are compared to those of pentamidine and furamidine. Groups of four mice were infected intraperitoneally with 2×10$^5$ bloodstream forms of T. b. r. STIB 900 which originates from a patient in Tanzania. On days 3, 4, 5, and 6 post-infection the experimental groups were treated with the indicated compound, either by the intraperitoneal route, or for prodrugs, by the oral route. Usually the highest tolerated dose was used. The highest tolerated dose was determined in a pretoxicological experiment.

Parasitemia of the mice was checked daily up to day 14 post-infection and thereafter 2 times per week up to day 60. One group of mice was not treated and acted as control. Untreated control animals expire between day 7 and 8 post-infection. For relapsing mice, the day of death was recorded and the survival time determined. For the data shown in Table 3, cures reflect the number of mice that survive and are parasite free for 60 days. Survival reflects the average days of survival.

TABLE 1

Linear Triaryl Dications.

*Structure: A—M(pyridine ring)—[ring with R1, X, Y, Z, R, R2]*

| Code | A | R | R1 | R2 | M | X | Y | Z | ΔT$_m$ | T.b.r. IC$_{50}$ (nM) | P.f. IC$_{50}$ (nM) | L.d. IC$_{50}$ (μM) | CT IC$_{50}$ (μM) |
|---|---|---|---|---|---|---|---|---|---|---|---|---|---|
| pentamidine | NA | NA | NA | NA | NA | NA | NA | NA | 12.6 | 2.2 | nt | 2.2 | 11.4 |
| furamidine | NA | NA | NA | NA | NA | NA | NA | NA | 25 | 4.5 | 15.5 | | 6.4 |
| 20 | C(NH)(NH$_2$)CH$_3$ | -C$_6$H$_4$-A (para) | H | nil | CH | CH | CH | CH | 19.1 | 5 | 1 | | 22.1 |
| 18 | C(NOH)(NH$_2$)CH$_3$ | -C$_6$H$_4$-A (para) | H | nil | CH | CH | CH | CH | | 22.8k | >118k | | >212 |
| 21 | C(NOMe)(NH$_2$)CH$_3$ | -C$_6$H$_4$-A (para) | H | nil | CH | CH | CH | CH | | 13.8k | 371 | | 118 |
| 23a | C(NH)(NH$_2$)CH$_3$ | -C$_6$H$_4$-A (para) | F | nil | CH | CH | CH | CH | 15.1 | 2 | 1 | 0.34 | 6.4 |
| 24a | C(NOH)(NH$_2$)CH$_3$ | -C$_6$H$_4$-A (para) | F | nil | CH | CH | CH | CH | | >201k | 925 | | 29.1 |
| 25a | C(NOMe)(NH$_2$)CH$_3$ | -C$_6$H$_4$-A (para) | F | nil | CH | CH | CH | CH | | >51.5k | 4.2k | | |
| 23b | C(NH)(NH$_2$)CH$_3$ | -C$_6$H$_4$-A (para) | CF$_3$ | nil | CH | CH | CH | CH | 10.1 | 48 | 15 | 3.0 | 9.0 |
| 24b | C(NOH)(NH$_2$)CH$_3$ | -C$_6$H$_4$-A (para) | CF$_3$ | nil | CH | CH | CH | CH | | 29.9k | 3.1k | | 13.3 |
| 25b | C(NOMe)(NH$_2$)CH$_3$ | -C$_6$H$_4$-A (para) | CF$_3$ | nil | CH | CH | CH | CH | | 36.9k | 3.8k | | 42.2 |
| 65 | C(NH)(NH$_2$)CH$_3$ | -C$_6$H$_4$-A (para) | OMe | OMe | CH | CH | CH | CH | | | | | |
| 48 | HN-C(NH)(NH$_2$)-NHMe (guanidine) | -C$_6$H$_4$-A (para) | H | nil | CH | CH | CH | CH | 12.2 | 18 | 27 | 1.2 | 25.4 |

TABLE 1-continued

Linear Triaryl Dications.

| Code | A | R | R₁ | R₂ | M | X | Y | Z | ΔT$_m$ | T. b. r. IC$_{50}$ (nM) | P. f. IC$_{50}$ (nM) | L. d. IC$_{50}$ (μM) | CT IC$_{50}$ (μM) |
|---|---|---|---|---|---|---|---|---|---|---|---|---|---|
| 50a | guanidine-NHC(=O)OEt | 4-phenyl-A | H | nil | CH | CH | CH | CH | | 142k | 1.7k | | >181 |
| 51a | N-methylguanidine (NMe) | 4-phenyl-A | H | nil | CH | CH | CH | CH | | 18 | 7 | | 65.1 |
| 50b | N-methyl-NHC(=O)OEt guanidine | 4-phenyl-A | H | nil | CH | CH | CH | CH | | 7.5K | 8.9K | | 5.7 |
| 51b | N-isopropyl guanidine | 4-phenyl-A | H | nil | CH | CH | CH | CH | | 530 | 14 | 7.2 | 21.9 |
| 50c | N-isopropyl-NHC(=O)OEt guanidine | 4-phenyl-A | H | nil | CH | CH | CH | CH | | 14.2K | 4.5K | | 5.3 |
| 55 | guanidine | 6-pyridyl-A | H | nil | N | CH | CH | CH | | 169 | 151 | | 152 |
| 57b | NHC(=O)OEt guanidine | 6-pyridyl-A | H | nil | N | CH | CH | CH | | | | | |
| 58c | N-methyl guanidine | 6-pyridyl-A | H | nil | N | CH | CH | CH | | | | | |
| 57c | N-methyl-NHC(=O)OEt guanidine | 6-pyridyl-A | H | nil | N | CH | CH | CH | | | | | |
| 58a | N-isopropyl guanidine | 6-pyridyl-A | H | nil | N | CH | CH | CH | | | | | |

TABLE 1-continued

Linear Triaryl Dications.

| Code | A | R | $R_1$ | $R_2$ | M | X | Y | Z | $\Delta T_m$ | T. b. r. $IC_{50}$ (nM) | P. f. $IC_{50}$ (nM) | L. d. $IC_{50}$ (μM) | CT $IC_{50}$ (μM) |
|---|---|---|---|---|---|---|---|---|---|---|---|---|---|
| 57a | N-isopropyl-N'-ethoxycarbonyl guanidine (—NH—C(=N-iPr)—NHC(=O)OEt) | 2-pyridyl (6-A) | H | nil | N | CH | CH | CH | | | | | |
| 23c | amidine (C(=NH)NH$_2$) | 4-phenyl | H | nil | CH | CH | N | CH | 18.7 | 2 | 10 | | 49.9 |
| 24c | C(=NOH)NH$_2$ | 4-phenyl | H | nil | CH | CH | N | CH | | 9.3K | 7.6K | | >184 |
| 25c | C(=NOMe)NH$_2$ | 4-phenyl | H | nil | CH | CH | N | CH | | 34.7K | 3.2K | | >166 |
| 36b | C(=NH)NH$_2$ | 4-(CH$_2$)phenyl | H | nil | CH | CH | CH | CH | | | | | |
| 36a | C(=NH)NH$_2$ | 4-(CH$_2$)phenyl | H | nil | CH | CH | N | CH | | 41 | 11 | | 18.1 |
| 66 | C(=NH)NH$_2$ | 4-phenyl | H | nil | CH | N | N | CH | 16.1 | 14 | 1 | 0.72 | 31.3 |
| 67 | C(=NOH)NH$_2$ | 4-phenyl | H | nil | CH | N | N | CH | | 12K | 2.4K | | 8.1 |
| 68 | C(=NOMe)NH$_2$ | 4-phenyl | H | nil | CH | N | N | CH | | 141K | 5.5K | | >194 |
| 31 | C(=NH)NH$_2$ | 2-pyridyl (6-A) | H | nil | N | CH | CH | CH | | 47 | 10 | >100 | 25.6 |
| 33 | C(=NOMe)NH$_2$ | 2-pyridyl (6-A) | H | nil | N | CH | CH | CH | | 82.9K | 1.2K | | >158 |

TABLE 1-continued

Linear Triaryl Dications.

| Code | A | R | R₁ | R₂ | M | X | Y | Z | $\Delta T_m$ | T. b. r. IC$_{50}$ (nM) | P. f. IC$_{50}$ (nM) | L. d. IC$_{50}$ (µM) | CT IC$_{50}$ (µM) |
|---|---|---|---|---|---|---|---|---|---|---|---|---|---|
| 27 | NH, NH₂ (acetamidine) | phenyl-A | H | nil | CH | CH | N | N | | 16 | 0.5 | | 40.9 |
| 29 | NOMe, NH₂ | phenyl-A | H | nil | CH | CH | N | N | | | | | |
| 5 | NH, NH₂ | furan-A | H | nil | CH | CH | CH | CH | | 5 | 1 | | 2.0 |
| 3 | NOH, NH₂ | furan-A | H | nil | CH | CH | CH | CH | | 67K | 6.6K | | 106. |
| 4 | NOMe, NH₂ | furan-A | H | nil | CH | CH | CH | CH | | 24K | 1.6K | | >206 |
| 10 | NH, NH₂ | furan-A | H | nil | CH | N | CH | CH | | 2 | 5.2 | 20.5 | 30.9 |

TABLE 2

Linear Triaryl Dications In Vitro Results.

A—⌬—L—⌬—A

| Code | A | L | $\Delta T_m$ | T. b. r. IC$_{50}$ (nM) | P. f. IC$_{50}$ (nM) | L. d. IC$_{50}$ (µM) | cytotoxicity (CT) IC$_{50}$ (µM) |
|---|---|---|---|---|---|---|---|
| 38a | NH, NH₂ | naphthyl | | 175 | 21 | 12.9 | 7.3 |
| 39 | NOH, NH₂ | naphthyl | | 13.4K | 9.1K | | 9.4 |

TABLE 2-continued

Linear Triaryl Dications In Vitro Results.

A—⟨phenyl⟩—L—⟨phenyl⟩—A

| Code | A | L | $\Delta T_m$ | T. b. r. IC$_{50}$ (nM) | P. f. IC$_{50}$ (nM) | L. d. IC$_{50}$ (μM) | cytotoxicity (CT) IC$_{50}$ (μM) |
|---|---|---|---|---|---|---|---|
| 40 | NOMe, NH$_2$ (acetamidoxime methyl ether) | 1,5-naphthalene | | 29.5K | 3.9K | | 16.2 |
| 38b | NH, NH$_2$ (amidine) | 2,6-naphthalene | 18.2 | 53 | 19 | 0.28 | 8 |
| 61 | NH, NH$_2$ (amidine) | 6,6'-bipyridine | 16.7 | 8 | 5 | | 40.9 |

TABLE 3

Linear Triaryl Dications In Vivo Results versus T. b. r.

| Code | Dosage (mg/kg) | Route | Cures | Survival (days) |
|---|---|---|---|---|
| pentamidine | 20 | ip | 0/4 | 42.7 |
| furamidine | 20 | ip | 2/4 | >47.7 |
| 20 | 20 | ip | 0/4 | 52.5 |
| 18 | 100 | po | 0/4 | 24.75 |
| 21 | 100 | po | 0/4 | 20.75 |
| 48 | 20 | ip | 0/4 | >60 |
| 23c | 20 | ip | 4/4 | >60 |
| 24c | 100 | po | 1/4 | >35.75 |
| 5 | 20 | ip | 0/4 | 21.25 |
| 4 | 100 | po | 0/4 | 29 |
| 10 | 20 | ip | 3/4 | >53.5 |

Example 18

Compounds 66, 67, 68, and 69

Scheme 17

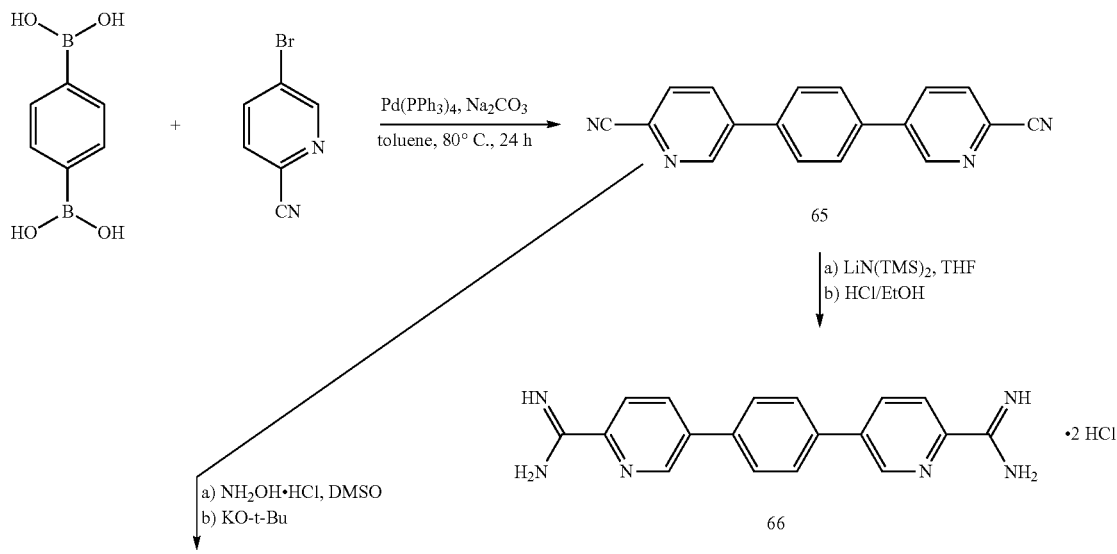

-continued

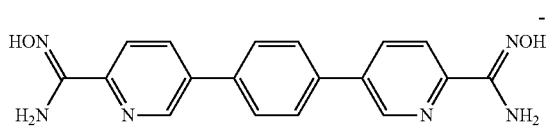

67

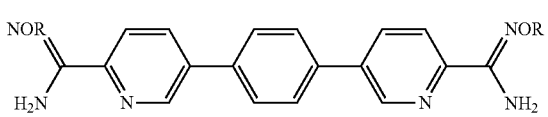

69

R = C(═O)CH$_2$N(CH$_3$)$_2$

LiOH·H$_2$O
(CH$_3$O)$_2$SO$_2$

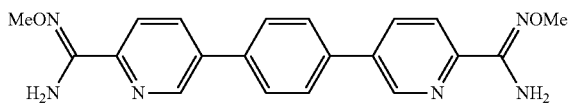

68

1,4-Bis-(2'-cyanopyridin-5'-yl)phenylene (65). To a stirred solution of 5-bromo-2-pyridinecarbonitrile (6.60 g, 36.0 mmol), and tetrakis(triphenylphosphine) palladium (1.80 g, 1.56 mmol) in toluene (100 mL) under a nitrogen atmosphere was added 50 mL of a 2 M aqueous solution of Na$_2$CO$_3$ followed by 1,4-phenylenebisboronic acid (3.90 g, 24.0 mmol) in 50 mL of methanol. The vigorously stirred mixture was warmed to 80° C. overnight. After cooling, the solution was filtered, and the precipitate was washed with toluene, water, and ether to afford 65 as a white solid (4.70 g, 92% yield); mp >300° C. $^1$H NMR (DMSO-d$_6$): δ 7.99 (s, 4H), 8.08 (d, J=8.0 Hz, 2H), 8.38 (dd, J=2.0, 8.0 Hz, 2H), 9.14 (d, J=2.0 Hz, 2H).

1,4-Bis-(2'-amidinopyridin-5'-yl)-phenylene hydrochloride salt (66). Dinitrile 65 (570 mg, 2.0 mmol), suspended in freshly distilled THF (30 mL), was treated with lithium trimethylsilylamide (1 M solution in THF, 15 mL, 15.0 mmol), and was allowed to stir overnight. The reaction mixture was then cooled to 0° C. and HCl saturated ethanol (15 mL) was added, whereupon a precipitate formed. The mixture was allowed to stand overnight, after which it was diluted with ether, and the resultant solid was collected by filtration. The diamidine was purified by neutralization with 1 N NaOH followed by filtration of the resultant solid and washing with water (3×). Finally, the free base was stirred with ethanolic HCl overnight and diluted with ether, and the solid formed was filtered and dried to give 66 as a hydrochloride salt in 68% yield; mp >300° C. $^1$H NMR (D$_2$O/DMSO-d$_6$): δ 8.11 (s, 4H), 8.47 (d, J=8.4 Hz, 2H), 8.60 (dd, J=2.0, 8.4 Hz, 2H), 9.24 (d, J=2.0 Hz, 2H), 9.41 (s, 4H), 9.66 (s, 4H). Anal. Calc. for C$_{18}$H$_{16}$N$_6$-2.0HCl-0.3H$_2$O: C, 54.78; H, 4.75; N, 21.29. Found: C, 55.03; H, 4.60; N, 21.01.

1,4-Bis-[2'-(N-hydroxyamidinopyridin-5'-yl)]-phenylene hydrochloride salt (67). A mixture of hydroxylamine hydrochloride (6.03 g, 86.8 mmol) in anhydrous DMSO (100 mL) was cooled to 5° C., and then potassium t-butoxide (9.73 g, 86.8 mmol) was added portion wise. To the mixture was added the above dinitrile 65 (2.45 mg, 8.68 mmol), and the mixture was stirred overnight at room temperature. The reaction mixture was poured onto ice/water, whereupon a white precipitate of the diamidoxime formed. The product was collected by filtration and washed with water to afford the free base of 67 in 96% yield. Finally, the free base was stirred with ethanolic HCl overnight and diluted with ether, and the solid formed was filtered and dried to give the hydrochloride salt; mp 231-233° C. $^1$H NMR (DMSO-d$_6$): δ 8.00 (s, 4H), 8.09 (d, J=8.4 Hz, 2H), 8.39 (dd, J=2.0, 8.4 Hz, 2H), 9.15 (d, J=2.0 Hz, 2H). Anal. Calc. for C$_{18}$H$_{16}$N$_6$O$_2$-2.0HCl-1.5H$_2$O: C, 48.23; H, 4.72; N, 18.74. Found: C, 48.57; H, 4.71; N, 18:34.

1,4-Bis-[2'-(N-methoxyamidinopyridin-5'-yl)]-phenylene hydrochloride salt (68). To a suspension of the free base of 67 (560 mg, 1.6 mmol) in DMF (20 mL) was added LiOH.H$_2$O (270 mg, 6.4 mmol, in 3 mL of H$_2$O), which was followed by dimethyl sulfate (0.40 mL, 4.0 mmol). The reaction mixture was stirred overnight, after which it was poured onto ice/water, and the precipitate was filtered, washed with water, and dried to give the free base of 68 in 86% yield. Finally, the free base was stirred with ethanolic HCl overnight and diluted with ether, and the solid formed was filtered and dried to give hydrochloride salt; mp 232-234° C. $^1$H NMR (DMSO-d$_6$): δ 3.82 (s, 6H), 6.17 (s, 4H), 7.90 (s, 4H), 7.94 (d, J=8.4 Hz, 2H), 8.20 (dd, J=2.0, 8.4 Hz, 2H), 8.97 (d, J=2.0 Hz, 2H). Anal. Calc. for C$_{20}$H$_{20}$N$_6$O$_2$-2.0HCl-2.0H$_2$O: C, 49.79; H, 5.40; N, 17.31. Found: C, 49.47; H, 5.35; N, 17.03.

1,4-Bis-{2'-[N-(N',N'-dimethylaminoacetoxy)amidinopyridin-5'-yl]}-phenylene (69). A solution of the free base of 67 (350 mg, 1.0 mmol) in 30 mL DMF at room temperature was added with dimethylaminoacetyl chloride hydrochloride (720 mg, 4.0 mmol) and triethylamine (1.40 mL, 8.0 mmol), stirred overnight, and filtered. The precipitate was washed with water, and dried to give 69 in 55% yield, mp 213-215° C. $^1$H NMR (DMSO-d$_6$): δ 2.31 (s, 12H), 3.38 (s, 4H), 6.97 (s, 4H), 7.98 (s, 4H), 8.04 (d, J=8.4 Hz, 2H), 8.30 (dd, J=2.0, 8.1 Hz), 9.05 (s, 2H). $^{13}$C NMR (DMSO-d$_6$): δ 167.8, 154.2, 147.3, 146.7, 136.4, 135.1, 127.8, 123.4, 121.1, 58.2, 44.6. Anal. Calc. for C$_{26}$H$_{30}$N$_8$O$_4$-1.4H$_2$O: C, 57.43; H, 6.08; N, 20.61. Found: C, 57.63; H, 5.94; N, 20.64.

Example 19

Compounds 71 and 73

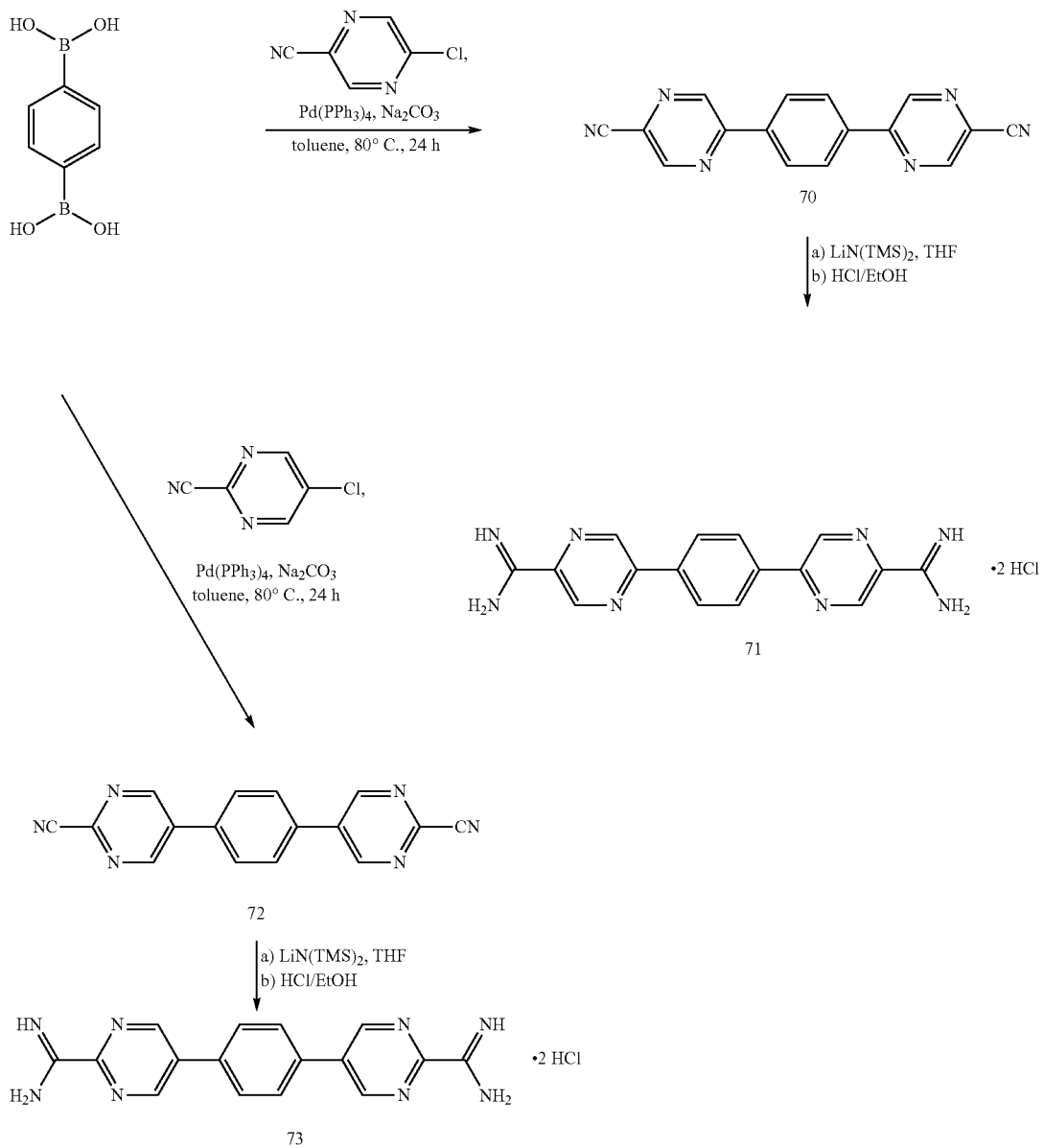

1,4-Bis-(2'-cyanopyrazin-5'-yl)phenylene (70). The same procedure described for 1,4-Bis-(2'-cyanopyridin-5'-yl)phenylene was used by employing 5-chloro-2-pyrazinecarbonitrile and 1,4-phenylenebisboronic acid to furnish 70 in 74% yield; mp >300° C. (DMF). $^1$H NMR (DMSO-d$_6$): δ 8.39 (s, 4H), 9.22 (s, 2H), 9.69 (s, 2H).

1,4-Bis-(2'-amidinopyrazin-5'-yl)-phenylene hydrochloride salt (71). The same procedure described for the preparation of 66 was used starting with the above dinitrile, 70; 55% yield; mp >300° C. $^1$H NMR (DMSO-d$_6$): δ 8.64 (s, 4H), 9.47 (s, 2H), 9.71 (s, 4H), 9.78 (s, 2H), 9.92 (s, 4H). Anal. Calc. for $C_{16}H_{14}N_8$·2.0HCl·0.65H$_2$O: C, 47.69; H, 4.33; N, 27.81. Found: C, 48.04; H, 4.18; N, 27.52.

1,4-Bis-(2'-cyanopyrimidin-5'-yl)-phenylene (72). The same procedure described for 1,4-Bis-(2'-cyanopyridin-5'-yl)phenylene was used by employing 5-bromo-2-pyrimidinecarbonitrile and 1,4-phenylenebisboronic acid to furnish 72 in 69% yield; mp >300° C. (DMF). $^1$H NMR (DMSO-d$_6$): δ 8.16 (s, 4H), 9.50 (s, 4H).

1,4-Bis-(2'-amidinopyrimidin-5'yl)-phenylene hydrochloride salt (73). The same procedure described for the preparation of 66 was used starting with the above dinitrile, 72; 68% yield; mp >300° C. $^1$H NMR (DMSO-d$_6$): δ 8.24 (s, 4H), 9.57 (s, 4H), 9.60 (s, 4H), 9.76 (s, 4H). Anal. Calc. for $C_{16}H_{14}N_8$·2.0HCl·2.5H$_2$O: C, 44.05; H, 4.83; N, 25.68. Found: C, 44.39; H, 4.55; N, 25.28.

Example 20

Compound 75

Scheme 19

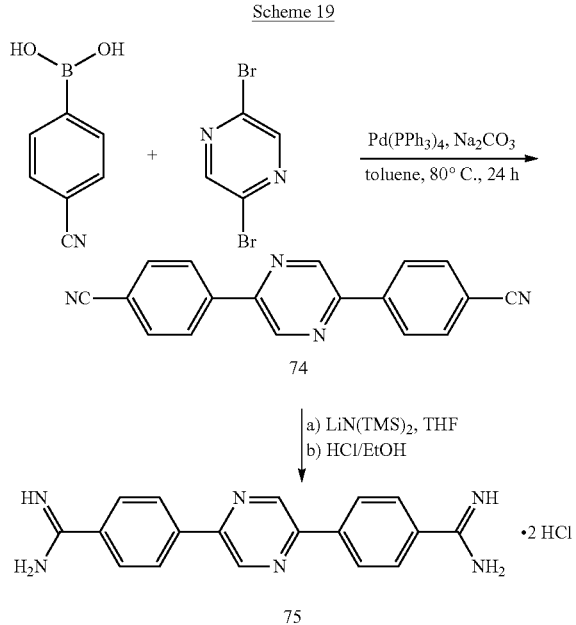

2,5-Bis-(4'-cyanophenyl)-pyrazine (74). The same procedure described for 1,4-Bis-(2'-cyanopyridin-5'-yl)phenylene was used by employing 2,5-dibromopyrazine and 4-cyanophenylboronic acid to furnish 74 in 52% yield; mp >300° C. (DMF). $^1$H NMR (DMSO-d$_6$): δ 7.99 (d, J=8.4 Hz, 4H), 8.39 (d, J=8.4 Hz, 4H), 9.42 (s, 2H).

2,5-Bis-(4'-amidinophenyl)-pyrazine hydrochloride salt (75). The same procedure described for the preparation of 66 was used starting with the above dinitrile, 74; 76% yield; mp >300° C. $^1$H NMR (DMSO-d$_6$): δ 8.05 (d, J=8.4 Hz, 4H), 8.45 (d, J=8.4 Hz, 4H), 9.37 (s, 4H), 9.53 (s, 2H), 9.58 (s, 4H). $^{13}$C NMR (DMSO-d$_6$): δ 165.1, 149.0, 142.1, 140.2, 129.2, 129.0, 127.0. Anal. Calc. for C$_{18}$H$_{16}$N$_6$-2.0HCl-0.55H$_2$O: C, 54.16; H, 4.82; N, 21.05. Found: C, 54.41; H, 4.75; N, 20.71.

Example 21

Compound 77

Scheme 20

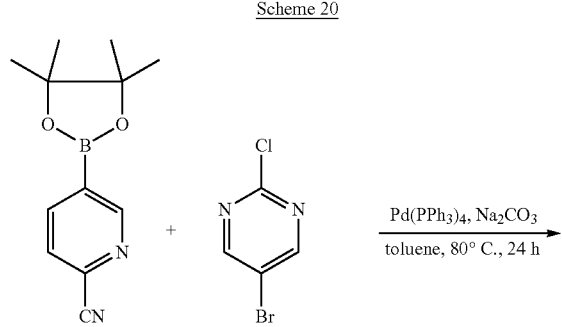

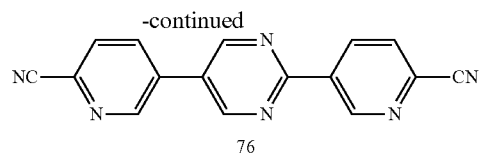

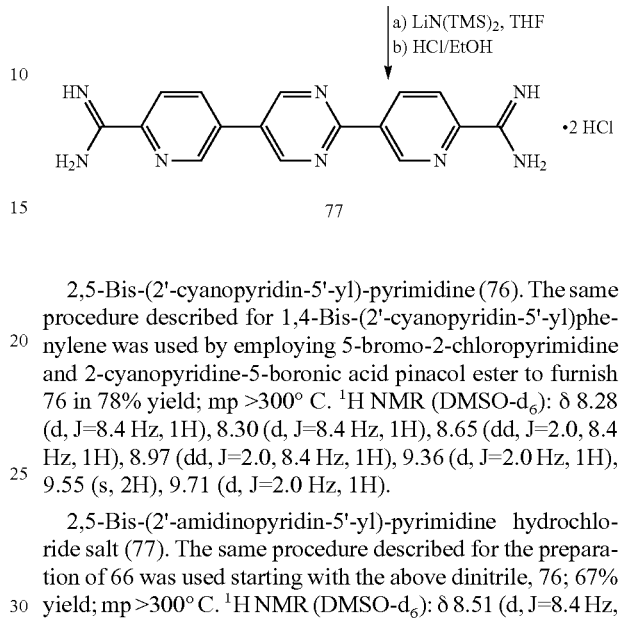

2,5-Bis-(2'-cyanopyridin-5'-yl)-pyrimidine (76). The same procedure described for 1,4-Bis-(2'-cyanopyridin-5'-yl)phenylene was used by employing 5-bromo-2-chloropyrimidine and 2-cyanopyridine-5-boronic acid pinacol ester to furnish 76 in 78% yield; mp >300° C. $^1$H NMR (DMSO-d$_6$): δ 8.28 (d, J=8.4 Hz, 1H), 8.30 (d, J=8.4 Hz, 1H), 8.65 (dd, J=2.0, 8.4 Hz, 1H), 8.97 (dd, J=2.0, 8.4 Hz, 1H), 9.36 (d, J=2.0 Hz, 1H), 9.55 (s, 2H), 9.71 (d, J=2.0 Hz, 1H).

2,5-Bis-(2'-amidinopyridin-5'-yl)-pyrimidine hydrochloride salt (77). The same procedure described for the preparation of 66 was used starting with the above dinitrile, 76; 67% yield; mp >300° C. $^1$H NMR (DMSO-d$_6$): δ 8.51 (d, J=8.4 Hz, 1H), 8.53 (d, J=8.4 Hz, 1H), 8.77 (dd, J=2.0, 8.4 Hz, 1H), 9.08 (dd, J=2.0, 8.4 Hz, 1H), 9.40 (d, J=2.0 Hz, 1H), 9.47 (s, 4H), 9.60 (s, 2H), 9.72 (d, J=2.0 Hz, 1H), 9.75 (s, 2H), 9.44 (s, 2H), 9.76 (d, J=2.0 Hz, 1H). Anal. Calc. for C$_{16}$H$_{14}$N$_8$-2.0HCl-0.8H$_2$O: C, 47.37; H, 4.37; N, 27.62. Found: C, 47.47; H, 4.14; N, 27.32.

Example 22

Compound 80

Scheme 21

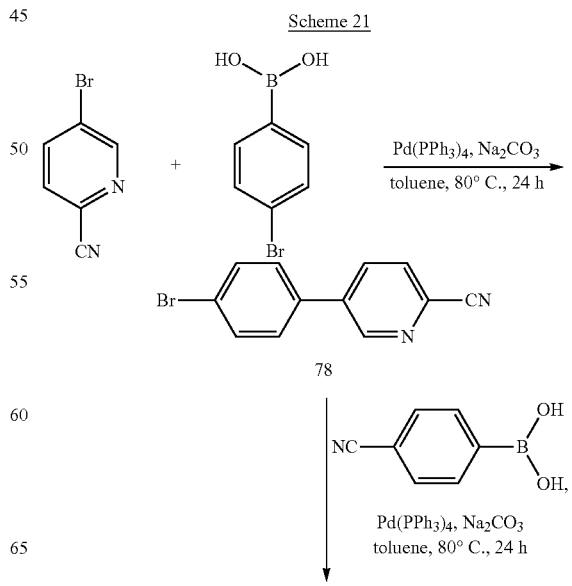

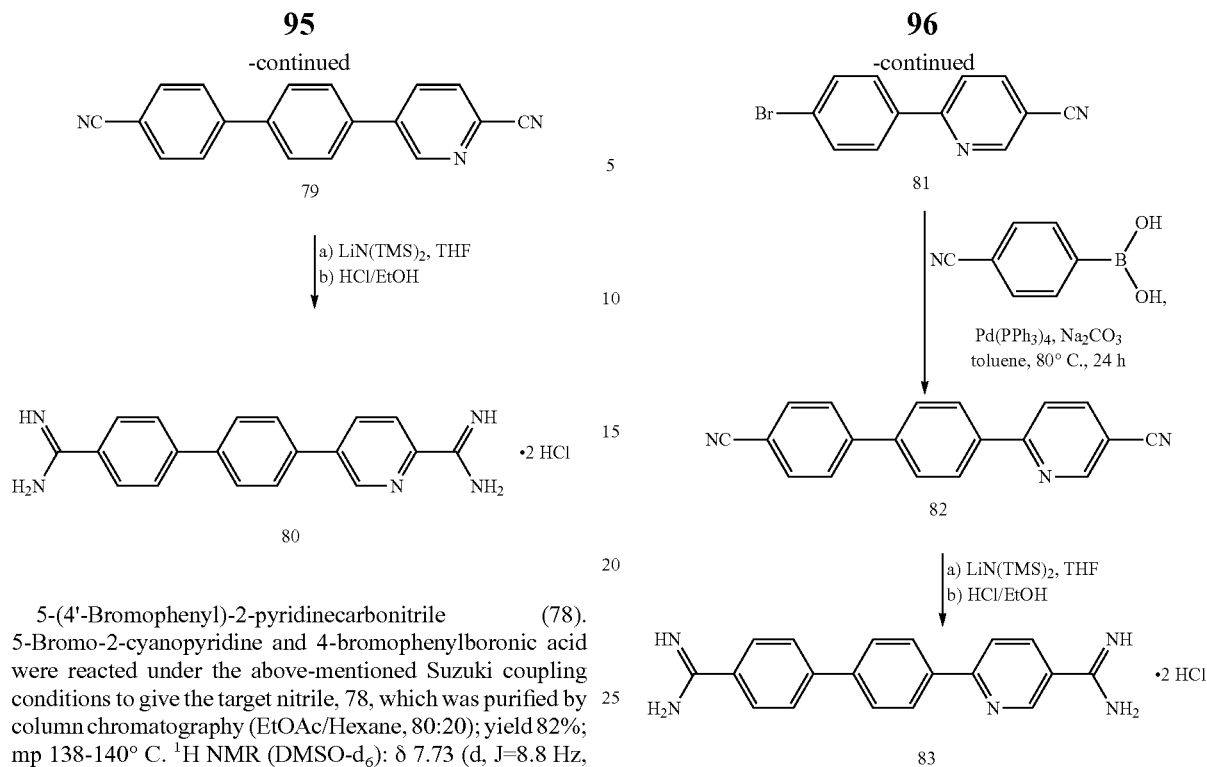

5-(4'-Bromophenyl)-2-pyridinecarbonitrile (78). 5-Bromo-2-cyanopyridine and 4-bromophenylboronic acid were reacted under the above-mentioned Suzuki coupling conditions to give the target nitrile, 78, which was purified by column chromatography (EtOAc/Hexane, 80:20); yield 82%; mp 138-140° C. $^1$H NMR (DMSO-$d_6$): δ 7.73 (d, J=8.8 Hz, 2H), 7.88 (d, J=8.8 Hz, 2H), 8.10 (d, J=8.0 Hz, 1H), 8.34 (dd, J=2.4, 8.0 Hz, 1H), 9.08 (d, J=2.4 Hz, 1H).

Phenyl[1,1']phenyl[4',5"]pyridinyl-4,2"-bis-carbonitrile (79). The above nitrile, 78, and 4-cyanophenylboronic acid were reacted under the above-mentioned Suzuki coupling conditions to give the target dinitrile; yield 84%; mp >300° C. $^1$H NMR (DMSO-$d_6$): δ 7.90-7.97 (m, 8H), 8.08 (d, J=8.4 Hz, 1H). 8.38 (dd, J=2.0, 8.4 Hz, 1H), 9.13 (d, J=2.0 Hz, 1H).

Phenyl[1,1']phenyl[4',5"]pyridinyl-4,2"-bis-amidine hydrochloride salt (80). The same procedure described for the preparation of 66 was used starting with the above dinitrile, 79; 65% yield; mp >300° C. $^1$H NMR (DMSO-$d_6$): δ 7.97 (d, J=8.4 Hz, 2H), 7.99 (d, J=8.4 Hz, 2H), 8.04 (d, J=8.4 Hz, 2H), 8.06 (d, J=8.4 Hz, 2H), 8.44 (d, J=8.4 Hz, 1H), 8.58 (dd, J=2.0, 8.4 Hz, 1H), 9.16 (s, 2H), 9.22 (d, J=2.0 Hz, 1H), 9.40 (s, 2H), 9.44 (s, 2H), 9.64 (s, 2H). Anal. Calc. for $C_{19}H_{17}N_5$-2.0HCl-0.6H$_2$O: C, 57.18; H, 5.10; N, 17.55. Found: C, 57.46; H, 5.08; N, 17.25.

Example 23

Compound 83

Scheme 22

2-(4'-Bromophenyl)-5-pyridinecarbonitrile (81). The same procedure described for 5-(4'-bromophenyl)-2-pyridinecarbonitrile was used by employing 2-bromo-5-cyanopyridine and 4-bromophenylboronic acid to furnish 81 in 78% yield; mp 157-159° C. $^1$H NMR (DMSO-$d_6$): δ 7.74 (d, J=8.8 Hz, 2H), 8.12 (d, J=8.8 Hz, 2H), 8.22 (d, J=8.4 Hz, 1H), 8.40 (dd, J=2.4, 8.4 Hz, 1H), 9.09 (d, J=2.4 Hz, 1H).

Phenyl[1,1']phenyl[4',2"]pyridinyl-4,5"-bis-carbonitrile (82). The above nitrile, 81, and 4-cyanophenylboronic acid were reacted under the above-mentioned Suzuki coupling conditions to give the target dinitrile, 82; yield 94%; mp >300° C. $^1$H NMR (DMSO-$d_6$): δ 7.68 (d, J=8.8 Hz, 2H), 7.73 (d, J=8.8 Hz, 2H), 7.86 (d, J=8.4 Hz, 2H), 7.96 (d, J=8.4 Hz, 2H), 8.14 (d, J=8.0 Hz, 1H), 8.42 (dd, J=2.0, 8.0 Hz, 1H), 9.17 (d, J=2.0 Hz, 1H).

Phenyl[1,1']phenyl[4',2"]pyridinyl-4,5"-bis-amidine hydrochloride salt (83). The same procedure described for the preparation of 66 was used starting with the above dinitrile, 82; 75% yield; mp >300° C. $^1$H NMR (DMSO-$d_6$): δ 7.98 (d, J=8.4 Hz, 4H), 8.04 (d, J=8.4 Hz, 2H), 8.06 (d, J=8.4 Hz, 2H), 8.33-8.37 (m, 4H), 9.11 (s, 1H), 9.26 (s, 2H), 9.38 (s, 2H), 9.49 (s, 2H), 9.66 (s, 2H). Anal. Calc. for $C_{19}H_{17}N_5$-2.0HCl-0.9H$_2$O: C, 56.42; H, 5.18; N, 17.30. Found: C, 56.74; H, 4.94; N, 16.90.

Example 24

Compound 86

Scheme 23

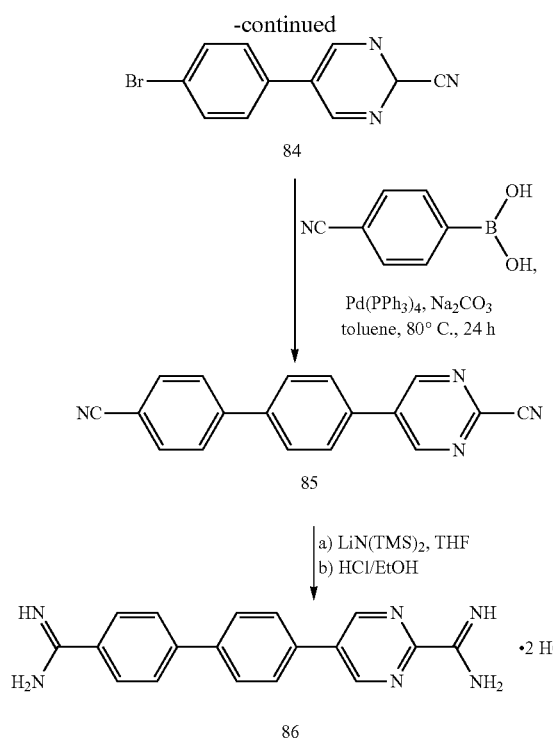

5-(4'-Bromophenyl)-2-pyrimidinecarbonitrile (84). The same procedure described for 5-(4'-bromophenyl)-2-pyridinecarbonitrile was used by employing 5-bromo-2-cyanopyrimidine and 4-bromophenylboronic acid to furnish 84 in 58% yield; mp 202-204° C. $^1$H NMR (DMSO-d$_6$): δ 7.79 (d, J=8.4 Hz, 2H), 7.88 (d, J=8.4 Hz, 1H), 9.39 (s, 2H).

Phenyl[1,1']phenyl[4',5"]pyrimidinyl-4,2"-bis-carbonitrile (85). The above nitrile, 84, and 4-cyanophenylboronic acid were reacted under the above-mentioned Suzuki coupling conditions to give the target dinitrile, 85; yield 74%; mp >300° C. $^1$H NMR (DMSO-d$_6$): δ 7.95-8.01 (m, 6H), 8.08 (d, J=8.4 Hz, 2H), 9.47 (s, 2H).

Phenyl[1,1']phenyl[4',5"]pyrimidinyl-4,2"-bis-amidine hydrochloride salt (86). The same procedure described for the preparation of 66 was used starting with the above dinitrile, 85; 75% yield; mp >300° C. $^1$H NMR (DMSO-d$_6$): δ 7.97 (d, J=8.4 Hz, 2H), 8.03 (d, J=8.4 Hz, 2H), 8.06 (d, J=8.4 Hz, 2H), 9.13 (s, 2H), 9.44 (s, 2H), 9.54 (s, 2H), 9.57 (s, 2H), 9.76 (s, 2H). Anal. Calc. for C$_{18}$H$_{16}$N$_6$·2.0HCl·0.6H$_2$O: C, 54.04; H, 4.84; N, 21.00. Found: C, 54.29; H, 4.68; N, 20.86.

Example 25

Compounds 89, 90 and 91

Scheme 24

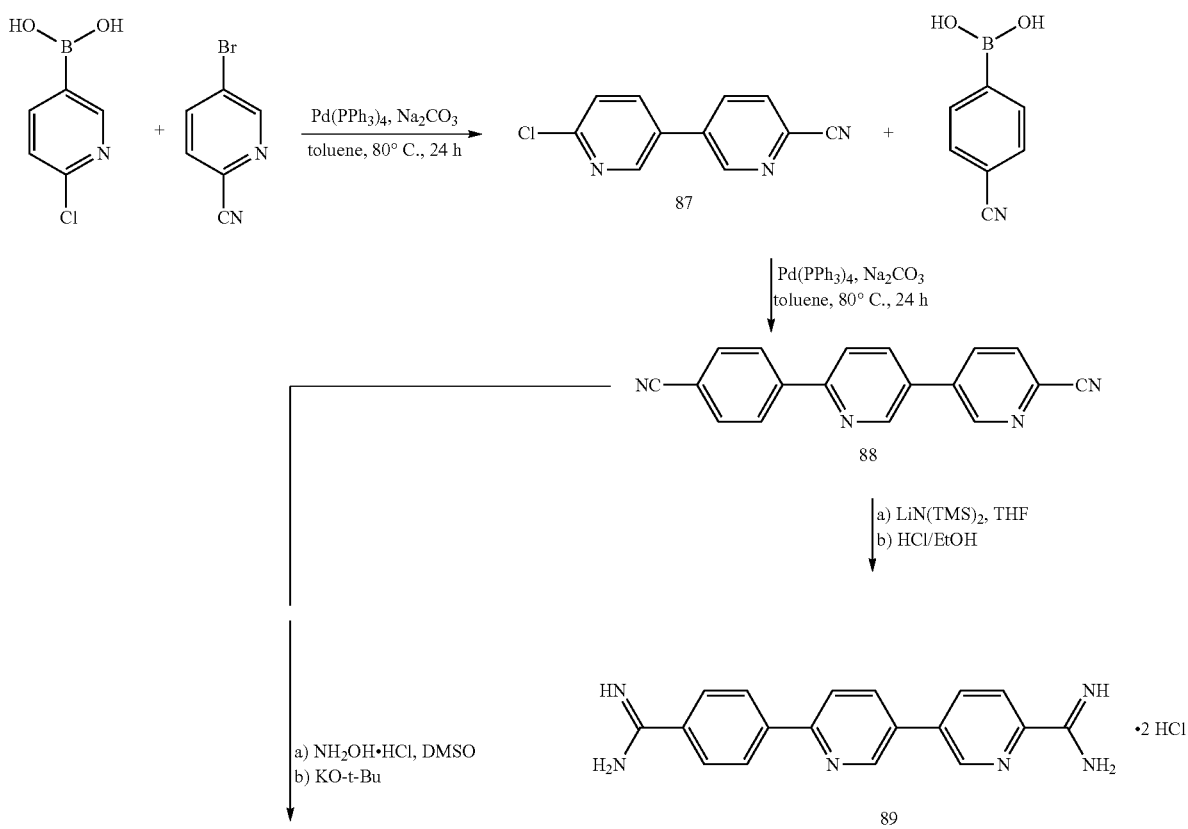

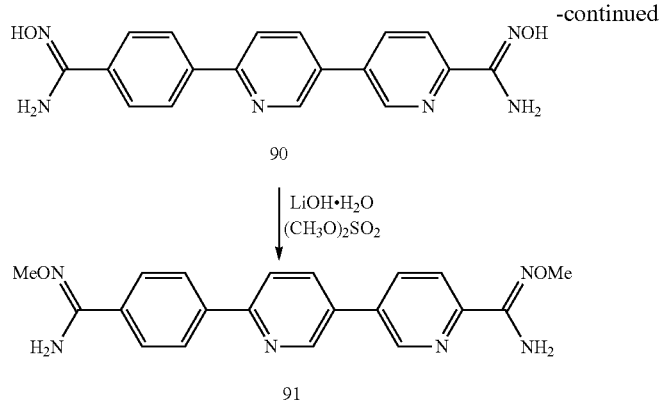

5-(2'-chloro-pyridin-5'-yl)-2-pyridinecarbonitrile (87). The same procedure described for 5-(4'-bromophenyl)-2-pyridinecarbonitrile was used by employing 5-bromo-2-cyanopyridine and 2-chloropyridine-5-boronic acid to furnish 87 in 98% yield; mp 220-224° C. $^1$H NMR (DMSO-$d_6$): δ 7.72 (d, J=8.8 Hz, 1H), 8.19 (d, J=8.4 Hz, 1H), 8.34 (dd, J=2.4, 8.4 Hz, 1H), 8.46 (dd, J=2.4, 8.4 Hz, 1H), 8.90 (d, J=2.0 Hz, 1H), 9.17 (d, J=2.4 Hz, 1H).

Phenyl[1,2']pyridinyl[5',5"]pyridinyl-4,2"-bis-carbonitrile (88). The above nitrile, 87, and 4-cyanophenylboronic acid were reacted under the above-mentioned Suzuki coupling conditions to give the target dinitrile, 88; yield 80%; mp 270-272° C. $^1$H NMR (DMSO-$d_6$): δ 7.99 (d, J=8.4 Hz, 2H), 8.07 (d, J=8.4 Hz, 2H), 8.17 (d, J=8.4 Hz, 1H), 8.32 (d, J=8.4 Hz, 1H), 8.36 (d, J=8.4 Hz, 1H), 8.39 (dd, J=2.0, 8.4 Hz, 1H), 8.75 (dd, J=2.0, 8.4 Hz, 1H), 9.18 (d, J=1.6 Hz, 1H), 9.52 (d, J=2.0 Hz, 1H).

Phenyl[1,2']pyridinyl[5',5"]pyridinyl-4,2"-bis-amidine hydrochloride salt (89). The same procedure described for the preparation of 66 was used starting with the above dinitrile, 88; 71% yield; mp >300° C. $^1$H NMR (DMSO-$d_6$): δ 8.00 (d, J=8.4 Hz, 2H), 8.33 (d, J=8.4 Hz, 1H), 8.43 (d, J=8.4 Hz, 2H), 8.47-8.51 (m, 2H), 8.66 (dd, J=2.0, 8.4 Hz, 1H), 9.18 (s, 2H), 9.26 (d, J=2.0 Hz, 1H), 9.30 (d, J=2.0 Hz, 1H), 9.42 (s, 2H), 9.46 (s, 2H), 9.66 (s, 2H). Anal. Calc. for $C_{18}H_{16}N_6$-2.0HCl-1.0H$_2$O: C, 53.08; H, 4.95; N, 20.63. Found: C, 53.28; H, 4.59; N, 20.34.

Phenyl[1,2']pyridinyl[5',5"]pyridinyl-4,2"-bis-N-hydroxyamidine (90). The same procedure described for the preparation of 67 was used starting with the above dinitrile, 88; 90% yield; mp 240-242° C. $^1$H NMR (DMSO-$d_6$): δ 5.90 (s, 4H), 7.84 (d, J=8.4 Hz, 2H), 7.98 (d, J=8.4 Hz, 1H), 8.17 (d, J=8.4 Hz, 1H), 8.19 (d, J=8.4 Hz, 2H), 8.26 (d, J=8.4 Hz, 1H), 8.31 (d, J=8.4 Hz, 1H), 9.03 (s, 1H), 9.11 (s, 1H), 9.76 (s, 1H), 10.04 (s, 1H).

Phenyl[1,2']pyridinyl[5',5"]pyridinyl-4,2"-bis-N-methoxyamidine hydrochloride salt (91). The same procedure described for the preparation of 68 was used starting with the free base of 90; 70% yield; mp 213-215° C. $^1$H NMR (D$_2$O/DMSO-$d_6$): 3.79 (s, 3H), 3.84 (s, 3H), 6.15 (s, 2H), 6.17 (s, 2H), 7.83 (d, J=8.4 Hz, 2H), 7.98 (d, J=8.4 Hz, 1H), 8.17 (d, J=8.4 Hz, 1H), 8.20 (d, J=8.4 Hz, 2H), 8.27 (dd, J=2.0, 8.4 Hz, 1H), 8.31 (dd, J=2.0, 8.4 Hz, 1H), 9.05 (s, 1H), 9.12 (s, 1H).

Anal. Calc. for $C_{20}H_{20}N_6O_2$-3.0HCl-2.0H$_2$O: C, 46.03; H, 5.22; N, 16.11. Found: C, 46.18; H, 5.22; N, 15.94.

Example 26

Compound 94

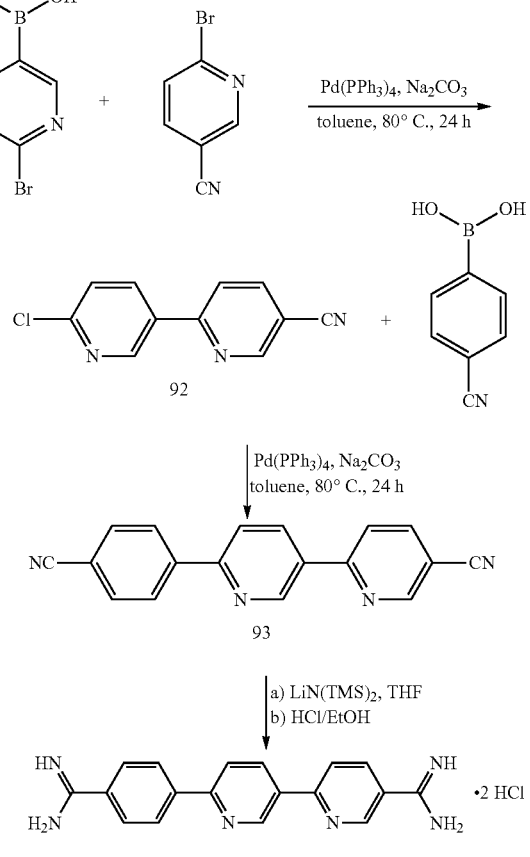

2-(2'-chloro-pyridin-5'-yl)-5-pyridinecarbonitrile (92). The same procedure described for 5-(4'-bromophenyl)-2-pyridinecarbonitrile was used by employing 2-bromo-5-cyanopyridine and 2-chloropyridine-5-boronic acid to furnish 92 in 83% yield; mp 198-200° C. $^1$H NMR (DMSO-d$_6$): δ 7.68 (d, J=8.8 Hz, 1H), 8.29 (d, J=8.4 Hz, 1H), 8.45 (dd, J=2.4, 8.4 Hz, 1H), 8.55 (dd, J=2.4, 8.4 Hz, 1H), 9.12 (d, J=2.0 Hz, 1H), 9.15 (d, J=2.4 Hz, 1H).

Phenyl[1,2']pyridinyl[5',2"]pyridinyl-4,5"-bis-carbonitrile (93). The above nitrile, 92, and 4-cyanophenylboronic acid were reacted under the above-mentioned Suzuki coupling conditions to give the target dinitrile, 93; yield 76%; mp >300° C. $^1$H NMR (DMSO-d$_6$): δ 8.00 (d, J=8.4 Hz, 2H), 8.29 (d, J=8.4 Hz, 1H), 8.39 (d, J=8.4 Hz, 2H), 8.48 (dd, J=2.0, 8.4 Hz, 1H), 8.68 (dd, J=2.0, 8.4 Hz, 1H), 9.16 (d, J=1.6 Hz, 1H), 9.48 (d, J=2.0 Hz, 1H).

Phenyl[1,2']pyridinyl[5',2"]pyridinyl-4,5"-bis-amidine hydrochloride salt (94). The same procedure described for the preparation of 66 was used starting with the above dinitrile, 93; 57% yield; mp >300° C. $^1$H NMR (DMSO-d$_6$): δ 8.00 (d, J=8.4 Hz, 2H), 8.33 (d, J=8.4 Hz, 1H), 8.42-8.44 (m, 4H), 8.71 (dd, J=2.0, 8.4 Hz, 1H), 9.14 (d, J=2.0 Hz, 1H), 9.21 (s, 2H), 9.35 (s, 2H), 9.48 (s, 2H), 9.52 (d, J=2.0 Hz, 1H), 9.65 (s, 2H). Anal. Calc. for C$_{16}$H$_{16}$N$_6$-2.5HCl-1.5H$_2$O: C, 49.75; H, 4.99; N, 19.34. Found: C, 50.03; H, 4.73; N, 19.25.

Example 27

Compound 97

5-(2'-chloro-pyridin-5'-yl)-2-pyrazinecarbonitrile (95). The same procedure described for 5-(4'-bromophenyl)-2-pyridinecarbonitrile was used by employing 2-chloro-5-cyanopyrazine and 2-chloropyridine-5-boronic acid to furnish 95 in 47% yield; mp 118-120° C. $^1$H NMR (DMSO-d$_6$): δ 7.71 (d, J=8.4 Hz, 1H), 8.32 (d, J=8.4 Hz, 1H), 8.48 (dd, J=1.6, 8.4 Hz, 1H), 8.58 (dd, J=2.0, 8.4 Hz, 1H), 9.14 (d, J=1.6 Hz, 1H), 9.17 (d, J=2.0 Hz, 1H).

Phenyl[1,2']pyridinyl[5',5"]pyrazinyl-4,2"-bis-carbonitrile (96). The above nitrile, 95, and 4-cyanophenylboronic acid were reacted under the above-mentioned Suzuki coupling conditions to give the target dinitrile, 96; yield 70%; mp >300° C. $^1$H NMR (DMSO-d$_6$): δ8.01 (d, J=8.4 Hz, 2H), 8.33 (d, J=8.4 Hz, 1H), 8.39 (d, J=8.4 Hz, 2H), 8.68 (dd, J=2.0, 8.4 Hz, 1H), 9.25 (s, 1H), 9.47 (s, 1H), 9.72 (s, 1H).

Phenyl[1,2']pyridinyl[5',5"]pyrazinyl-4,2"-bis-amidine hydrochloride salt (97). The same procedure described for the preparation of 66 was used starting with the above dinitrile, 96; 75% yield; mp >300° C. $^1$H NMR (DMSO-d$_6$): δ 7.80 (d, J=8.4 Hz, 2H), 8.38 (d, J=8.4 Hz, 1H), 8.46 (d, J=8.4 Hz, 2H), 8.97 (dd, J=2.4, 8.4 Hz, 1H), 9.20 (s, 2H), 9.49 (m, 3H), 9.67 (s, 2H), 9.74 (d, J=2.0 Hz, 1H), 9.79 (s, 1H), 9.91 (s, 2H). Anal. Calc. for C$_{17}$H$_{16}$N$_7$-2.7HCl-2.0H$_2$O: C, 45.19; H, 4.84; N, 21.70. Found: C, 45.52; H, 4.71; N, 21.34.

Example 28

Compound 100

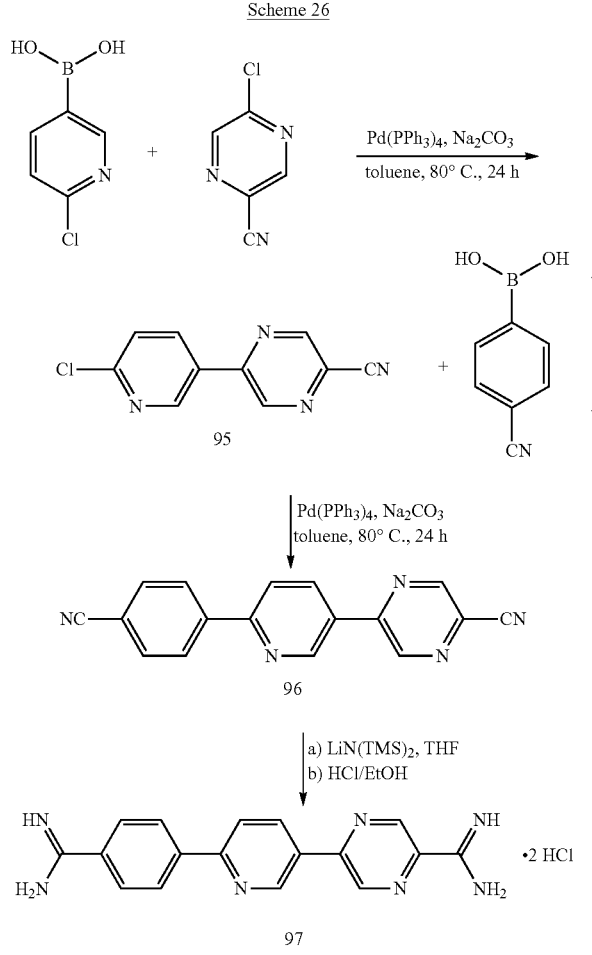

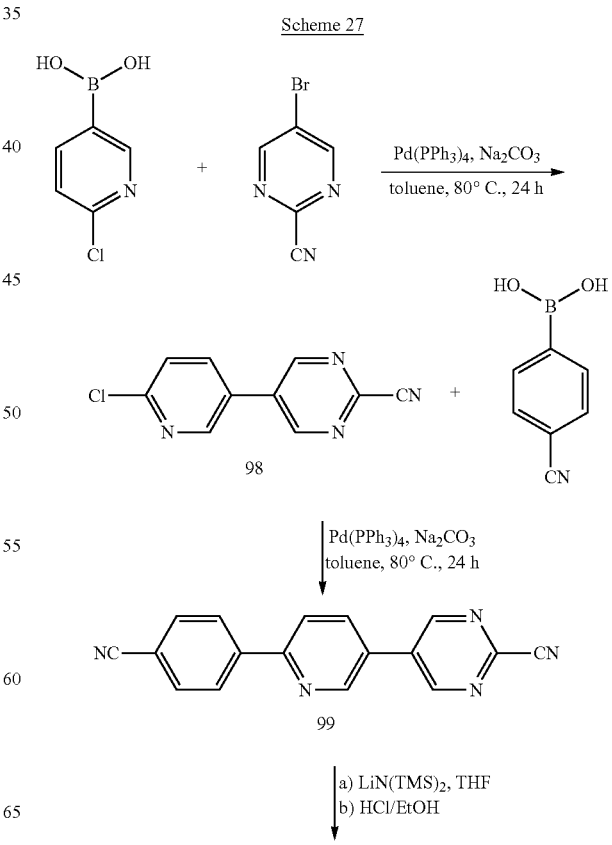

-continued

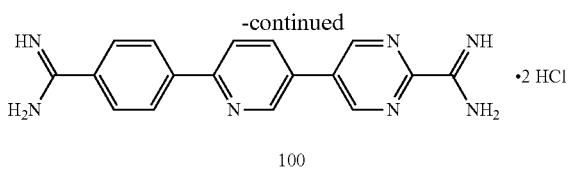
100

5-(2'-chloro-pyridin-5'-yl)-2-pyrimidinecarbonitrile (98). The same procedure described for 5-(4'-bromophenyl)-2-pyridinecarbonitrile was used by employing 5-bromo-2-cyanopyrimidine and 2-chloropyridine-5-boronic acid to furnish 98 in 27% yield; mp 158-160° C. $^1$H NMR (DMSO-$d_6$): δ 7.77 (d, J=8.4 Hz, 2H), 8.41 (dd, J=2.4, 8.4 Hz, 1H), 8.97 (d, J=2.4 Hz, 1H), 9.46 (s, 2H).

Phenyl[1,2']pyridinyl[5',5"]pyrimidinyl-4,2"-bis-carbonitrile (99). The above nitrile, 98, and 4-cyanophenylboronic acid were reacted under the above-mentioned Suzuki coupling conditions to give the target dinitrile, 99; yield 77%; mp 272-274° C. $^1$H NMR (DMSO-$d_6$): δ 8.01 (d, J=8.4 Hz, 2H), 8.34 (d, J=8.4 Hz, 1H), 8.40 (d, J=8.4 Hz, 2H), 8.53 (dd, J=2.0, 8.4 Hz, 1H), 9.28 (d, J=2.0 Hz, 1H), 9.55 (s, 2H).

Phenyl[1,2']pyridinyl[5',5"]pyrimidinyl-4,2"-bis-amidine hydrochloride salt (100). The same procedure described for the preparation of 66 was used starting with the above dinitrile, 99; 51% yield; mp >300° C. $^1$H NMR (DMSO-$d_6$): δ 7.99 (d, J=8.4 Hz, 2H), 8.38 (d, J=8.4 Hz, 1H), 8.44 (d, J=8.4 Hz, 2H), 8.59 (dd, J=2.0, 8.4 Hz, 1H), 9.16 (s, 2H), 9.34 (d, J=2.0 Hz, 1H), 9.47 (s, 2H), 9.60 (s, 2H), 9.62 (s, 2H), 9.62 (s, 4H), 9.79 (s, 2H). Anal. Calc. for $C_{17}H_{16}N_7$-2.0HCl-0.6$H_2O$: C, 50.91; H, 4.57; N, 24.45. Found: C, 50.68; H, 4.49; N, 24.13.

Example 29

Biological Results

The in vitro and/or in vivo activities of compounds 66-69, 71, 73, 75, 77, 80, 83, 86, 89, 91, 94, 97, and 100 are described in Tables 4 and 5 below. Testing methods are as described above in Example 17.

TABLE 4

| | In Vitro Activity | | | | |
|---|---|---|---|---|---|
| Code | Compound Structure | T. b. $IC_{50}$ (nM) | P. f. $IC_{50}$ (nM) | L. d. $IC_{50}$ (nM) | CT $IC_{50}$ (μM) |
| 66 | | 1 | 0.4 | 63 | 1.2 |
| 68 | | 4570 | 637 | | >193 |
| 80 | | | | 84 | 2.8 |
| 83 | | 11 | | 1367 | 26.7 |
| 89 | | 6 | 1 | 510 | 19.9 |
| 91 | | 1980 | 2154 | | 12.8 |
| 77 | | | | 1828 | |
| 75 | | 18 | | 562 | 42.5 |

TABLE 4-continued

In Vitro Activity

| Code | Compound Structure | T. b. IC$_{50}$ (nM) | P. f. IC$_{50}$ (nM) | L. d. IC$_{50}$ (nM) | CT IC$_{50}$ (μM) |
|---|---|---|---|---|---|
| 71 | 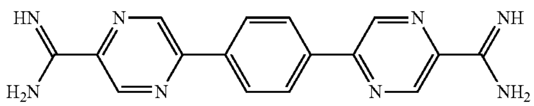 | 7131 | 5170 | 10000 | 46.5 |
| 94 | 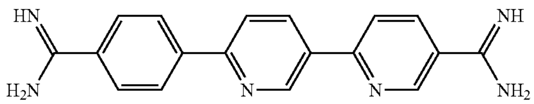 | 7 | 3 | 6815 | 28.3 |
| 100 | 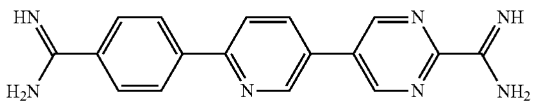 | | | 2641 | |
| 73 | 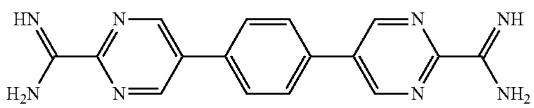 | | | 1722 | |
| 97 | 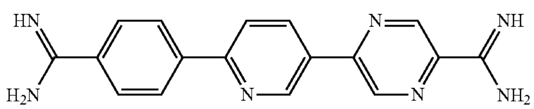 | 14 | | 15568 | 93.4 |
| 86 | 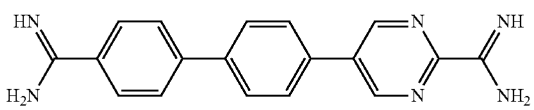 | | | 190 | |

TABLE 5

In vivo Anti- T. b. r. Activity

| Code | Compound Structure | Dosage (mg/kg/route); Cures; Survival (days) |
|---|---|---|
| 66 | 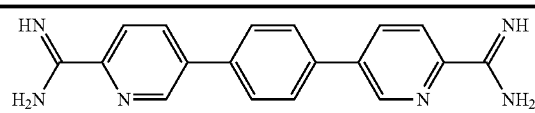 | 5 mg/kg/ip; 0/4 cures; >51.5 d |
| 67 | 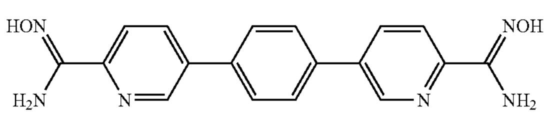 | 25 mg/kg/po; 0/4 cures; 16.25 d |
| 69 | 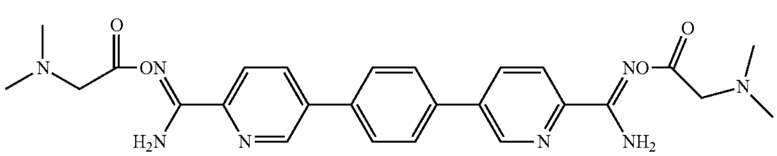 | 25 mg/kg/po; 0/4 cures; 28.25 d |
| 89 | 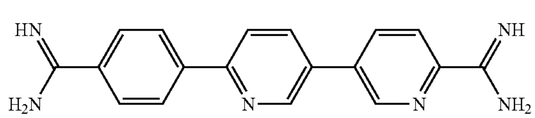 | 5 mg/kg/ip; 3/4 cures; >60 d |

TABLE 5-continued

In vivo Anti- T. b. r. Activity

| Code | Compound Structure | Dosage (mg/kg/route); Cures; Survival (days) |
|---|---|---|
| 91 | 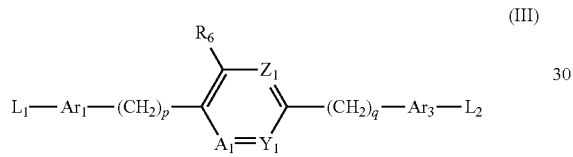 | 25 mg/kg/ip; 0/4 cures; 22.25 d |
| 94 | 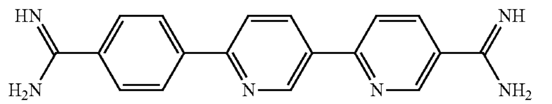 | 5 mg/kg/ip; 4/4 cures; >60 d |

It will be understood that various details of the invention may be changed without departing from the scope of the invention. Furthermore, the foregoing description is for the purpose of illustration only, and not for the purpose of limitation.

What is claimed is:

1. An aza teraryl compound of Formula (III):

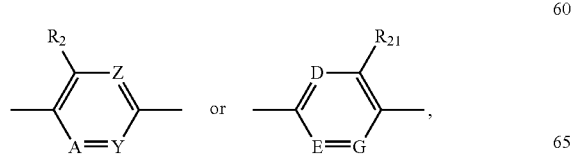

wherein:
p and q are each independently an integer 0, 1, 2, 3, 4, 5, 6, 7, or 8;
$A_1$, $Y_1$, and $Z_1$ are selected from the group consisting of N and $CR_7$, wherein $R_7$ is selected from the group consisting of H, hydroxy, halo, nitro, alkyl, substituted alkyl, alkoxy, aryl, substituted aryl, and aryloxy, wherein one of $A_1$, $Y_1$, and $Z_1$ is N;
$R_6$ is selected from the group consisting of H, hydroxy, halo, nitro, alkyl, substituted alkyl, alkoxy, aryl, substituted aryl, and aryloxy;
$Ar_1$ is:

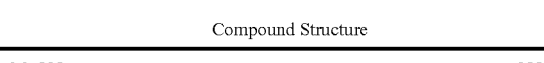

wherein m is an integer 0, 1, 2, 3, or 4; and each $R_1$ is independently selected from the group consisting of H, hydroxy, halo, nitro, alkyl, substituted alkyl, alkoxy, aryl, substituted aryl, and aryloxy;
$Ar_3$ is:

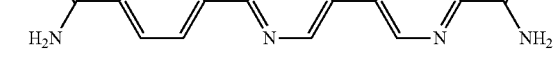

wherein:
A, D, E, G, Y, and Z are independently selected from the group consisting of N and $CR_4$, wherein $R_4$ is selected from the group consisting of H, hydroxy, halo, nitro, alkyl, substituted alkyl, alkoxy, aryl, substituted aryl, and aryloxy, wherein at least one of A, D, E, G, Y, and Z is nitrogen;
$R_2$ and $R_{21}$ are selected from the group consisting of H, hydroxy, halo, nitro, alkyl, substituted alkyl, alkoxy, aryl, substituted aryl, and aryloxy; and
$L_1$ and $L_2$ are independently selected from the group consisting of:

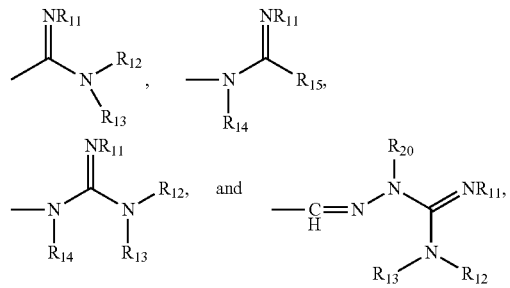

wherein:
$R_{11}$, $R_{12}$, $R_{13}$, $R_{14}$, $R_{15}$, and $R_{20}$ are each independently selected from the group consisting of H, alkyl, substituted alkyl, cycloalkyl, aryl, substituted aryl, aralkyl, hydroxy, alkoxy, hydroxyalkyl, hydroxycycloalkyl, alkoxycycloalkyl, aminoalkyl, acyloxyl, alkylaminoalkyl, and alkoxycarbonyl; or
$R_{11}$ and $R_{12}$ together represent a $C_2$ to $C_{10}$ alkyl, $C_2$ to $C_{10}$ hydroxyalkyl, or a $C_2$ to $C_{10}$ alkylene; or
$R_{11}$ and $R_{12}$ together are:

wherein u is an integer 1, 2, 3, or 4; and $R_{16}$ is H or —$CONHR_{17}NR_{18}R_{19}$, wherein $R_{17}$ is alkyl, and $R_{18}$ and $R_{19}$ are each independently selected from the group consisting of H and alkyl;

wherein substituted alkyl is alkyl substituted by one or more of the group consisting of alkyl, aryl, halo, arylamino, acyl, hydroxy, aryloxy, alkoxy, alkylthio, arylthio, aralkyloxy, aralkylthio, carboxyl, alkoxycarbonyl, cycloalkyl, nitro, amino, alkylamino, dialkylamino, sulfate, and mercapto; and substituted aryl is aryl substituted by one or more of the group consisting of alkyl, aryl, aralkyl, hydroxy, alkoxy, aryloxy, aralkyloxy, carboxyl, acyl, halo, nitro, alkoxycarbonyl, aryloxycarbonyl, aralkylcarbonyl, acyloxyl, acylamino, aroylamino, carbamoyl, alkylcarbamoyl, dialkylcarbamoyl, arylthio, alkylthio, amino, alkylamino, dialkylamino, arylamino, diarylamino, sulfate, and mercapto;

or a pharmaceutically acceptable salt thereof.

2. The compound of claim 1, wherein $L_2$ is ortho to at least one nitrogen G, Y, or Z.

3. The compound of claim 2, wherein:
Ar$_3$ is:

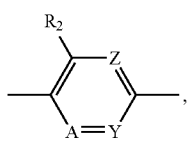

and
the compound of Formula (III) has a structure of Formula (IIIa-4):

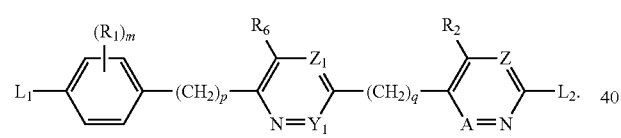
(IIIa-4)

4. The compound of claim 3, wherein the compound is selected from the group consisting of:

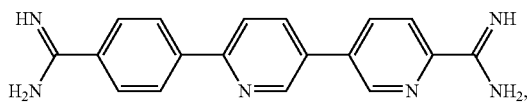

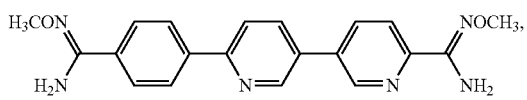

and

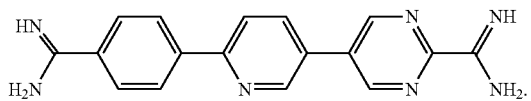

5. The compound of claim 2, wherein:
Ar$_3$ is:

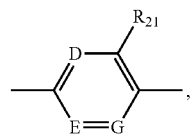

and
the compound of Formula (III) has a structure of Formula (IIIa-5):

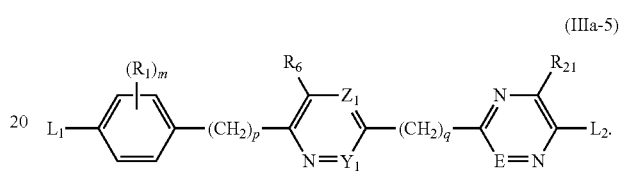
(IIIa-5)

6. The compound of claim 5, wherein the compound has the structure:

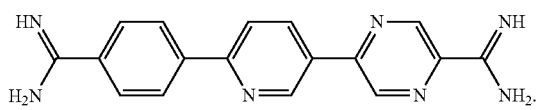

7. The compound of claim 1, wherein:
Ar$_3$ is:

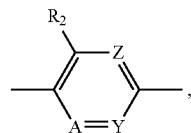

and
the compound of Formula (III) has a structure of Formula (IIIa-3):

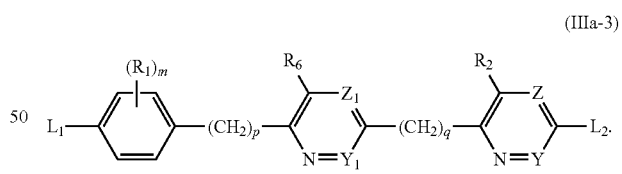
(IIIa-3)

8. The compound of claim 7, wherein the compound of Formula (IIIa-3) has the structure:

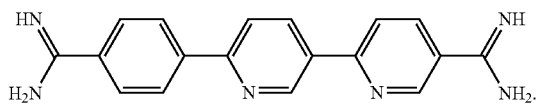

9. A pharmaceutical formulation comprising:
(a) an aza teraryl compound of claim 1; and
(b) a pharmaceutically acceptable carrier.

* * * * *